(12) United States Patent
Samadani

(10) Patent No.: US 11,944,449 B2
(45) Date of Patent: Apr. 2, 2024

(54) METHODS AND KITS FOR ASSESSING NEUROLOGICAL FUNCTION AND LOCALIZING NEUROLOGICAL LESIONS

(71) Applicant: New York University, New York, NY (US)

(72) Inventor: Uzma Samadani, Wayzata, MN (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 18/167,337

(22) Filed: Feb. 10, 2023

(65) Prior Publication Data

US 2023/0255540 A1    Aug. 17, 2023

Related U.S. Application Data

(63) Continuation of application No. 16/322,355, filed as application No. PCT/US2017/044972 on Aug. 1, 2017, now Pat. No. 11,642,071.

(60) Provisional application No. 62/369,848, filed on Aug. 2, 2016.

(51) Int. Cl.
| | |
|---|---|
| A61B 5/00 | (2006.01) |
| A61B 3/00 | (2006.01) |
| A61B 3/08 | (2006.01) |
| A61B 3/103 | (2006.01) |
| A61B 3/107 | (2006.01) |
| A61B 3/113 | (2006.01) |
| A61B 3/12 | (2006.01) |
| A61B 3/14 | (2006.01) |
| A61B 3/16 | (2006.01) |
| A61B 5/03 | (2006.01) |
| A61B 5/11 | (2006.01) |

(52) U.S. Cl.
CPC .......... *A61B 5/4064* (2013.01); *A61B 3/0091* (2013.01); *A61B 3/085* (2013.01); *A61B 3/103* (2013.01); *A61B 3/107* (2013.01); *A61B 3/113* (2013.01); *A61B 3/12* (2013.01); *A61B 3/14* (2013.01); *A61B 3/16* (2013.01); *A61B 5/031* (2013.01); *A61B 5/1114* (2013.01); *A61B 5/7278* (2013.01); *A61B 5/7282* (2013.01)

(58) Field of Classification Search
CPC ... A61B 3/085; A61B 3/113; A61B 3/14–158; A61B 3/18–185; A61B 5/163; A61B 5/4064; G06F 3/013
See application file for complete search history.

(56) References Cited

U.S. PATENT DOCUMENTS

| | | | |
|---|---|---|---|
| 2015/0130703 A1* | 5/2015 | Ghajar | G06F 3/013 345/156 |
| 2015/0305661 A1* | 10/2015 | Seassau | A61B 3/113 600/558 |

FOREIGN PATENT DOCUMENTS

WO    WO-2014204904 A1 * 12/2014 ........... A61B 3/0025

\* cited by examiner

*Primary Examiner* — Thaddeus B Cox
(74) *Attorney, Agent, or Firm* — SLEMAN & LUND LLP

(57) ABSTRACT

A method for assessing neurological function in a subject includes a) prompting a user to follow a moving saccade-evoking stimulus on a display, b) tracking eye movement of the subject while the user follows the moving stimulus, c) collecting a first eye conjugacy data of the subject relating to the saccade-evoking stimulus, and d) comparing the first eye conjugacy data with a second eye conjugacy data, the second eye conjugacy data relating to an anti-saccade stimulus.

8 Claims, 67 Drawing Sheets

Cranial nerves III, IV and VI move the eyes in a square
Right eye

Cranial nerves III, IV and VI move the eyes in a square
Left eye

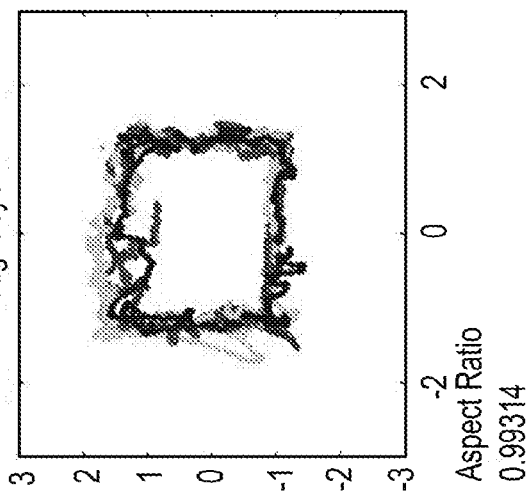
FIG. 2A
FIG. 2B
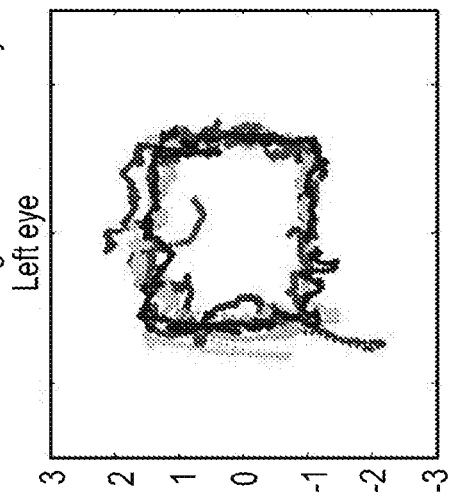
FIG. 2C
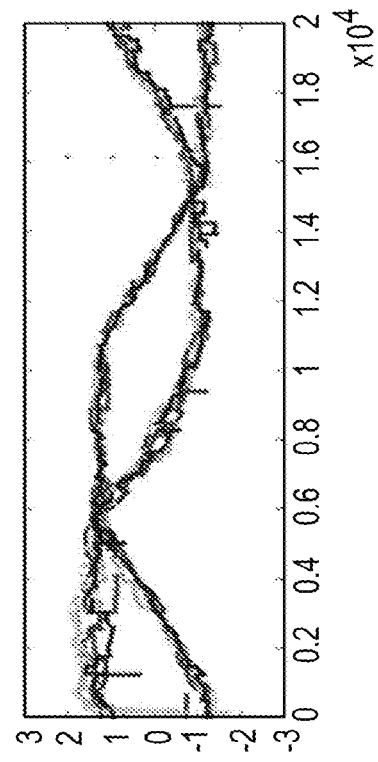
FIG. 2D
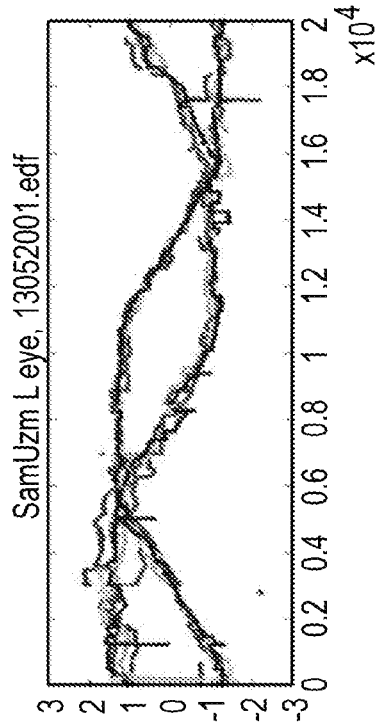

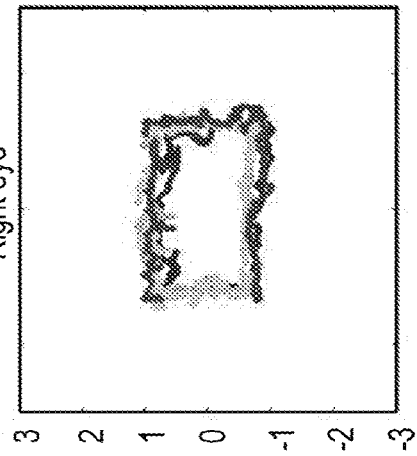
FIG. 4A
FIG. 4B
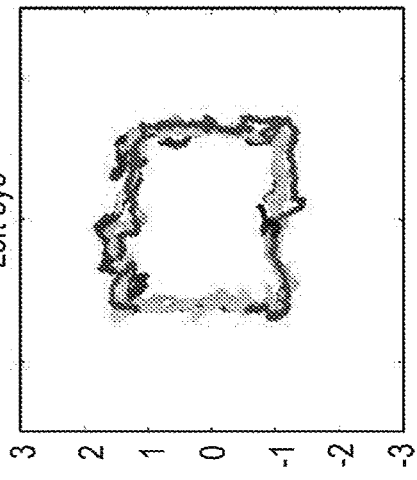
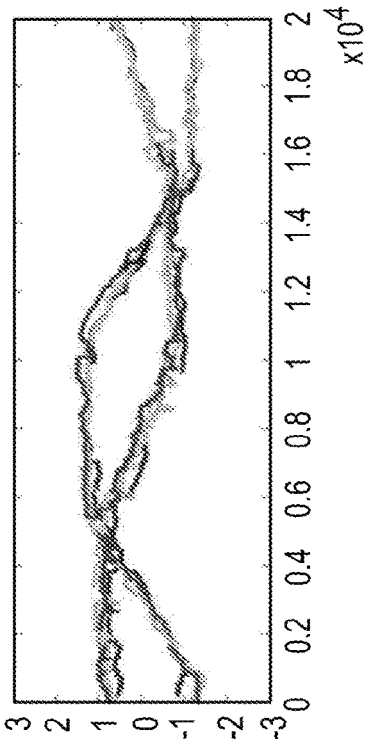
FIG. 4C
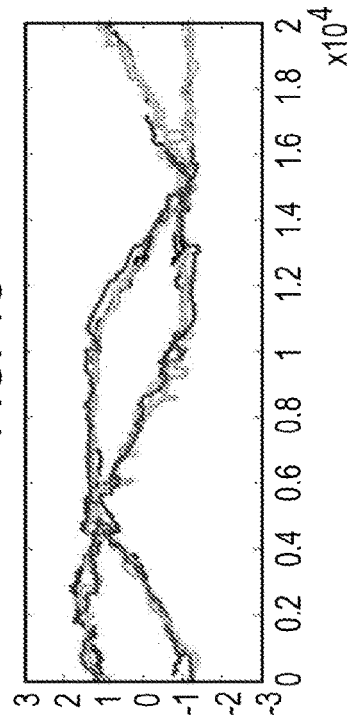
FIG. 4D

Comparison of gaze conjugacy among different subjects

Comparison of gaze conjugacy among different subjects

Comparison of gaze conjugacy among different subjects

Comparison of gaze conjugacy among different subjects

Comparison of gaze conjugacy among different subjects

Comparison of gaze conjugacy among different subjects

Age as a function of Conjugate Gaze

Conjugacy of Gaze Based on Sex

Relationship of Vertical and Horizontal Conjugacy of Gaze

Test/Retest Reliability

Stationary to Portable Reliability

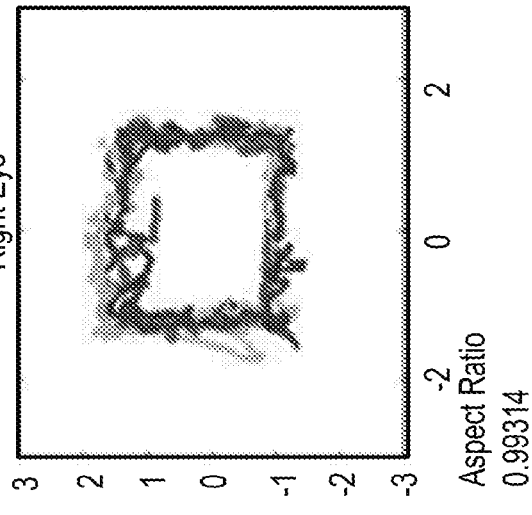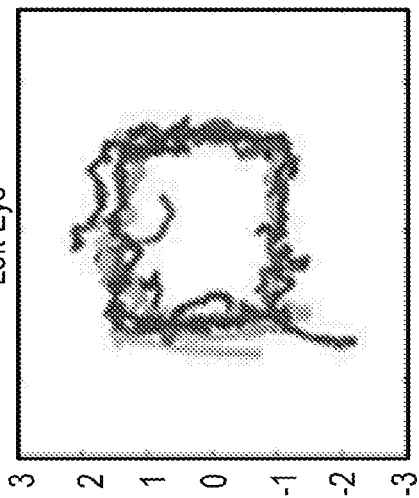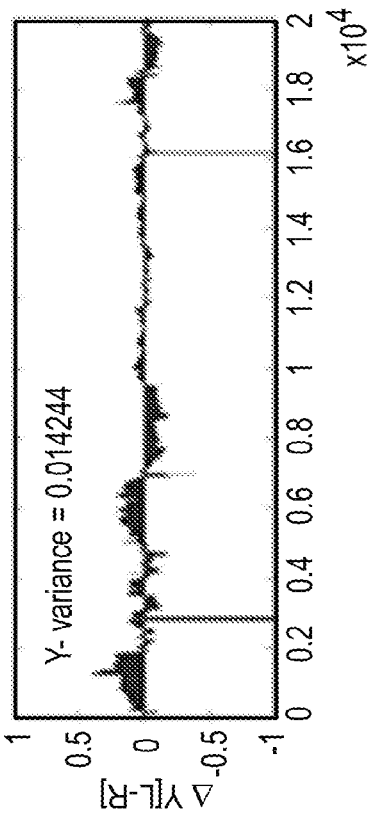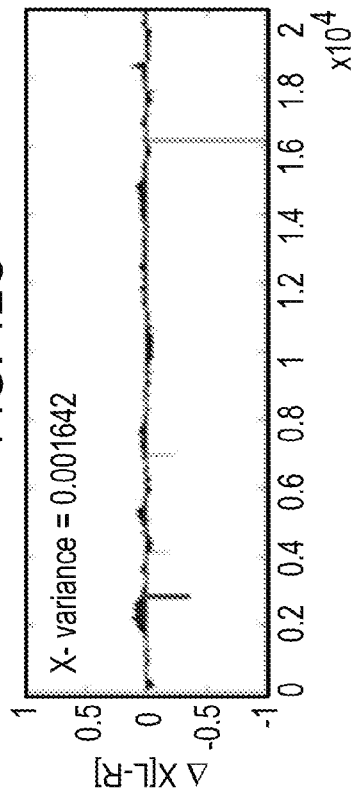

Cranial nerve IV palsy
Left Eye
Aspect Ratio
1.0906

Cranial nerve IV palsy
Right Eye
Aspect Ratio
0.99589

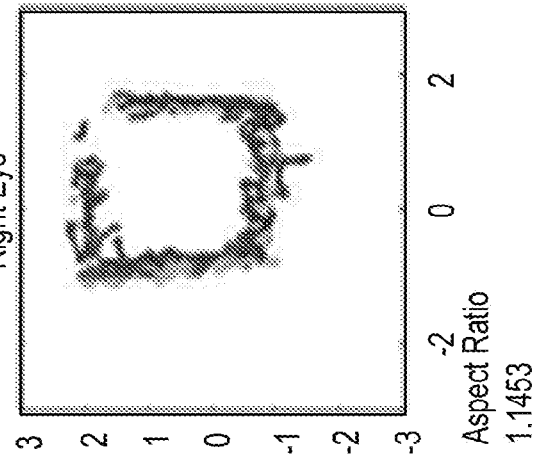
FIG. 12M
Cranial nerve VI palsy
Left Eye
Aspect Ratio
1.1649
FIG. 12N
Cranial nerve VI palsy
Right Eye
Aspect Ratio
1.1453
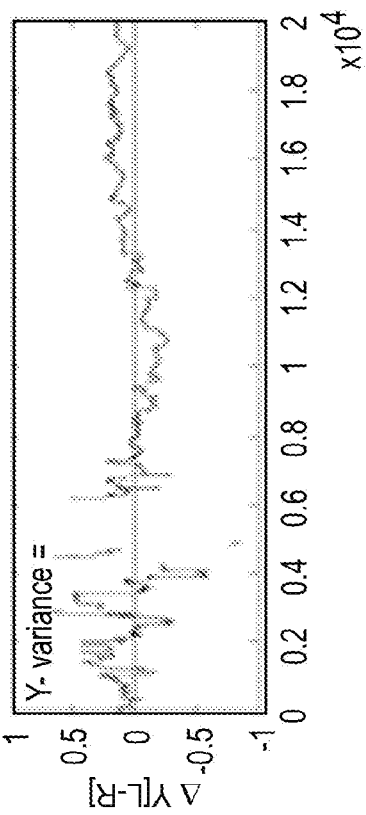
FIG. 12O
FIG. 12P

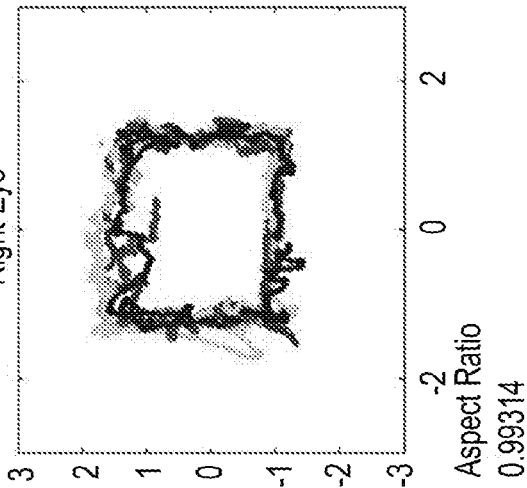
FIG. 15A
Binocular Tracking of A Normal Subject: Left Eye
Aspect Ratio 0.97516
FIG. 15B
Binocular Tracking of A Normal Subject: Right Eye
Aspect Ratio 0.99314
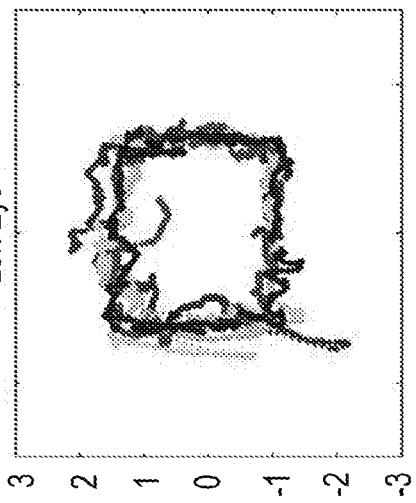
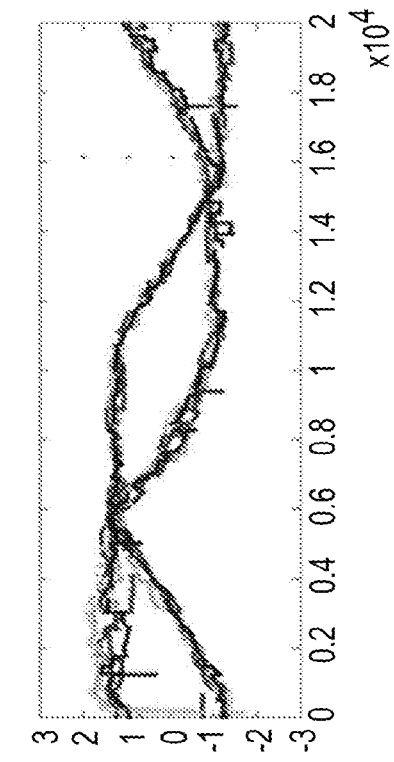
FIG. 15D
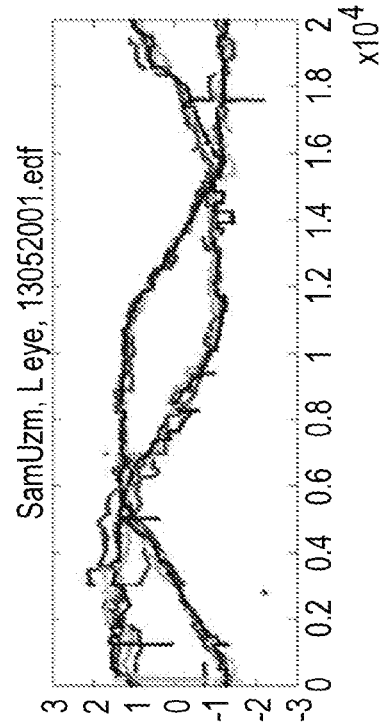
FIG. 15C
SamUzm, L eye, 13052001.edf Eye movement tracking of a patient with conjunctivitis due to a blocked lacrimal duct
Right Eye Aspect Ratio
0.65561

Eye movement tracking of a patient with conjunctivitis due to a blocked lacrimal duct
Left Eye Aspect Ratio
0.97675

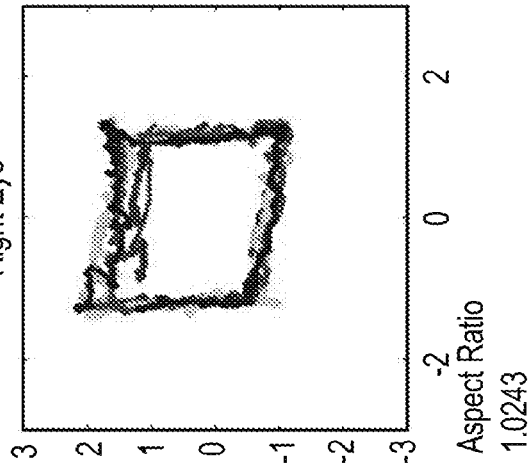
FIG. 16H
After resolution of symptoms
Right Eye
Aspect Ratio
1.0243
FIG. 16G
After resolution of symptoms
Left Eye
Aspect Ratio
1.0196
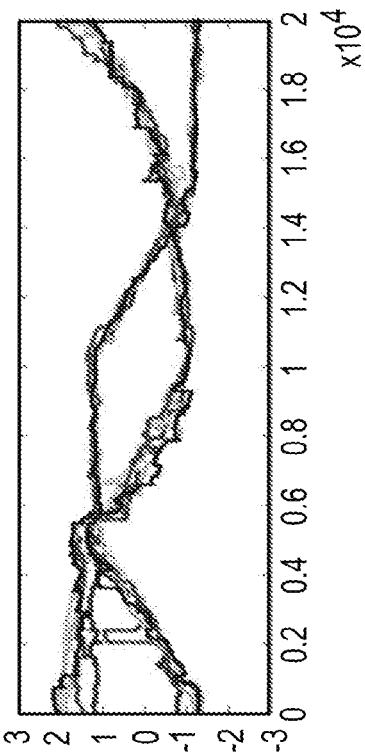
FIG. 16J
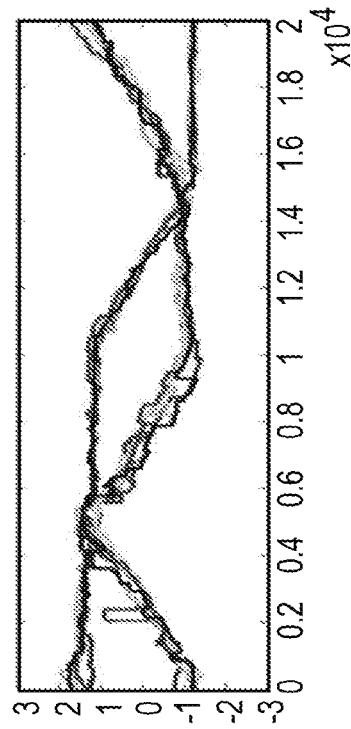
FIG. 16I

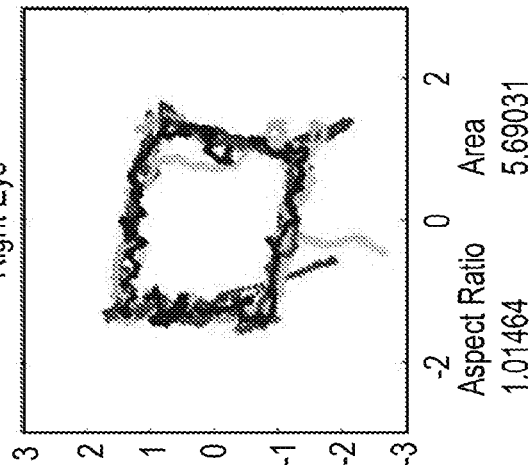
FIG. 17A
A 9 year old boy with a history of lymphoma and exotrophic strabismus
Left Eye
Aspect Ratio  Area
0.85675      4.61996
FIG. 17B
A 9 year old boy with a history of lymphoma and exotrophic strabismus
Right Eye
Aspect Ratio  Area
1.01464      5.69031
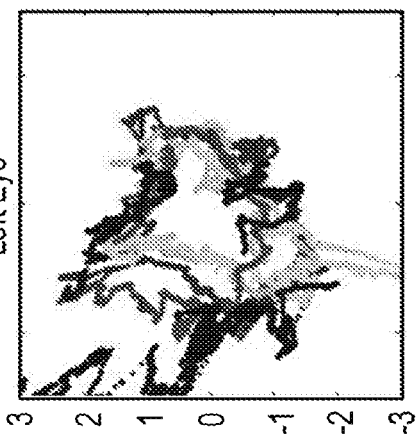
FIG. 17C
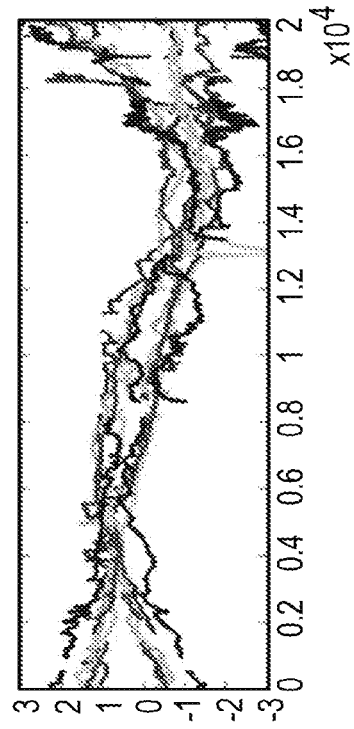
FIG. 17D

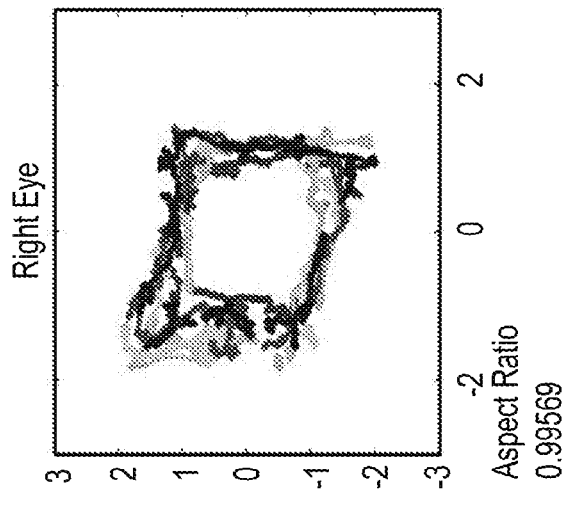
FIG. 18A
Cranial nerve IV palsy
Left Eye
Aspect Ratio
1.0906
FIG. 18B
Cranial nerve IV palsy
Right Eye
Aspect Ratio
0.99569
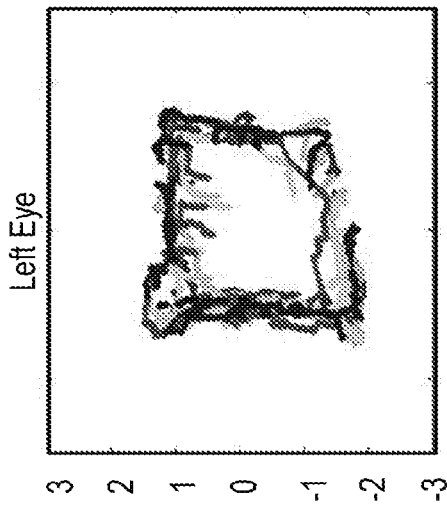
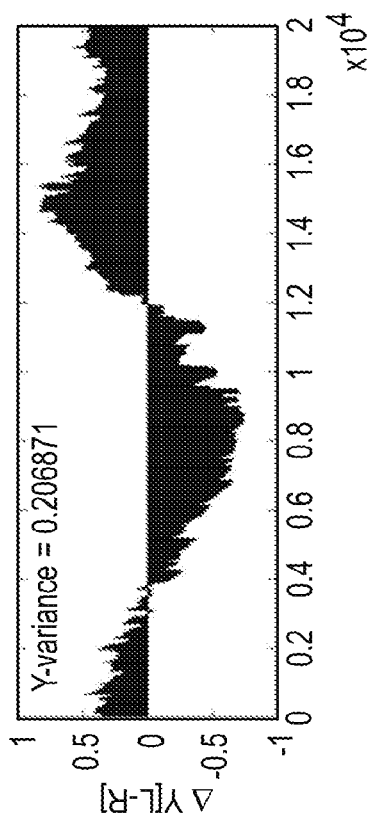
FIG. 18C
PhiFre, 13071507. edf, Total Variance = 0.231381
X-variance = 0.024510
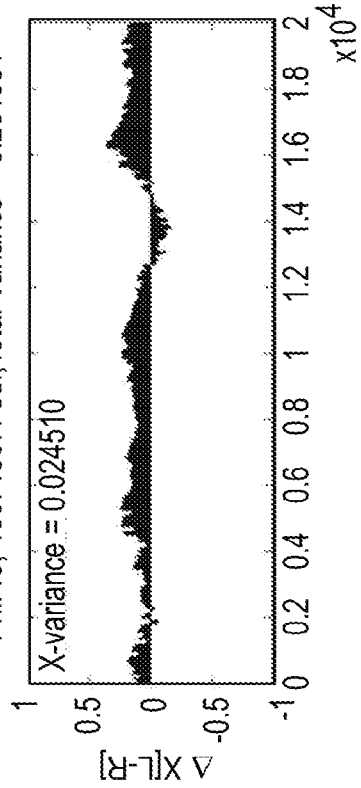
FIG. 18D
Y-variance = 0.206871

Diabetic cranial nerve III palsy
Left Eye

Diabetic cranial nerve III palsy
Right Eye

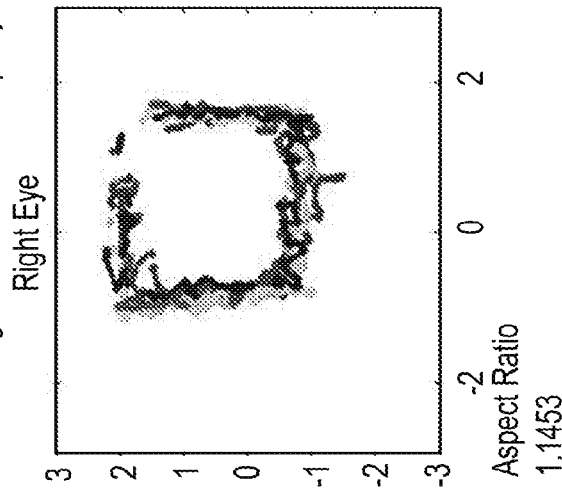
FIG. 18I
Post-surgical cranial nerve VI palsy
Left Eye
Aspect Ratio
1.1649
FIG. 18J
Post-surgical cranial nerve VI palsy
Right Eye
Aspect Ratio
1.1453
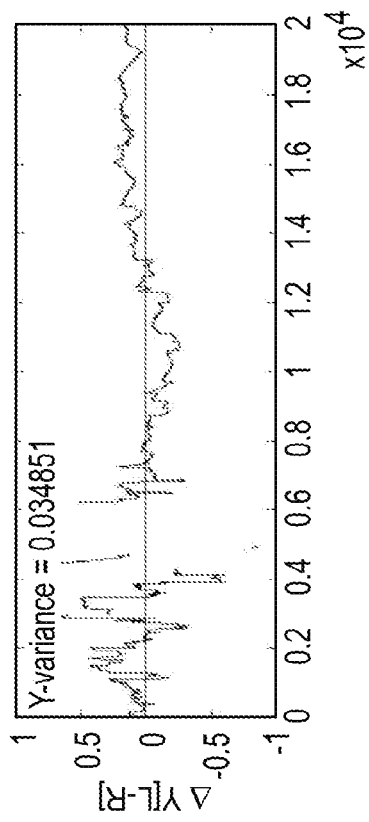
FIG. 18K
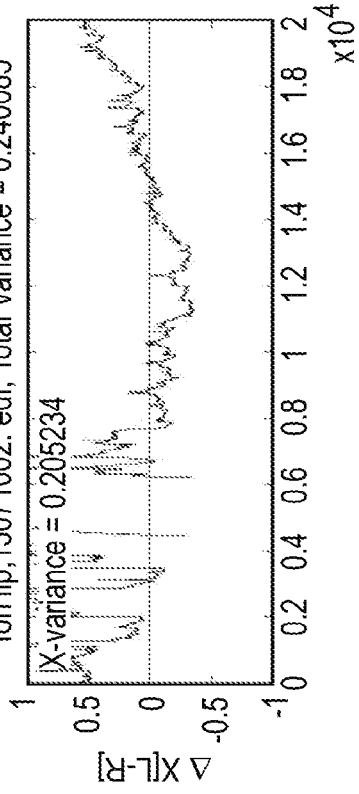
FIG. 18L A 35 year old female ruptured a cerebral aneurysm resulting in subarachnoid hemorrhage
Left Eye
Aspect Ratio 0.67444

A 35 year old female ruptured a cerebral aneurysm resulting in subarachnoid hemorrhage
Right Eye
Aspect Ratio 1.0862

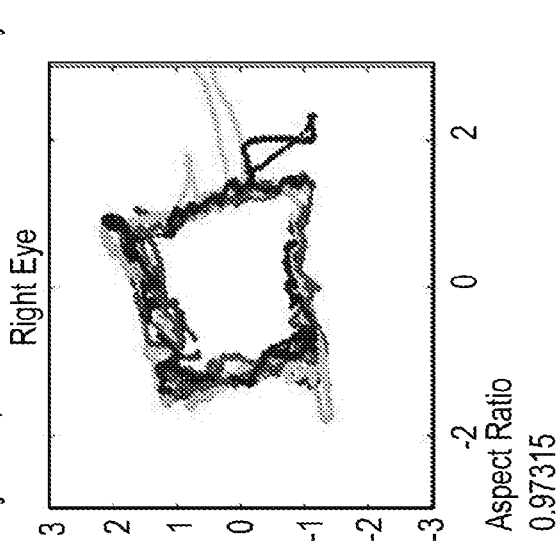
FIG. 19G
6 days later, after embolization of the aneurysm
Left Eye
Aspect Ratio
1.0248
FIG. 19H
6 days later, after embolization of the aneurysm
Right Eye
Aspect Ratio
0.97315
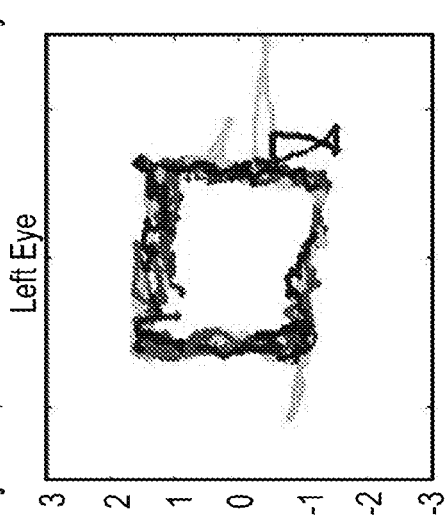
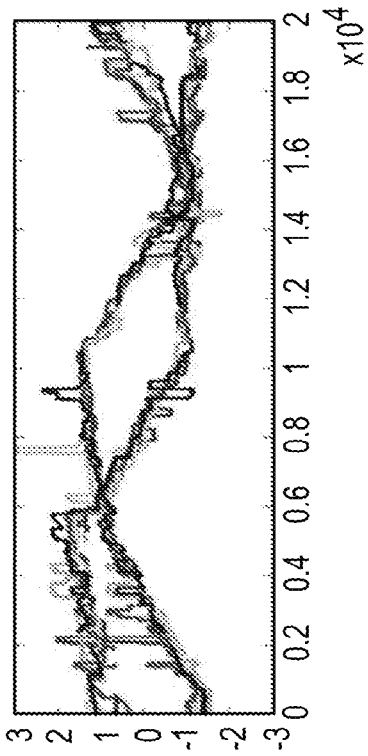
FIG. 19I
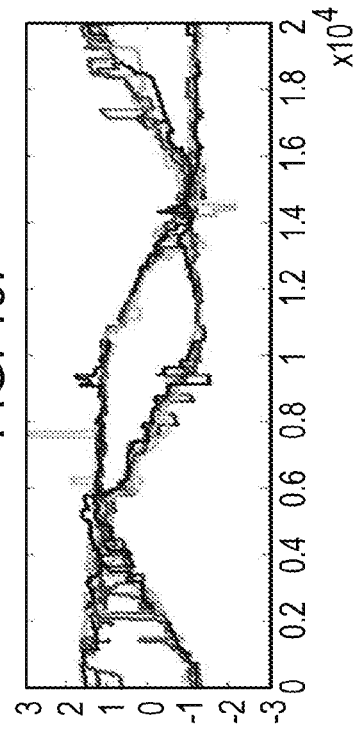
FIG. 19J

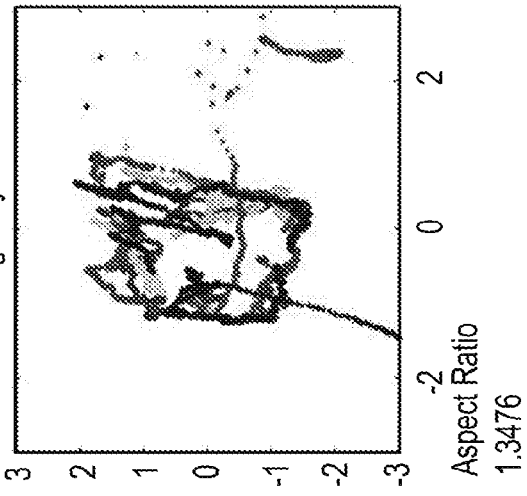
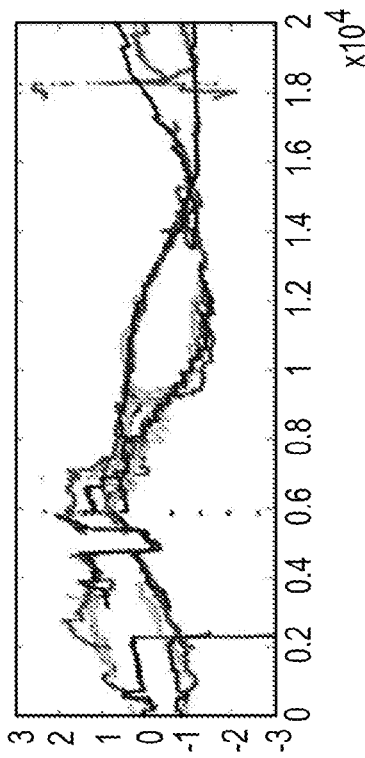
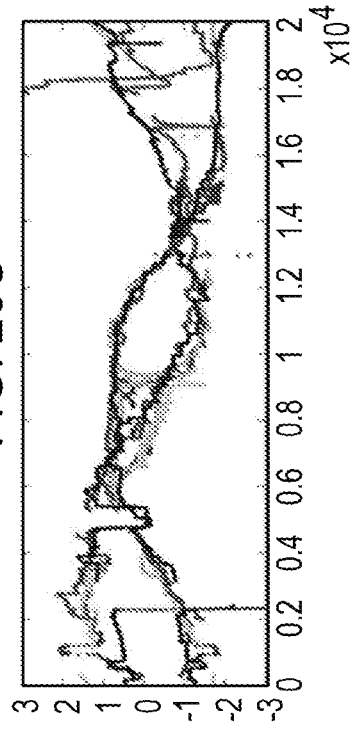

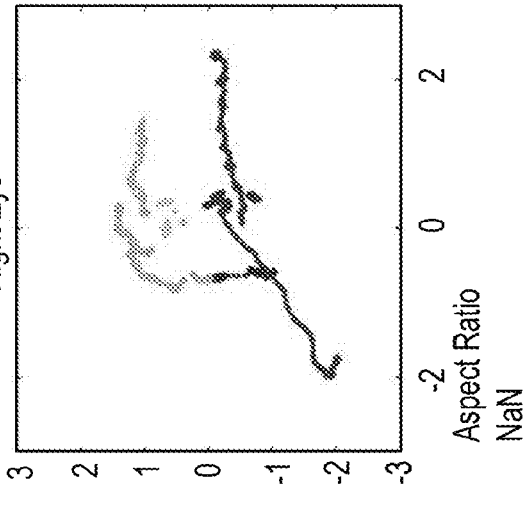
FIG. 21A
FIG. 21B
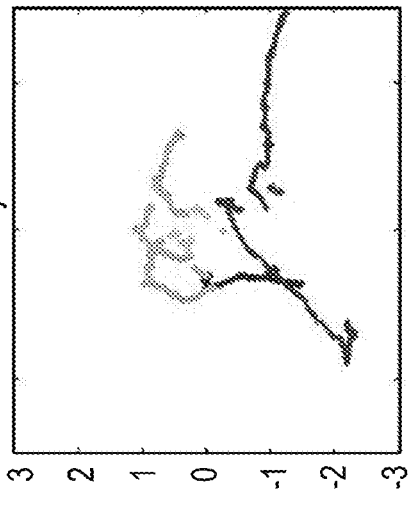
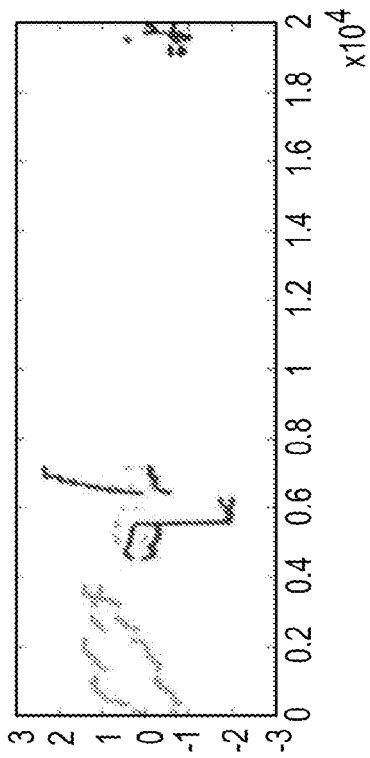
FIG. 21C
FIG. 21D
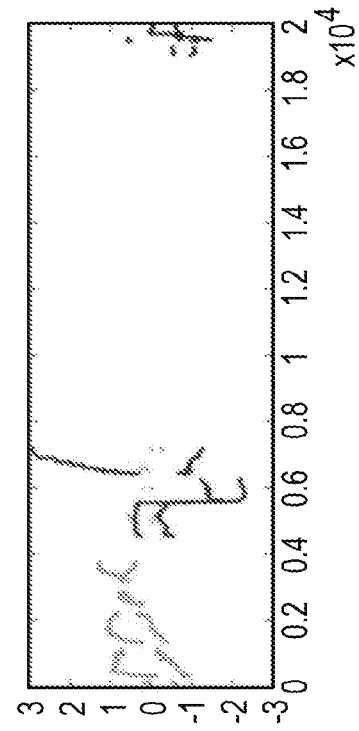

total var.235624

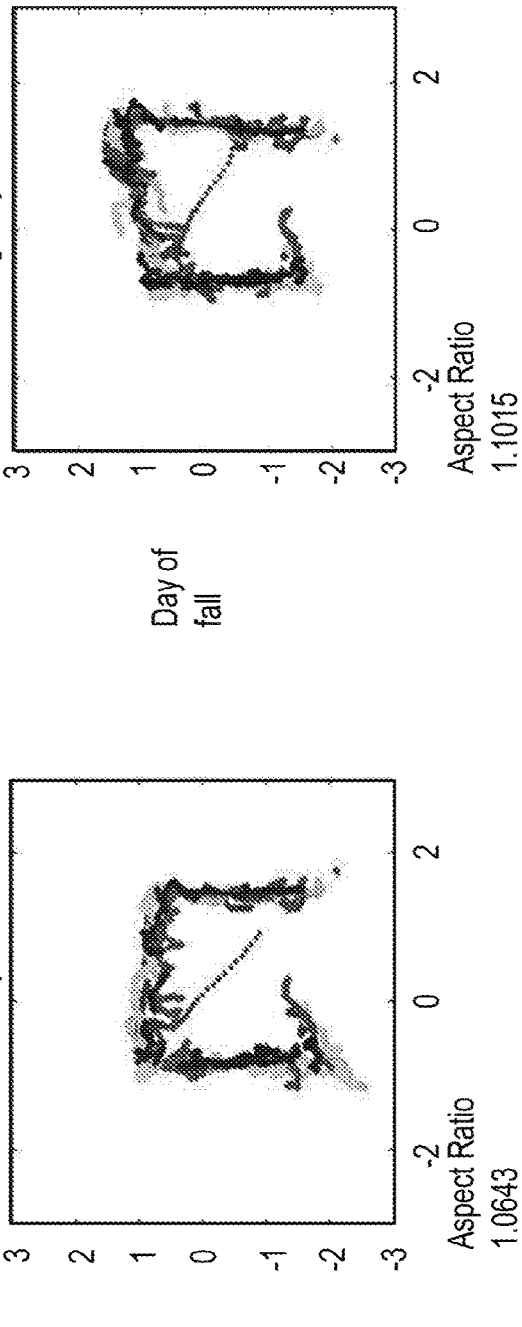
FIG. 22A
53 year old female who fell down steps on a bus, diagnosed with "concussion" in ER
Left Eye
FIG. 22B
53 year old female who fell down steps on a bus, diagnosed with "concussion" in ER
Right Eye
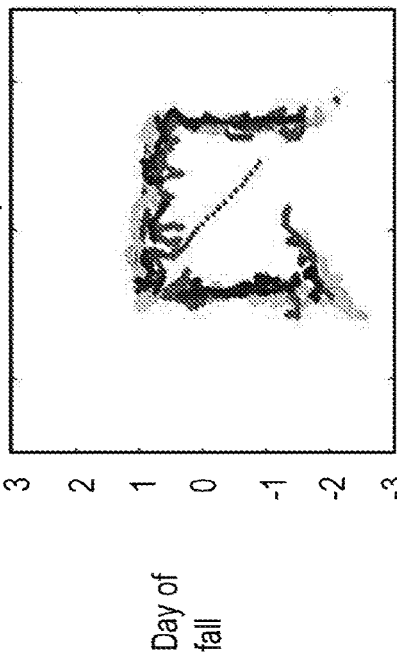
FIG. 22C
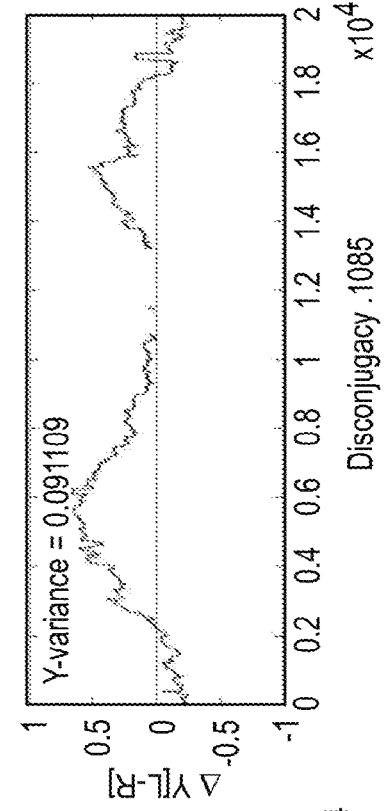
FIG. 22D
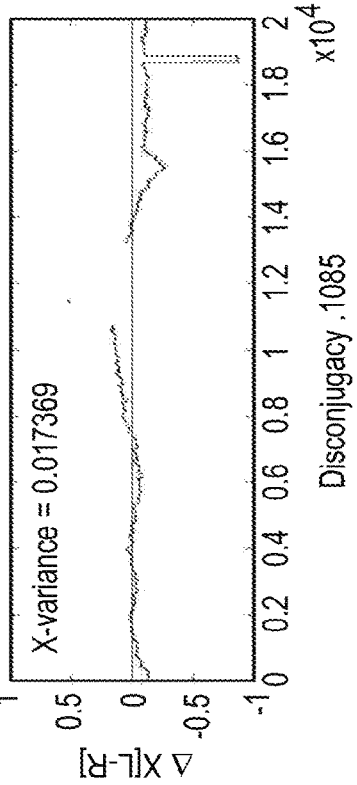

53 year old female who fell down steps on a bus, diagnosed with "concussion" in ER
Left Eye 53 year old female who fell down steps on a bus, diagnosed with "concussion" in ER
Right Eye

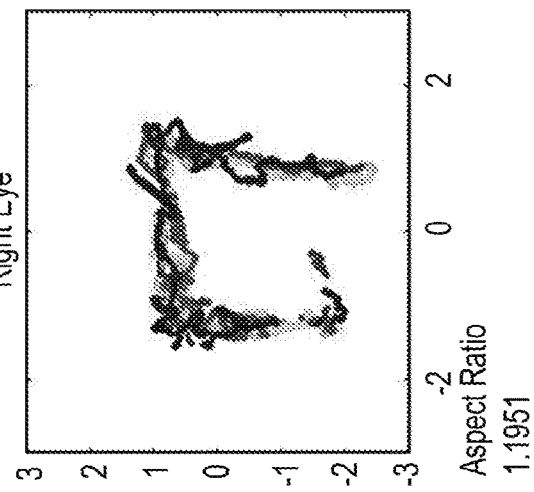
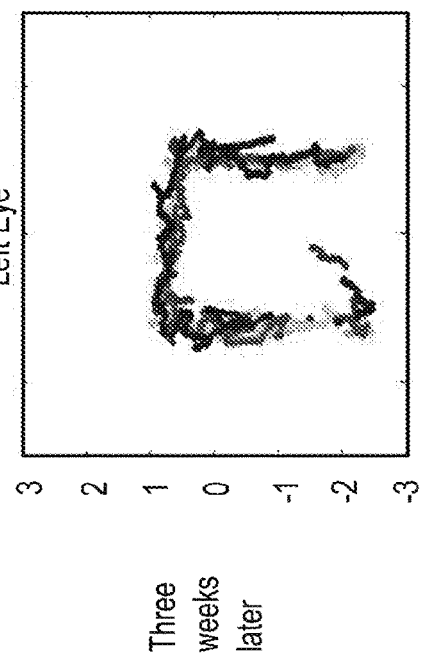
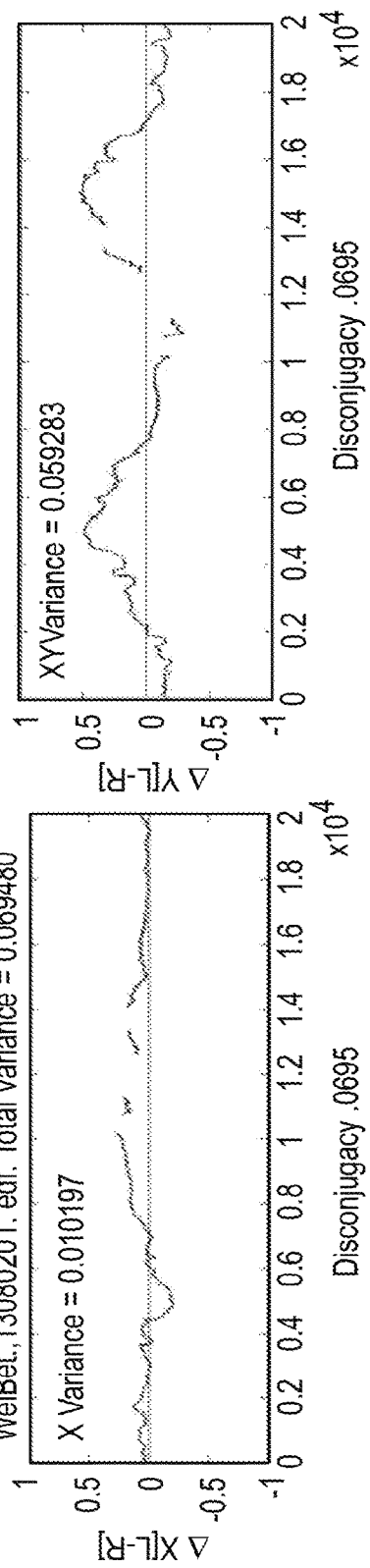
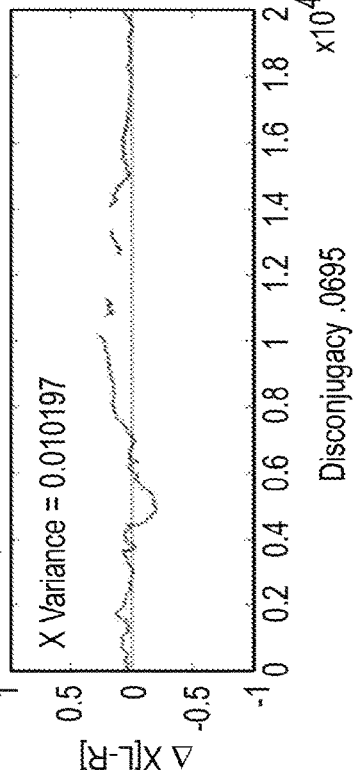

Disconjugate gaze in a patient with a severed IIIrd nerve $L_1$-AR: -NaN (0.9590 to 1.0460)

$R_1$-AR: NaN (0.9421 to 1.0548)

$L_2$-AR: 3.1584* (0.9590 to 1.0460)

$R_2$-AR: 0.876* (0.9421 to 1.0548)

$L_3$-AR: 1.2737* (0.9590 to 1.0460)

$R_3$-AR: -0.1711* (0.9421 to 1.0548)

$L_4$-AR: NaN (0.9590 to 1.0460)

$R_4$-AR: NaN (0.9421 to 1.0548)

Disconjugate gaze in a patient with a severed IIIrd nerve $L_5$ -AR: NaN (0.9590 to 1.0460)

$R_5$ -AR: NaN (0.9421 to 1.0548)

$L_{1-5}$ $R_{1-5}$ $L_{1-5AVG}$ -AR: 2.2161* (0.9590 to 1.0460)

$R_{1-5AVG}$ -AR: 0.0082* (0.9421 to 1.0548)

A normal person watching TV (naturalistic viewing) has eyes that move together with a conjugacy of 0.0169 (normal range is -.0857 to 0.1598)

$L_1$-AR: 0.2870* (0.9590 to 1.0460)

$R_1$-AR: 0.2643* (0.9421 to 1.0548)

Note how eyes move together $L_2$-AR: NaN (0.9590 to 1.0460)

$R_2$-AR: NaN (0.9421 to 1.0548)

Note how eyes move together $L_3$-AR: NaN (0.9590 to 1.0460)

$R_3$-AR: NaN (0.9421 to 1.0548)

Note how eyes move together $L_4$-AR: NaN (0.9590 to 1.0460)

$R_4$-AR: NaN (0.9591 to 1.0548)

Note how eyes move together

A normal person watching TV (naturalistic viewing) has eyes that move together with a conjugacy of 0.0169 (normal range is -.0857 to 0.1598)

$L_5$ -AR : NaN (0.9590 to 1.0460)

Note how eyes move together $R_5$ -AR : NaN (0.9421 to 1.0548)

$L_{1-5}$

Note how eyes move together $R_{1-5}$ $L_{1-5\ AVG}$-AR : 0.2870* (0.9590 to 1.0460)

Note how eyes move together $R_{1-5\ AVG}$-AR : 0.2643* (0.9421 to 1.0548)

A normal person watching TV (naturalistic viewing) has eyes that move together with a conjugacy of 0.0169 (normal range is -.0857 to 0.1598)

A normal person watching TV (naturalistic viewing) has eyes that move together with a conjugacy of 0.0169 (normal range is -.0857 to 0.1598)

A normal person watching TV (naturalistic viewing) has eyes that move together with a conjugacy of 0.0169 (normal range is -.0857 to 0.1598)

A person with a surgically severed IIIrd nerve has a grossly disconjugate gaze that is detectable on naturalistic viewing (watching TV). His conjugacy is 2.2711 (normal range is -.0857 to 0.1598)

FIG. 25A
$L_1$-AR: -1.0785* (0.9590 to 1.0460)

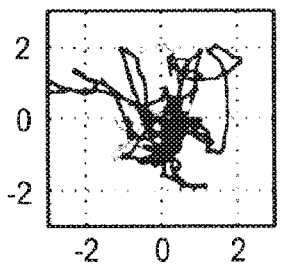

FIG. 25B
$R_1$-AR: 3.0634* (0.9421 to 1.0548)

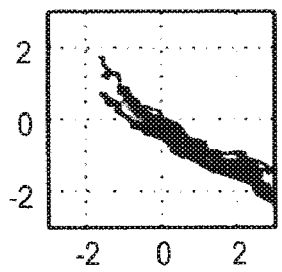

eyes are not moving together

FIG. 25C
$L_2$-AR: NaN (0.9590 to 1.0460)

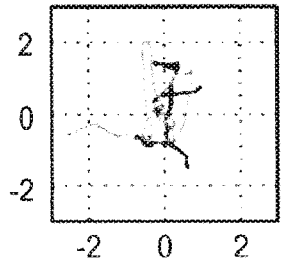

FIG. 25D
$R_2$-AR: NaN (0.9421 to 1.0548)

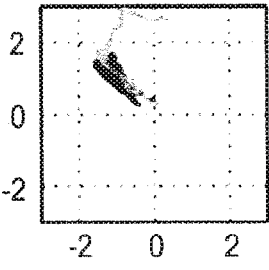

eyes are not moving together

FIG. 25E
$L_3$-AR: NaN (0.9590 to 1.0460)

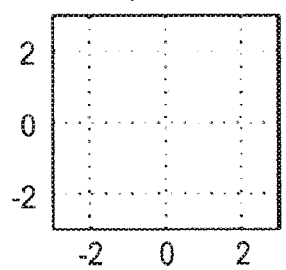

FIG. 25F
$R_3$-AR: NaN (0.9421 to 1.0548)

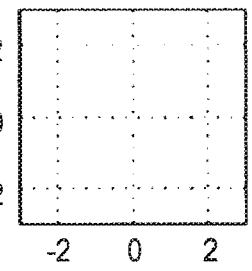

eyes are not moving together

FIG. 25G
$L_4$-AR: NaN (0.9590 to 1.0460)

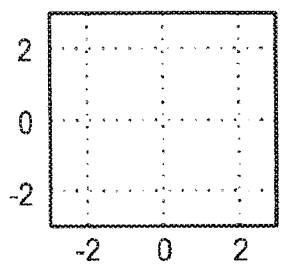

FIG. 25H
$R_4$-AR: NaN (0.9421 to 1.0548)

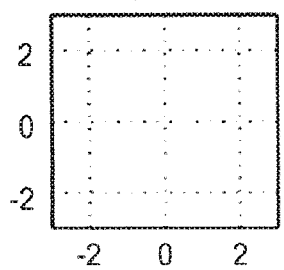

eyes are not moving together

A person with a surgically severed IIIrd nerve has a grossly disconjugate gaze that is detectable on naturalistic viewing (watching TV). His conjugacy is 2.2711 (normal range is -.0857 to 0.1598)

$L_5$-AR : NaN (0.9590 to 1.0460)

eyes are not moving together $R_5$-AR : NaN (0.9421 to 1.0548)

$L_{1-5}$ eyes are not moving together $R_{1-5}$ $L_{1-5\,AVG}$-AR : -1.0785*
(0.9590 to 1.0460)

$R_{1-5\,AVG}$-AR : 3.0634*
(0.9421 to 1.0548)

FIG. 25O

A person with a surgically severed IIIrd nerve has a grossly disconjugate gaze that is detectable on naturalistic viewing (watching TV). His conjugacy is 2.2711 (normal range is -.0857 to 0.1598)

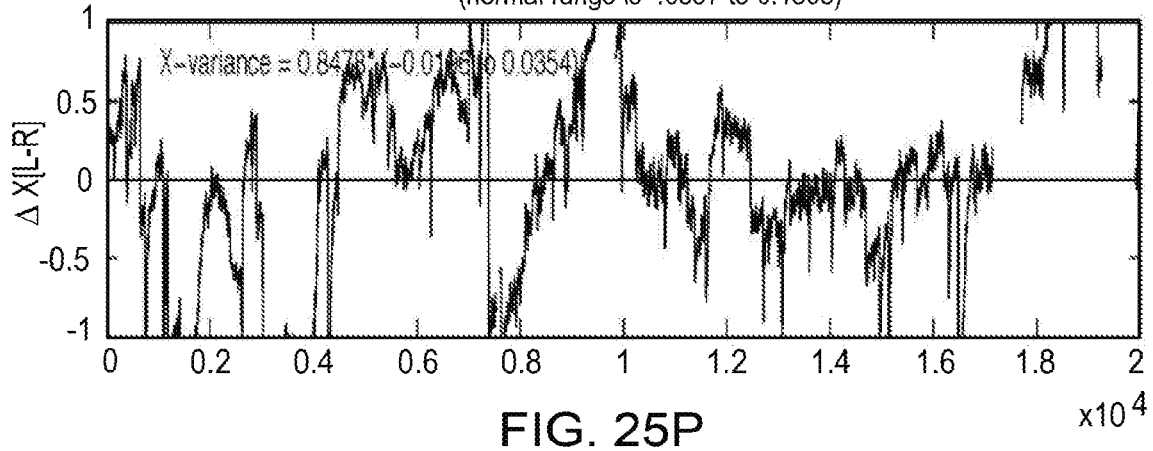

FIG. 25P

A person with a surgically severed IIIrd nerve has a grossly disconjugate gaze that is detectable on naturalistic viewing (watching TV). His conjugacy is 2.2711 (normal range is -.0857 to 0.1598)

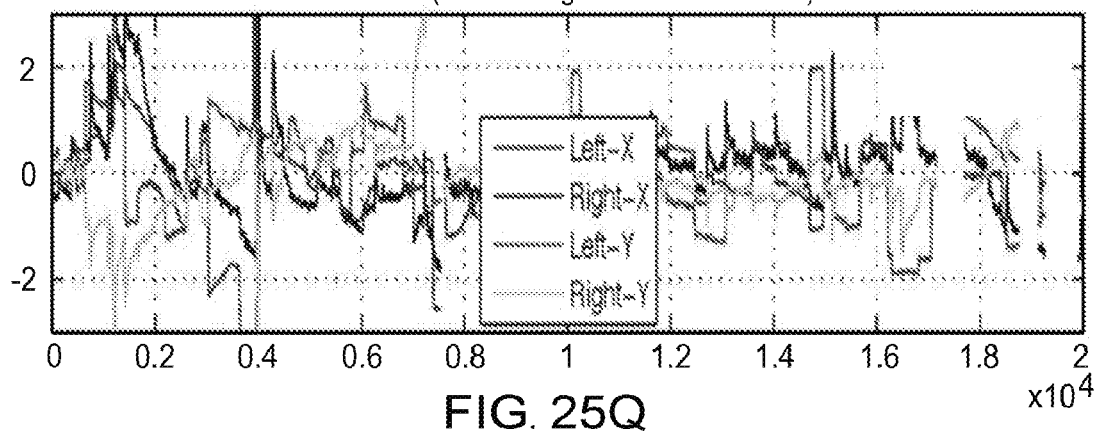

FIG. 25Q

A person with a surgically severed IIIrd nerve has a grossly disconjugate gaze that is detectable on naturalistic viewing (watching TV). His conjugacy is 2.2711 (normal range is -.0857 to 0.1598)

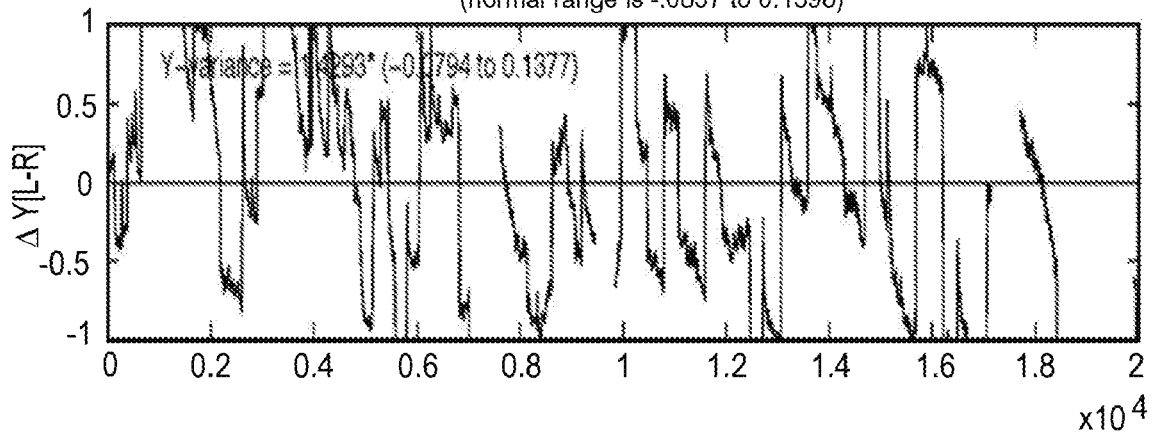

2 days after injury 13 days after injury

Postoperative film

L.Area: 1.3036*  R.Area: 0.8551*  Conj.varXrit: 0.0633*  Post injury day 17
L.varXrit: 0.6270*  R.varXrit: 0.2348*  Conj.varXbot: 0.0354*  Postop day 3
L.varXlef: 0.8659*  R.varXlef: 0.9885*  Conj.varXlef: 0.0825*
L.varTotal: 1.0149*  R.varTotal: 1.0715*  Conj.varYlef: 0.0268*
                                          SCORE: 32

L.Area: 5.561  R.Area: 5.367  Conj.varXrit: 0.009  Post injury day 49
L.varXrit: 0.039  R.varXrit: 0.056  Conj.varXbot: 0.006  Postop day 35
L.varXlef: 0.217*  R.varXlef: 0.436*  Conj.varXlef: 0.057*
L.varTotal: 0.626*  R.varTotal: 0.674  Conj.varYlef: 0.017*
                                       SCORE: 11

FIG. 28B

L.Area: 5.237*
L.varXrit: 0.308*
L.varXlef: 0.026
L.varTotal: 0.610*

R.Area: 4.574
R.varXrit: 1.187*
R.varXlef: 0.012
R.varTotal: 0.710*

Conj.varXrit: 0.123*
Conj.varXbot: 0.032*
Conj.varXlef: 0.049*
Conj.varYlef: 0.004*
SCORE: 18

1 day after fall

FIG. 28C

L.Area: 4.352*
L.varXrit: 0.094*
L.varXlef: 0.126*
L.varTotal: 0.381

R.Area: 4.260
R.varXrit: 0.103
R.varXlef: 0.141*
R.varTotal: 0.385

Conj.varXrit: 0.001
Conj.varXbot: 0.002
Conj.varXlef: 0.001
Conj.varYlef: 0.002
SCORE: 9

12 days after fall

FIG. 28D

L.Area: 5.8606
L.varXrit: 0.0152
L.varXlef: 0.0179
L.varTotal: 0.4937*

R.Area: 5.8270
R.varXrit: 0.0112
R.varXlef: 0.0182
R.varTotal: 0.4940

Conj.varXrit: 0.0014
Conj.varXbot: 0.0048
Conj.varXlef: 0.0030
Conj.varYlef: 0.0036
SCORE: 1

66 days after fall

L.Area: 2.185*   R.Area: 2.842*   Conj.varXrit: 0.020
L.varXrit: 0.004   R.varXrit: 0.008   Conj.varXbot: 0.030*
L.varXlef: 0.004   R.varXlef: 0.004   Conj.varXlef: 0.072*
L.varTotal: 0.185   R.varTotal: 0.202   Conj.varYlef: 0.017
                                        SCORE: 11

L.Area: 5.8519   R.Area: 5.9357   Conj.varXrit: 0.0026
L.varXrit: 0.0149   R.varXrit: 0.0206   Conj.varXbot: 0.0065
L.varXlef: 0.0255   R.varXlef: 0.0125   Conj.varXlef: 0.0106*
L.varTotal: 0.4284   R.varTotal: 0.4241   Conj.varYlef: 0.0673*
                                          SCORE: 6

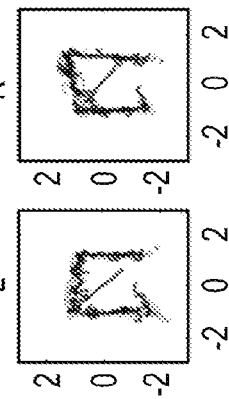

FIG. 31A

L.Area: 5.422
L.varXrit: 0.008
L.varXlef: 0.180*
L.varTotal: 0.627*

R.Area: 4.778
R.varXrit: 0.013
R.varXlef: 0.640*
R.varTotal: 0.715*

Conj.varXrit: 0.010
Conj.varXbot: 0.019*
Conj.varXlef: 0.033*
Conj.varYlef: 0.049*
SCORE: 16

Day of fall

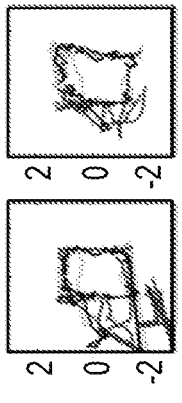

FIG. 31B

L.Area: 4.986*
L.varXrit: 0.050
L.varXlef: 0.065*
L.varTotal: 0.945*

R.Area: 4.981
R.varXrit: 0.053
R.varXlef: 0.025
R.varTotal: 0.657

Conj.varXrit: 0.016
Conj.varXbot: 0.118*
Conj.varXlef: 0.013*
Conj.varYlef: 0.014
SCORE: 10

10 days after fall

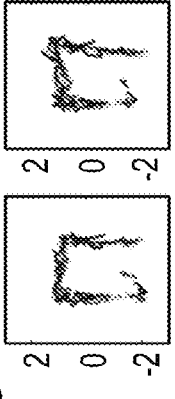

FIG. 31C

L.Area: 6.421*
L.varXrit: 0.008
L.varXlef: 0.012
L.varTotal: 0.631*

R.Area: 5.897
R.varXrit: 0.031
R.varXlef: 0.009
R.varTotal: 0.650

Conj.varXrit: 0.014
Conj.varXbot: 0.013*
Conj.varXlef: 0.001
Conj.varYlef: 0.058*
SCORE: 6

17 Days after fall

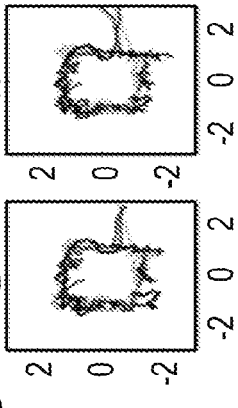

FIG. 31D

L.Area: 5.7853
L.varXrit: 0.0961*
L.varXlef: 0.0228
L.varTotal: 0.5658*

R.Area: 5.7052
R.varXrit: 0.2265*
R.varXlef: 0.0175
R.varTotal: 0.5931

Conj.varXrit: 0.0123
Conj.varXbot: 0.0003
Conj.varXlef: 0.0019
Conj.varYlef: 0.0038*
SCORE: 4

113 Days after fall

METHODS AND KITS FOR ASSESSING NEUROLOGICAL FUNCTION AND LOCALIZING NEUROLOGICAL LESIONS

CROSS-REFERENCE TO RELATED APPLICATIONS

The present application is a continuation of U.S. application Ser. No. 16/322,355, filed Jan. 31, 2019, now U.S. Pat. No. 11,642,071, which is a national stage entry of PCT/US2017/044972, filed Aug. 1, 2017, which claims priority to U.S. Provisional Application Ser. No. 62/369,848, filed Aug. 2, 2016, the disclosures of which are hereby incorporated by reference in their entirety as if fully set forth herein.

FIELD OF THE INVENTION

The present invention relates to methods and kits for assessing physiologic function of the cranial nerves II, III, IV and VI, screening for, diagnosing, and quantitating the extent of elevated intracranial pressure, transtentorial herniation, concussion, normal pressure hydrocephalus, posterior fossa mass effect, optic neuropathy, neurodegenerative diseases, and diagnosing, localizing and monitoring progression of intracranial lesions and disease processes. The present invention also relates to methods and kits for assessing or quantitating conjugacy or disconjugacy of gaze or strabismus and for screening for, diagnosing, and assessing neurological diseases characterized by or featuring the same. In addition, the present invention relates to methods and kits for assessing or quantitating structural and non-structural traumatic brain injury and for screening for, diagnosing, and assessing the same.

BACKGROUND OF THE INVENTION

Eye Movement Tracking

Automated eye movement tracking has been used for marketing and advertising research, the development of assistive devices for immobile individuals, and for video games. Spatial calibration of the device requires the subject to have relatively intact ocular motility that implies function of cranial nerves II (optic), III (oculomotor), IV (trochlear) and VI (abducens) and their associated nuclei as well as sufficient cerebral function to enable cognition and volition for calibration. Calibrated eye movement tracking has been utilized to detect cognitive impairment secondary to axonal shearing after mild traumatic brain injury (Lee, *Brain research.* 2011; 1399:59-65; Contreras et al., *Brain Research* 2011; 1398:55-63 and Maruta et al., *The Journal of Head Trauma Rehabilitation* 2010; 25(4):293-305).

Others have successfully demonstrated the clinical applications of eye movement data (Lee et al., *Brain Research.* 2011; 1399:59-65; Contreras et al., *Brain Research* 2011; 1398:55-63; Maruta et al., *The Journal of Head Trauma Rehabilitation* 2010; 25(4):293-305). Trojano et al., *J Neurol* 2012; (published online; ahead of print) recently described uncalibrated eye movement measurements in a population of minimally conscious and persistently vegetative patients. They report data from 11 healthy control subjects evaluating chronic disorders of consciousness, not acute changes in intracranial pressure. They sample eye movements at 60 Hz rather than 500 Hz, effectively reducing the power of their data 100-fold, and they report differences in on-target and off-target fixations between the groups without spatially calibrated data. Moreover, they use static stimuli moving in a quasi-periodic way.

Elevated Intracranial Pressure

If untreated, acute elevations in intracranial pressure (ICP) due to hydrocephalus, brain injury, stroke, or mass lesions can result in permanent neurologic impairment or death. Hydrocephalus, the most common pediatric neurosurgical condition in the world, has been well studied as a model for understanding the impact of elevated ICP. The visual disturbances and diplopia associated with hydrocephalus were first described by Hippocrates in approximately 400 B.C. (Aronyk, *Neurosurg Clin N Am.* 1993; 4(4):599-609). Papilledema, or swelling of the optic disc, and its association with elevated ICP was described by Albrecht von Graefe in 1860 (Pearce, *European neurology* 2009; 61(4):244-249). In the post-radiographic era, acute and chronic pathology of the optic nerve and disc (cranial nerve II), and of ocular motility (cranial nerves III, IV and VI) are well characterized in hydrocephalic children (Dennis et al., *Arch Neurol.* October 1981; 38(10):607-615; Zeiner et al., *Childs Nerv Syst.* 1985; 1(2):115-122 and Altintas et al., *Graefe's archive for clinical and experimental ophthalmology=Albrecht von Graefes Archiv fur klinische and experimentelle Ophthalmologic.* 2005; 243(12):1213-1217). Visual fields may be impaired in treated hydrocephalus (Zeiner et al., *Childs Nerv Syst.* 1985; 1(2):115-122), and there is increased latency in light-flash evoked responses in acutely hydrocephalic children relative to their post treatment state (Sjostrom et al., *Childs Nerv Syst.* 1995; 11(7): 381-387). Clinically apparent disruption of ocular motility may precede computed tomography (CT) findings in some acute hydrocephalics (Tzekov et al., *Pediatric Neurosurgery* 1991; 17(6):317-320 and Chou et al., *Neurosurgery Clinics of North America* 1999; 10(4):587-608).

Several potential mechanisms may contribute to cranial nerve dysfunction due to hydrocephalus. The optic nerve (II) is most frequently analyzed because it can be visualized directly with ophthalmoscopy, and indirectly with ultrasound. Edema of the optic nerve appears earlier than ocular fundus changes, and resolves after treatment of elevated ICP (Gangemi et al., *Neurochirurgia* 1987; 30(2):53-55). Fluctuating elevated neural pressure leads to impaired axonal transport along the optic nerve after as little as 30 minutes in a rabbit model (Balaratnasingam et al., *Brain Research* 2011; 1417:67-76). Axoplasmic flow stasis and intraneuronal ischemia may occur in the optic nerve exposed to chronically elevated ICP (Lee et al., *Current Neurology and Neuroscience Reports.* Feb. 23, 2012).

At present, the diagnosis of elevated intracranial pressure relies on history, physical exam, radiographic imaging, and possibly direct invasive assessment of the subarachnoid space or structures contiguous with it via cannulated needle tap of a shunt or monitoring device placement. Chemical dilatation of the pupil to assess for papilledema may be unpleasant for the examinee, relies on the experience of the examiner and obfuscates further examination of the pupillary reflex. Papilledema is not always a sensitive marker for hydrocephalus, and in one study was present in as few as 14% of patients with a shunt malfunction (Nazir et al., *J Aapos* 2009; 13(1):63-66) consistent with the relatively short intracranial course of II relative to cranial nerves III and IV. Compartmentalization of subarachnoid spaces is hypothesized to explain why papilledema may be present in a patient without elevated ICP, and not occur in patients with elevated ICP (Killer et al., *Clinical & Experimental Ophthalmology* 2009; 37(5):444-447).

Conjugacy of Eye Movement

It is conceivable that the process of spatial calibration may mask deficits in ocular motility. If there is a persistent and replicable weakness in movement of an eye, the camera will interpret the eye's ability to move in the direction of that weakness as the full potential range of motion in that direction due to the calibration process. In other words if the subject is directed to look at a position but consistently only moves halfway there, the calibration process will account for that when tracking subsequent eye movements and interpret movements to the halfway point as occurring at the full range of normal motion. If during calibration one eye only makes it halfway to the target, but the other eye is fully there, the camera will interpret both eyes as being together when one performs half the eye movement as the other. Thus binocular spatial calibration may preclude detection of disconjugate gaze unless each eye is calibrated separately using a dichoptic apparatus (Schotter, et al., PLoS One, 2012; 7: e35608).

Conjugate gaze is the motion of both eyes in the same direction at the same time. The conjugate gaze is believed to be controlled by the following four different mechanisms: the saccadic system that allows for voluntary direction of the gaze, the pursuit system that allows the subject to follow a moving object, the optokinetic system that restores gaze despite movements of the outside world, and the vestibulo-ocular reflex system (VOR system) that corrects for the movements of the head to preserve the stable visual image of the world.

Disconjugate gaze or strabismus is a failure of the eyes to turn together in the same direction. Normal coordinated movements of the eyes produces conjugate gaze, in which the eyes are aligned for binocular 3-dimensional vision. Misalignment results in loss of this vision. With the visual axis of each eye fixated on a different point, diplopia (or double vision) usually results and may be perceived as a blurred image if the two images are very closely aligned. However, if the image from the weaker eye is suppressed by higher cortical centers, there is only one image with loss of visual acuity (or a blurred image). Pathology usually resides either in the oculomotor muscles or their neuronal pathways including the medial longitudinal fasciculus, the paramedian pontine reticular formation, the medullary reticular formation, the superior colliculus, or the cranial nerves III, IV, or VI or their nuclei.

Assessment of eye movement conjugacy is commonly performed by primary care physicians, neurologists, ophthalmologists, neurosurgeons, emergency medicine doctors, and trauma surgeons to rapidly assess global neurologic functioning. In stable patients, ophthalmologists and neurologists perform more detailed examination to assess the alignment of the eyes such as the cover test and Hirschberg corneal reflex test. Other tests used to assess binocular conjugacy include the Titmus House Fly test, Lang's stereo test, the Hess screen, red-filter test, Maddox rod evaluation and Lancaster red-green test. In young children, who may be less cooperative with an examiner, binocular gaze conjugacy may only be assessable with simpler algorithms, such as following an object moving in a set trajectory (Cavezian, et al., Res Dev Disabil., 2010; 31: 1102-1108). When such tests are performed in conjunction with the remainder of the neurophthalmic and physical evaluation, one can localize neurologic lesions and quantitate ocular motility deficits with great accuracy. Despite this capability, these tests are not used routinely in the emergency setting due to the need for a trained practitioner to administer them, the requirement for sophisticated equipment, and the urgent nature of many neurologic disorders.

Assessment of binocular gaze conjugacy in primates for research purposes is performed with the magnetic search coil technique requiring coils implanted into the bulbar conjunctiva (Schultz, et al., J Neurophysiol., 2013; 109: 518-545). This technique was first described by Fuchs and Robinson in 1966 (Fuchs, et al., J Appl Physiol., 1966; 21: 1068-1070) and can also be performed in humans fitted with sclera search coils designed specifically for tracking eye movements.

Experimentally, spatially calibrated eye movement tracking using the Bouis oculometer (Bach, et al., J Neurosci Methods, 1983; 9: 9-14), which requires that the head is rigidly fixed, shows that healthy seven year old children have increased disconjugacy of eye movement during saccades relative to adults while both perform a reading task (Bucci, et al., Vision Res., 2006; 46: 457-466). Research on disconjugacy during reading can be performed using a dichoptic apparatus in which the individual eyes are spatially calibrated separately and presented with stimuli to assess movements separately for simultaneous comparison to each other (Schotter, et al., PLoS One, 2012; 7: e35608).

Brain Injury

One of the problems associated with the study of outcomes after brain injury, is the heterogeneous nature of such injury in terms of etiology, anatomic sequelae, and physiologic and psychologic impact. The etiology of injury affects the anatomic sequelae and ranges from global mechanisms such as acceleration/deceleration and blast, to potentially more focal mechanisms such as blunt impact and penetrating trauma. Some injury mechanisms result in structural changes to the brain that can be visualized using conventional imaging such as MRI and CT scan, while other injuries appear radiographically normal.

Acceleration/deceleration injury may result in structurally visible coup/contrecoup injuries and less visible diffuse axonal injury (DAI) (Cecil, et al., Journal of Neurosurgery, 1998; 88: 795-801) Acceleration/deceleration is also thought to be one of the potential mechanisms for concussion which is the most common form of civilian radiographically normal brain injury (Bayly, et al., Journal of Neurotrauma, 2005; 22: 845-856; Daneshvar, et al., Physical Medicine and Rehabilitation Clinics of North America, 2011; 22: 683-700). Concussion is brain injury, most often resulting from blunt impact, in the absence of structural abnormality by conventional radiographic imaging such as computed tomography (CT) scan (McCrory, et al., The Physician and Sports Medicine, 2009; 37: 141-159). Concussion may include transient loss or disruption of neurologic function. The term "subconcussion" may be used to describe the sequelae of brain injury in the absence of transient loss or disruption of neurologic function. Both concussion and subconcussion as well as blast injury may be termed "non-structural" brain injury.

Blast injury resembles blunt impact brain injury in that both may be associated with radiographically apparent cerebral edema and intracranial hemorrhage, however with blast injury the edema onset may be more rapid and severe, and there is greater likelihood of clinical vasospasm (Armonda, et al., Neurosurgery, 2006; 59: 1215-1225). Blast injury is very frequently radiographically normal, yet mild or moderate blast injury is strongly associated with post-traumatic stress disorder and other cognitive dysfunctions (Cernak, et al., The Journal of Trauma, 2001; 50: 695-706). The actual cause of blast brain injury is suspected to be multifactorial and often results in DAI (Leung, et al., *Mol Cell Biomech,* 2008; 5: 155-168). A shock wave resulting from pressure changes caused by the explosion impacts both cranial and non-cranial structures (Courtney, et al., *Medical Hypotheses,* 2009; 72: 76-83; Bauman, et al., *Journal of Neurotrauma,* 2009; 26: 841-860). Blast injury affects the brain through several mechanisms: primary brain injury caused by blast-wave induced changes in atmospheric pressure directly impacting the brain; secondary injury resulting from objects put in motion by the blast that impact the head, and tertiary injury resulting from the victim striking the head upon falling or being propelled into a solid object (Warden, *The Journal of Head Trauma Rehabilitation,* 2006; 21: 398-402).

Blunt impact and penetrating trauma can result in both diffuse and focal injury. One mechanism by which focal brain injury leads to neurologic damage is cortical spreading depression (Hartings, et al., *Journal of Neurotrauma,* 2009; 26: 1857-1866), which is currently only thought measurable using invasive means.

Brain injury may be associated with short term sequelae including headaches and memory problems, and longer term problems including dementia, Parkinsonism and motor-neuron disease (Daneshvar, et al., *Physical Medicine and Rehabilitation Clinics of North America,* 2011; 22: 683-700). Both concussion and mild blast injury may be associated with post-traumatic stress disorder and cognitive impairment (Taber, et al., *The Journal of Neuropsychiatry and Clinical Neurosciences,* 2006; 18: 141-145). Clinical tests for concussion show poor test reliability (Broglio, et al., *Journal of Athletic Training,* 2007; 42: 509-514) and thus concussion remains a diagnosis that is difficult to treat because it is difficult to detect. Traumatic brain injury can impact eye movement through a multitude of mechanisms including direct compression of cranial nerves, trauma to cranial nerves, injury to cranial nerve nuclei and supranuclear impacts.

Many cases of trauma result in elevated intracranial pressure. If untreated, acute elevations in intracranial pressure (ICP) due to brain injury can result in permanent neurologic impairment or death. Double vision and other ocular disturbances associated with elevated ICP were first described by Hippocrates in approximately 400 B.C. (Aronyk, *Neurosurgery Clinics of North America,* 1993; 4: 599-609). Papilledema, and its association with elevated ICP was described by Albrecht von Graefe in 1860 (Pearce, *European Neurology,* 2009; 61: 224-249). In the post-radiographic era, acute and chronic pathology of the optic nerve and disc, and of ocular motility are well characterized in people with elevated ICP (Dennis, et al., *Archives of Neurology,* 1981; 38: 607-615; Zeiner, et al., *Child's Nerv. Syst.,* 1985; 1: 115-122; Altintas, et al., *Graefe's Archive for Clinical and Experimental Ophthalmology,* 2005; 243: 1213-1217). Clinically apparent disruption of ocular motility may precede computed tomography (CT) findings in some subjects with acutely elevated ICP (Tzekov, et al., *Pediatric Neurosurgery,* 1991; 17: 317-320; Chou, et al., *Neurosurgery Clinics of North America,* 1999; 10: 587-608).

Several potential mechanisms may contribute to cranial nerve dysfunction due to elevated intracranial pressure. The IIIrd nerve (oculomotor) may be directly compressed by the medial aspect of the temporal lobe with frontal or temporal mass lesions, or diffuse supratentorial mass effect. The VIth nerve (abducens) is anatomically vulnerable to infratentorial mass effect at the prepontine cistern and to hydrocephalus from stretch as it traverses the tentorial edge.

Elevated intracranial pressure slows axoplasmic transport along cranial nerves (Balarratnasingam, et al., *Brain Research,* 2011; 1417: 67-76). The optic nerve (II) is most frequently analyzed because it can be visualized directly with ophthalmoscopy, and indirectly with ultrasound. Edema of the optic nerve appears earlier than ocular fundus changes, and resolves after treatment of elevated ICP Gangemi, et al., *Neurochirurgia,* 1987; 30: 53-55). Fluctuating elevated neural pressure leads to impaired axonal transport along the optic nerve after as little as 30 minutes in a rabbit model (Balarratnasingam, et al., *Brain Research,* 2011; 1417: 67-76). Axoplasmic flow stasis and intraneuronal ischemia may occur in the optic nerve exposed to chronically elevated ICP (Lee, et al., *Current Neurology and Neuroscience Reports,* 2012). Among the nerves impacting ocular motility, the trochlear nerve (IV), followed by oculomotor (III) and then abducens (VI), has the greatest length of exposure to the subarachnoid space with the narrowest diameter, and thus may be most vulnerable to a pressure induced palsy (Hanson, et al., *Neurology,* 2004; 62: 33-36; Adler, et al., *Journal of Neurosurgery,* 2002; 96: 1103-1113). The optic nerve (II) has approximately the same length of exposure as the abducens (Murali, et al., in *Head Injury* (ed. Paul Cooper and John Golfinos) (McGraw-Hill, 2000)), and thus papilledema, or swelling of the optic disc apparent on ophthalmoscopic examination may be a relatively late indicator of elevated ICP (Killer, et al., *Clinical & Experimental Ophthalmology,* 2009; 37: 444-447; Nazir, et al., *J Aapos,* 2009; 13: 62-66). Papilledema is not always a sensitive marker for hydrocephalus leading to elevated ICP, and in one study was present in as few as 14% of patients with a shunt malfunction (Nazir, et al., *J Aapos,* 2009; 13: 62-66) consistent with the relatively short intracranial course of II compared to cranial nerves III and IV. Compartmentalization of subarachnoid spaces is hypothesized to explain why papilledema may be present in a patient without elevated ICP, and not occur in patients with elevated ICP (Killer, et al., *Clinical & Experimental Ophthalmology,* 2009; 37: 444-447).

All publications, patent applications, patents and other reference material mentioned are incorporated by reference in their entirety, for instance, Patent Cooperation Treaty Application No. PCT/US2013/033672 filed Mar. 25, 2013, and U.S. provisional application 61/881,014, filed Sep. 23, 2013. In addition, the materials, methods and examples are only illustrative and are not intended to be limiting. The citation of references herein is not to be construed as an admission that the references are prior art to the present invention.

SUMMARY OF THE INVENTION

In a first aspect, the invention provides methods for localizing a central nervous system lesion in a subject by
 a) Tracking eye movement of both eyes of the subject;
 b) Analyzing eye movement of both eyes of the subject;
 c) Comparing eye movement of a first eye of the subject to eye movement of a second eye of the subject;
 d) Identifying the subject as having eye movement of a first eye that is significantly different from eye movement of a second eye; and
 e) Localizing the central nervous system lesion.

The lesion may feature increased intracranial pressure, and the lesion may be, for instance, subsequent to a trauma, a cerebrovascular accident (CVA), an aneurysm or other vascular lesion, a tumor whether malignant or benign, an infectious process, an inflammatory disease, a disruption of venous drainage, a pseudotumor, neurodegenerative disease, hydrocephalus or idiopathic. Localizing the central nervous system lesion may be performed, for instance, by determining the side of the brain that is experiencing increased intracranial pressure. The side of the brain that is experiencing increased intracranial pressure may be determined, for instance, by determining eye movement on that side of the brain that is altered compared to the other side or that is altered compared to that subject's baseline eye movement or to a control subject's eye movement.

In a second aspect, the invention provides methods for diagnosing a central nervous system lesion in a subject by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

The lesion may feature increased intracranial pressure, and the lesion may be, for instance, subsequent to a trauma, a cerebrovascular accident (CVA), an aneurysm or other vascular lesion, a tumor whether malignant or benign, an infectious process, an inflammatory disease, a disruption of venous drainage, a pseudotumor, hydrocephalus or idiopathic.

In a third aspect, the invention provides methods for assessing and quantitating central nervous system integrity in a subject by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

In a fourth aspect, the invention provides methods for detecting or screening for reduced or impaired cranial nerve function or conduction in a subject by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

The cranial nerve may be, for instance, one or more of II, III, IV or VI. The reduced or impaired cranial nerve function or conduction may be unilateral or bilateral and may be caused all or in part by increased intracranial pressure, and it may be caused all or in part by a localized or diffuse lesion or disease process. The reduced function of the cranial nerve may be due to pathology impacting the nerve itself, its associated nucleus or supranuclear inputs including, for instance, lesions affecting the cerebral cortex.

In a fifth aspect, the invention provides methods for detecting, diagnosing or screening for increased intracranial pressure in a subject by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

The increased intracranial pressure may be, for instance, 10%, 20%, 30%, 50%, 100%, 200%, 300% or more greater than normal.

In a sixth aspect, the invention provides methods for detecting, diagnosing, monitoring progression of or screening for a disease or condition featuring increased intracranial pressure by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

The disease or condition featuring increased intracranial pressure may be, for instance, a trauma, cerebrovascular accident (CVA), an aneurysm or other vascular lesion, a tumor whether malignant or benign, an infectious process, an inflammatory disease, a disruption of venous drainage, a pseudotumor, hydrocephalus or idiopathic.

In a seventh aspect, the invention provides methods for detecting, diagnosing or screening for concussion by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

In a eighth aspect, the invention provides methods for detecting, diagnosing or screening for transtentorial herniation by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

In a ninth aspect, the invention provides methods for quantifying the severity of normal pressure hydrocephalus, detecting or screening for shunt malfunction or optimizing valve pressure for treating normal pressure hydrocephalus by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

In a tenth aspect, the invention provides methods for detecting or evaluating posterior fossa mass effect by
   a) Tracking eye movement of both eyes of the subject;
   b) Analyzing eye movement of both eyes of the subject;
   c) Comparing eye movement of a first eye of the subject to eye movement of a second eye of the subject; and
   d) Identifying the subject as having eye movement of a first eye that is significantly different from eye movement of a second eye.

In an eleventh aspect, the invention provides methods for detecting, screening for or diagnosing a disorder that impedes conductance through the optic disc or optic nerve by
   a) Tracking eye movement of both eyes of the subject;
   b) Analyzing eye movement of both eyes of the subject;

c) Comparing eye movement of a first eye of the subject to eye movement of a second eye of the subject; and
d) Identifying the subject as having eye movement of a first eye that is significantly different from eye movement of a second eye.

In a twelfth aspect, the invention provides methods for quantitating the extent of impairment of the entire central nervous system by
a) Tracking eye movement of both eyes of the subject;
b) Analyzing eye movement of both eyes of the subject;
c) Comparing eye movement of a first eye of the subject to eye movement of a second eye of the subject; and
d) Identifying the subject as having eye movement of a first eye that is significantly different from eye movement of a second eye.

The integrity of the central nervous system may be impaired by, for instance, trauma, stroke, a neurodegenerative disease, inflammation, an infectious process, a neoplastic process, vascular disease, an autoimmune disease, a genetic disorder or other causes. This aspect of the invention provides methods for quantitating the extent of global CNS impairment. This aspect of the invention takes advantage of the fact that more that 55% of the brain contributes to vision and visual acuity.

In a thirteenth aspect the invention provides methods for quantitating or assessing cognitive integrity by
a) Tracking eye movement of both eyes of the subject;
b) Analyzing eye movement of both eyes of the subject;
c) Comparing eye movement of a first eye of the subject to eye movement of a second eye of the subject; and
d) Identifying the subject as having eye movement of a first eye that is significantly different from eye movement of a second eye.

In a fourteenth aspect, the invention provides a kit useful for detecting or screening for reduced or impaired cranial nerve function or conduction, useful for detecting, diagnosing or screening for increased intracranial pressure, or useful for detecting, diagnosing, monitoring progression of or screening for a disease or condition featuring increased intracranial pressure containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a fifteenth aspect, the invention provides methods for assessing conjugacy or disconjugacy of eye movement in a subject by
a) Tracking eye movement of both eyes of the subject;
b) Analyzing eye movement of both eyes of the subject;
c) Comparing the x or y Cartesian coordinates at any time point for the eye movement of a first eye of the subject to the respective x or y Cartesian coordinates at the time point for the eye movement of a second eye of the subject;
d) Providing a sum of the differences between all of the x or y coordinates of the first eye compared to the second eye over the time tested or providing a sum of the differences in x or y coordinates of the first eye compared to the second eye over the time tested or both; and, optionally
e) Providing a total sum of the differences between the x or y coordinates of the first eye compared to the second eye over the time tested.

In a sixteenth aspect, the invention provides methods for diagnosing a disease characterized by or featuring disconjugate gaze or strabismus in a subject by
a) Tracking eye movement of both eyes of the subject;
b) Analyzing eye movement of both eyes of the subject;
c) Comparing the x or y Cartesian coordinates at any time point for the eye movement of a first eye of the subject to the respective x or y Cartesian coordinates at the time point for the eye movement of a second eye of the subject;
d) Providing a sum of the differences between the x or y coordinates of the first eye compared to the second eye over the time tested or providing a sum of the differences in the x or y coordinates of the first eye compared to the second eye over the time tested or both; and, optionally
e) Providing a total sum of the differences between the x or y coordinates of the first eye compared to the second eye over the time tested.

In some instances, the disease may be one of trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. The disease may also be an ophthalmologic disease such as conjunctivitis, ophthalmoplegia, ocular injury or other diseases. In some instances, the subject suffering from the disease may have a total sum of the differences between the x or y coordinates of the first eye compared to the second eye over the time tested that is 10%, 20%, 30%, 40%, 50%, 60%, 70%, 80%, 90%, 100%, 150%, 200%, or two, three, four, five, six, eight, ten or more times greater than the total sum of the differences between the x or y coordinates of the first eye compared to the second eye over the time tested in a healthy control or in a reference value based upon one or more healthy controls or based upon the subject at a time before the disease.

In a seventeenth aspect, the invention provides methods for assessing and quantitating central nervous system integrity in a subject by
a) Tracking eye movement of both eyes of the subject;
b) Analyzing eye movement of both eyes of the subject;
c) Comparing the x or y Cartesian coordinates at any time point for the eye movement of a first eye of the subject to the respective x or y Cartesian coordinates at the time point for the eye movement of a second eye of the subject;
d) Providing a sum of the differences between all of the x or y coordinates of the first eye compared to the second eye over the time tested or providing a sum of the differences in the x or y coordinates of the first eye compared to the second eye over the time tested or both; and, optionally
e) Providing a total sum of the differences between the x or y coordinates of the first eye compared to the second eye over the time tested.

In a eighteenth aspect, the invention provides methods for detecting, monitoring progression of or screening for a disease or condition characterized by disconjugate gaze or strabismus by
a) Tracking eye movement of both eyes of the subject;
b) Analyzing eye movement of both eyes of the subject;
c) Comparing the x or y Cartesian coordinates at any time point for the eye movement of a first eye of the subject to the respective x or y Cartesian coordinates at the time point for the eye movement of a second eye of the subject;

d) Providing a sum of the differences between the x or y coordinates of the first eye compared to the second eye over the time tested or providing a sum of the differences in y coordinates of the first eye compared to the second eye over the time tested or both; and, optionally e) Providing a total sum of the differences between the x or y coordinates of the first eye compared to the second eye over the time tested.

In some instances, the disease may be one of trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. The disease may also be an ophthalmologic disease such as conjunctivitis, ophthalmoplegia, ocular injury or other diseases. In some instances, the subject suffering from the disease may have a total sum of the differences between the x or y coordinates of the first eye compared to the second eye over the time tested that is 10%, 20%, 30%, 40%, 50%, 60%, 70%, 80%, 90%, 100%, 150%, 200%, or two, three, four, five, six, eight, ten or more times greater than the total sum of the differences between the x or y coordinates of the first eye compared to the second eye over the time tested in a healthy control or in a reference value based upon one or more healthy controls or based upon the subject at a time before the disease.

In a nineteenth aspect, the invention provides methods for quantitating the extent of disconjugate gaze or strabismus by
  a) Tracking eye movement of both eyes of the subject;
  b) Analyzing eye movement of both eyes of the subject;
  c) Comparing the x or y Cartesian coordinates at any time point for the eye movement of a first eye of the subject to the respective x or y Cartesian coordinates at the time point for the eye movement of a second eye of the subject;
  d) Providing a sum of the differences between the x or y coordinates of the first eye compared to the second eye over the time tested or providing a sum of the differences in the x or y coordinates of the first eye compared to the second eye over the time tested or both; and, optionally
  e) Providing a total sum of the differences between the x or y coordinates of the first eye compared to the second eye over the time tested.

In a twentieth aspect, the invention provides a kit useful for detecting, screening for or quantitating disconjugate gaze or strabismus, useful for diagnosing a disease characterized by disconjugate gaze or strabismus in a subject, useful for detecting, monitoring progression of or screening for a disease or condition characterized by disconjugate gaze or strabismus in a subject or useful for quantitating the extent of disconjugate gaze or strabismus, containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a twenty first aspect, the invention provides methods for assessing or quantitating structural and non-structural traumatic brain injury by
  a) Tracking eye movement of at least one eye of the subject;
  b) Analyzing eye movement of at least one eye of the subject;
  c) Comparing eye movement of at least one eye of the subject to a normal or mean eye movement; and, optionally
  d) Calculating a standard deviation or p value for eye movement of at least one eye of the subject as compared to the normal or mean eye movement.

In some instances, eye movement of both eyes of the subject are tracked and analyzed. In some instances, the x or y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of the other eye of the subject or may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x or y cartesian coordinates of pupil position, normalizing the raw x or y Cartesian coordinates, and sorting the data by eye.

The method may also feature calculating individual metrics, such as, for instance, segment mean, segment median, and segment variance. The method may also feature calculating specific metrics such as, for example, $$L.\text{varYtop} = \text{Var}(\bar{y}_{1,average\ k=1:5,1}) \quad (13)$$

$$R.\text{varYtop} = \text{Var}(\bar{y}_{2,average\ k=1:5,1}) \quad (14)$$

$$L.\text{varXrit} = \text{Var}(\bar{x}_{1,average\ k=1:5,2}) \quad (15)$$

$$R.\text{varXrit} = \text{Var}(\bar{x}_{2,average\ k=1:5,2}) \quad (16)$$

$$L.\text{varYbot} = \text{Var}(\bar{y}_{1,average\ k=1:5,3}) \quad (17)$$

$$R.\text{varYbot} = \text{Var}(\bar{y}_{2,average\ k=1:5,3}) \quad (18)$$

$$L.\text{varXlef} = \text{Var}(\bar{x}_{1,average\ k=1:5,4}) \quad (19)$$

$$R.\text{varXlef} = \text{Var}(\bar{x}_{2,average\ k=1:5,4}) \quad (20)$$

$$L.\text{varTotal} = \text{Average}(\text{Var}(\bar{x}_{1,average\ k=1:5}) + \text{Var}(\bar{y}_{1,average\ k=1:5})) \quad (21)$$

$$R.\text{varTotal} = \text{Average}(\text{Var}(\bar{y}_{2,average\ k=1:5}) + \text{Var}(\bar{y}_{2,average\ k=1:5})) \quad (22)$$

or segment standard deviation and segment skew such as, for instance, $$L.\text{SkewTop} = \text{Skew}(\bar{y}_{1,average\ k=1:5,1}) \quad (27)$$

$$R.\text{SkewTop} = \text{Skew}(\bar{y}_{2,average\ k=1:5,1}) \quad (28)$$

$$L.\text{SkewRit} = \text{Skew}(\bar{x}_{1,average\ k=1:5,2}) \quad (29)$$

$$R.\text{SkewRit} = \text{Skew}(\bar{x}_{2,average\ k=1:5,2}) \quad (30)$$

$$L.\text{SkewBot} = \text{Skew}(\bar{y}_{1,average\ k=1:5,3}) \quad (31)$$

$$R.\text{SkewBot} = \text{Skew}(\bar{y}_{2,average\ k=1:5,3}) \quad (32)$$

$$L.\text{SkewLef} = \text{Skew}(\bar{x}_{1,\text{average } k=1:5,4}) \quad (33)$$

$$R.\text{SkewLef} = \text{Skew}(\bar{x}_{2,\text{average } k=1:5,4}) \quad (34)$$

or segment normalized skew, such as, for instance, $$\text{SkewNorm}(\bar{x}_{j,k,l}) = \frac{\text{Skew}(\bar{x}_{j,k,l})}{\sigma_{\bar{x}_{j,k,l}}}, \quad (35)$$

$$\text{SkewNorm}(\bar{y}_{j,k,l}) = \frac{\text{Skew}(\bar{y}_{j,k,l})}{\sigma_{\bar{y}_{j,k,l}}}. \quad (36)$$

$$L.\text{SkewTopNorm} = \text{SkewNorm}(\bar{y}_{1,\text{average } k=1:5,1}) \quad (37)$$

$$R.\text{SkewTopNorm} = \text{SkewNorm}(\bar{y}_{2,\text{average } k=1:5,1}) \quad (38)$$

$$L.\text{SkewRitNorm} = \text{SkewNorm}(\bar{x}_{1,\text{average } k=1:5,2}) \quad (39)$$

$$R.\text{SkewRitNorm} = \text{SkewNorm}(\bar{x}_{1,\text{average } k=1:5,2}) \quad (40)$$

$$L.\text{SkewBotNorm} = \text{SkewNorm}(\bar{y}_{1,\text{average } k=1:5,3}) \quad (41)$$

$$R.\text{SkewBotNorm} = \text{SkewNorm}(\bar{y}_{2,\text{average } k=1:5,3}) \quad (42)$$

$$L.\text{SkewLefNorm} = \text{SkewNorm}(\bar{x}_{1,\text{average } k=1:5,4}) \quad (43)$$

$$R.\text{SkewLefNorm} = \text{SkewNorm}(\bar{x}_{2,\text{average } k=1:5,4}) \quad (44)$$

The method may also feature calculating box height, box width, box area, or box aspect ratio.

Box Height $$\text{BoxHeight}_{j,k} = \bar{y}_{j,k,1} - \bar{y}_{j,k,3} \quad (45)$$

Box Width $$\text{BoxWidth}_{j,k} = \bar{x}_{j,k,2} - \bar{x}_{j,k,4} \quad (46)$$

Box Aspect Ratio $$\text{AspectRatio}_{j,k} = \frac{\text{BoxHeight}_{j,k}}{\text{BoxWidth}_{j,k}} \quad (47)$$

Box Area $$\text{BoxArea}_{j,k} = \text{BoxHeight}_{j,k} \times \text{BoxWidth}_{j,k} \quad (48)$$

The method may also feature calculating conjugacy of eye movement or variance from perfect conjugacy of eye movement, such as, for example, box area $$\text{Conj varXtop} = \frac{\Sigma(\hat{x}_1)^2 - 0}{\Sigma \hat{x}_1}, \quad (57)$$

$$\text{Conj varXrit} = \frac{\Sigma(\hat{x}_2)^2 - 0}{\Sigma \hat{x}_2}, \quad (58)$$

$$\text{Conj varXbot} = \frac{\Sigma(\hat{x}_3)^2 - 0}{\Sigma \hat{x}_3}, \quad (59)$$

$$\text{Conj varXlef} = \frac{\Sigma(\hat{x}_4)^2 - 0}{\Sigma \hat{x}_4}, \quad (60)$$

$$\text{Conj varYtop} = \frac{\Sigma(\hat{y}_1)^2 - 0}{\Sigma \hat{y}_1}, \quad (61)$$

$$\text{Conj varYrit} = \frac{\Sigma(\hat{y}_2)^2 - 0}{\Sigma \hat{y}_2}, \quad (62)$$

$$\text{Conj varYbot} = \frac{\Sigma(\hat{y}_3)^2 - 0}{\Sigma \hat{y}_3}, \quad (63)$$

-continued $$\text{Conj varYlef} = \frac{\Sigma(\hat{y}_4)^2 - 0}{\Sigma \hat{y}_4}, \quad (64)$$

$$\text{Conj CorrXYtop} = \frac{\Sigma \hat{x}_1 \hat{y}_1}{\Sigma \hat{x}_1 - 1}, \quad (65)$$

$$\text{Conj CorrXYrit} = \frac{\Sigma \hat{x}_2 \hat{y}_2}{\Sigma \hat{x}_2 - 1}, \quad (66)$$

$$\text{Conj CorrXYbot} = \frac{\Sigma \hat{x}_3 \hat{y}_3}{\Sigma \hat{x}_3 - 1}, \quad (67)$$

$$\text{Conj CorrXYlef} = \frac{\Sigma \hat{x}_4 \hat{y}_4}{\Sigma \hat{x}_4 - 1}, \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing structural or non-structural traumatic brain injury such as, for instance, a concussion, subconcussion or blast injury. In some instances, two, three, four, five, six, seven, eight, nine, ten or more metrics may be observed or determined.

A standard deviation or p value of 0.25, 0.3, 0.4, 0.5, 0.75. 0.8, 0.9, 1.0, 1.5, 2.0, 2.5 or more may reflect that a subject has structural or non-structural traumatic brain injury such as, for instance, a concussion, subconcussion or blast injury. As such, the methods described herein may be used to detect concussion, subconcussion and blast injury and assess or determine the severity of the same.

In a twenty second aspect, the invention provides methods for diagnosing a disease characterized by or featuring structural and non-structural traumatic brain injury in a subject by
a) Tracking eye movement of at least one eye of the subject;
b) Analyzing eye movement of at least one eye of the subject;
c) Comparing eye movement of at least one eye of the subject to a normal or mean eye movement; and, optionally
d) Calculating a standard deviation or p value for eye movement of at least one eye of the subject.

In some instances, eye movement of both eyes of the subject are tracked and analyzed. In some instances, x or y coordinates of eye position for one or both eyes of a subject are collected for at least about 100, 500, 1,000, 5,000, 10,000, 50,000, 100,000, 200,000 or more eye positions. In some instances, the eye position is effectively the pupil position. In some instances the eye movement is tracked for about 30, 60, 90, 100, 120, 150, 180, 200, 220, 240, 270, 300, 360 or more seconds.

The comparing eye movement of at least one eye of the subject to a normal or mean eye movement may feature comparing eye movement of at least one eye of the subject to the eye movement of the other eye of the subject or may feature comparing eye movement of at least one eye of the subject to the eye movement of an eye of one or more other subjects or controls. In some instances, the comparing eye movement of at least one eye of the subject to a normal or mean eye movement may feature comparing the eye movement of both eyes of the subject to the eye movement of one or both eyes of one or more other subjects or controls.

In some instances, the method may feature collecting raw x or y cartesian coordinates of pupil position, normalizing the raw x or y cartesian coordinates, and sorting the data by eye.

The method may also feature calculating individual metrics, such as, for instance, segment mean, segment median, and segment variance. The method may also feature calculating specific metrics such as, for example, $$L.\text{varYtop} = \text{Var}(\bar{y}_{1, average\ k=1:5,1}) \quad (13)$$

$$R.\text{varYtop} = \text{Var}(\bar{y}_{2, average\ k=1:5,1}) \quad (14)$$

$$L.\text{varXrit} = \text{Var}(\bar{x}_{1, average\ k=1:5,2}) \quad (15)$$

$$R.\text{varXrit} = \text{Var}(\bar{x}_{2, average\ k=1:5,2}) \quad (16)$$

$$L.\text{varYbot} = \text{Var}(\bar{y}_{1, average\ k=1:5,3}) \quad (17)$$

$$R.\text{varYbot} = \text{Var}(\bar{y}_{2, average\ k=1:5,3}) \quad (18)$$

$$L.\text{varXlef} = \text{Var}(\bar{x}_{1, average\ k=1:5,4}) \quad (19)$$

$$R.\text{varXlef} = \text{Var}(\bar{x}_{2, average\ k=1:5,4}) \quad (20)$$

$$L.\text{varTotal} = \text{Average}(\text{Var}(\bar{x}_{2, average\ k=1:5}) + \text{Var}(\bar{y}_{1, average\ k=1:5})) \quad (21)$$

$$R.\text{varTotal} = \text{Average}(\text{Var}(\bar{x}_{2, average\ k=1:5}) + \text{Var}(\bar{y}_{2, average\ k=1:5})) \quad (22)$$

or segment standard deviation and segment skew such as, for instance, $$L.\text{SkewTop} = \text{Skew}(\bar{y}_{1, average\ k=1:5,1}) \quad (27)$$

$$R.\text{SkewTop} = \text{Skew}(\bar{y}_{2, average\ k=1:5,1}) \quad (28)$$

$$L.\text{SkewRit} = \text{Skew}(\bar{x}_{1, average\ k=1:5,2}) \quad (29)$$

$$R.\text{SkewRit} = \text{Skew}(\bar{x}_{2, average\ k=1:5,2}) \quad (30)$$

$$L.\text{SkewBot} = \text{Skew}(\bar{y}_{1, average\ k=1:5,3}) \quad (31)$$

$$R.\text{SkewBot} = \text{Skew}(\bar{y}_{2, average\ k=1:5,3}) \quad (32)$$

$$L.\text{SkewLef} = \text{Skew}(\bar{x}_{1, average\ k=1:5,4}) \quad (33)$$

$$R.\text{SkewLef} = \text{Skew}(\bar{x}_{2, average\ k=1:5,4}) \quad (34)$$

or segment normalized skew, such as, for instance, $$SkewNorm(\bar{x}_{j,k,l}) = \frac{\text{Skew}(\bar{x}_{j,k,l})}{\sigma_{\bar{x}_{j,k,l}}}, \quad (35)$$

$$SkewNorm(\bar{y}_{j,k,l}) = \frac{\text{Skew}(\bar{y}_{j,k,l})}{\sigma_{\bar{y}_{j,k,l}}}. \quad (36)$$

$$L.\text{SkewTopNorm} = SkewNorm(\bar{y}_{1, average\ k=1:5,1}) \quad (37)$$

$$R.\text{SkewTopNorm} = SkewNorm(\bar{y}_{2, average\ k=1:5,1}) \quad (38)$$

$$L.\text{SkewRitNorm} = SkewNorm(\bar{x}_{1, average\ k=1:5,2}) \quad (39)$$

$$R.\text{SkewRitNorm} = SkewNorm(\bar{x}_{2, average\ k=1:5,2}) \quad (40)$$

$$L.\text{SkewBotNorm} = SkewNorm(\bar{y}_{1, average\ k=1:5,3}) \quad (41)$$

$$R.\text{SkewBotNorm} = SkewNorm(\bar{y}_{2, average\ k=1:5,3}) \quad (42)$$

$$L.\text{SkewLefNorm} = SkewNorm(\bar{x}_{1, average\ k=1:5,4}) \quad (43)$$

$$R.\text{SkewLefNorm} = SkewNorm(\bar{x}_{2, average\ k=1:5,4}) \quad (44)$$

The method may also feature calculating box height, box width, box area, or box aspect ratio.

Box Height $$\text{BoxHeight}_{j,k} = \bar{y}_{j,k,1} - \bar{y}_{j,k,3} \quad (45)$$

Box Width $$\text{BoxWidth}_{j,k} = \bar{x}_{j,k,2} - \bar{x}_{j,k,4} \quad (45)$$

Box Aspect Ratio $$AspectRatio_{j,k} = \frac{BoxHeight_{j,k}}{BoxWidth_{j,k}} \quad (47)$$

Box Area $$\text{BoxArea}_{j,k} = \text{BoxHeight}_{j,k} \times \text{BoxWidth}_{j,k} \quad (48)$$

The method may also feature calculating conjugacy of eye movement or variance from perfect conjugacy of eye movement, such as, for example, $$Conj\ varXtop = \frac{\Sigma(\hat{x}_1)^2 - 0}{\Sigma \hat{x}_1}, \quad (57)$$

$$Conj\ varXrit = \frac{\Sigma(\hat{x}_2)^2 - 0}{\Sigma \hat{x}_2}, \quad (58)$$

$$Conj\ varXbot = \frac{\Sigma(\hat{x}_3)^2 - 0}{\Sigma \hat{x}_3}, \quad (59)$$

$$Conj\ varXlef = \frac{\Sigma(\hat{x}_4)^2 - 0}{\Sigma \hat{x}_4}, \quad (60)$$

$$Conj\ varYtop = \frac{\Sigma(\hat{y}_1)^2 - 0}{\Sigma \hat{y}_1}, \quad (61)$$

$$Conj\ varYrit = \frac{\Sigma(\hat{y}_2)^2 - 0}{\Sigma \hat{y}_2}, \quad (62)$$

$$Conj\ varYbot = \frac{\Sigma(\hat{y}_3)^2 - 0}{\Sigma \hat{y}_3}, \quad (63)$$

$$Conj\ varYlef = \frac{\Sigma(\hat{y}_4)^2 - 0}{\Sigma \hat{y}_4}, \quad (64)$$

$$Conj\ CorrXYtop = \frac{\Sigma \hat{x}_1 \hat{y}_1}{\Sigma \hat{x}_1 - 1}, \quad (65)$$

$$Conj\ CorrXYrit = \frac{\Sigma \hat{x}_2 \hat{y}_2}{\Sigma \hat{x}_2 - 1} \quad (66)$$

$$Conj\ CorrXYbot = \frac{\Sigma \hat{x}_3 \hat{y}_3}{\Sigma \hat{x}_3 - 1} \quad (67)$$

$$Conj\ CorrXYlef = \frac{\Sigma \hat{x}_4 \hat{y}_4}{\Sigma \hat{x}_4 - 1} \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing structural or non-structural traumatic brain injury such as, for instance, a concussion, subconcussion or blast injury. In some instances, two, three, four, five, six, seven, eight, nine, ten or more metrics may be observed or determined.

A standard deviation or p value of 0.25, 0.3, 0.4, 0.5, 0.75, 0.8, 0.9, 1.0, 1.5, 2.0, 2.5 or more may reflect that a subject has structural or non-structural traumatic brain injury such as, for instance, a concussion, subconcussion or blast injury. As such, the methods described herein may be used to detect concussion, subconcussion or blast injury and assess or determine the severity of the same. In some instances the eye movement is tracked for about 30, 60, 90, 100, 120, 150, 180, 200, 220, 240, 270, 300, 360 or more seconds.

In a twenty third aspect, the invention provides methods for assessing or quantitating structural and non-structural traumatic brain injury or diagnosing a disease characterized by or featuring structural and non-structural traumatic brain injury in a subject by
  a) Tracking eye movement of at least one eye of the subject;
  b) collecting raw x or y cartesian coordinates of pupil position;
  c) normalizing the raw x or y Cartesian coordinates; and
  d) calculating one or more individual metric.

In some instances, eye movement of both eyes of the subject are tracked and analyzed. In some instances, x or y coordinates of eye position for one or both eyes of a subject are collected for at least about 100, 500, 1,000, 5,000, 10,000, 50,000, 100,000, 200,000 or more eye positions. In instances where the eye movement of both eyes are tracked, the method may additionally feature sorting the data by eye.

The one or more individual metric may be any one of $$L.\text{varYtop} = \text{Var}(\bar{y}_{1,average\ k=1:5,1}) \tag{13}$$

$$R.\text{varYtop} = \text{Var}(\bar{y}_{2,average\ k=1:5,1}) \tag{14}$$

$$L.\text{varXrit} = \text{Var}(\bar{x}_{1,average\ k=1:5,2}) \tag{15}$$

$$R.\text{varXrit} = \text{Var}(\bar{x}_{2,average\ k=1:5,2}) \tag{16}$$

$$L.\text{varYbot} = \text{Var}(\bar{y}_{1,average\ k=1:5,3}) \tag{17}$$

$$R.\text{varYbot} = \text{Var}(\bar{y}_{2,average\ k=1:5,3}) \tag{18}$$

$$L.\text{varXlef} = \text{Var}(\bar{x}_{1,average\ k=1:5,4}) \tag{19}$$

$$R.\text{varXlef} = \text{Var}(\bar{x}_{2,average\ k=1:5,4}) \tag{20}$$

$$L.\text{varTotal} = \text{Average}(\text{Var}(\bar{x}_{1,average\ k=1:5}) + \text{Var}(\bar{y}_{1,average\ k=1:5})) \tag{21}$$

$$R.\text{varTotal} = \text{Average}(\text{Var}(\bar{x}_{2,average\ k=1:5}) + \text{Var}(\bar{y}_{2,average\ k=1:5})) \tag{22}$$

or segment standard deviation and segment skew such as, for instance, $$L.\text{SkewTop} = \text{Skew}(\bar{y}_{1,average\ k=1:5,1}) \tag{27}$$

$$R.\text{SkewTop} = \text{Skew}(\bar{y}_{2,average\ k=1:5,1}) \tag{28}$$

$$L.\text{SkewRit} = \text{Skew}(\bar{x}_{1,average\ k=1:5,2}) \tag{29}$$

$$R.\text{SkewRit} = \text{Skew}(\bar{x}_{2,average\ k=1:5,2}) \tag{30}$$

$$L.\text{SkewBot} = \text{Skew}(\bar{y}_{1,average\ k=1:5,3}) \tag{31}$$

$$R.\text{SkewBot} = \text{Skew}((\bar{y}_{2,average\ k=1:5,3}) \tag{32}$$

$$L.\text{SkewLef} = \text{Skew}(\bar{x}_{1,average\ k=1:5,4}) \tag{33}$$

$$R.\text{SkewLef} = \text{Skew}(\bar{x}_{2,average\ k=1:5,4}) \tag{34}$$

or segment normalized skew, such as, for instance, $$\text{SkewNorm}(\bar{x}_{j,k,l}) = \frac{\text{Skew}(\bar{x}_{j,k,l})}{\sigma_{\bar{x}_{j,k,l}}}, \tag{35}$$

$$\text{SkewNorm}(\bar{y}_{j,k,l}) = \frac{\text{Skew}(\bar{y}_{j,k,l})}{\sigma_{\bar{y}_{j,k,l}}}. \tag{36}$$

$$L.\text{SkewTopNorm} = \text{SkewNorm}(\bar{y}_{1,average\ k=1:5,1}) \tag{37}$$

$$R.\text{SkewTopNorm} = \text{SkewNorm}(\bar{y}_{2,average\ k=1:5,1}) \tag{38}$$

$$L.\text{SkewRitNorm} = \text{SkewNorm}(\bar{x}_{1,average\ k=1:5,2}) \tag{39}$$

$$R.\text{SkewRitNorm} = \text{SkewNorm}(\bar{x}_{2,average\ k=1:5,2}) \tag{40}$$

$$L.\text{SkewBotNorm} = \text{SkewNorm}(\bar{y}_{1,average\ k=1:5,3}) \tag{41}$$

$$R.\text{SkewBotNorm} = \text{SkewNorm}(\bar{y}_{2,average\ k=1:5,3}) \tag{42}$$

$$L.\text{SkewLefNorm} = \text{SkewNorm}(\bar{x}_{1,average\ k=1:5,4}) \tag{43}$$

$$R.\text{SkewLefNorm} = \text{SkewNorm}(\bar{x}_{2,average\ k=1:5,4}) \tag{44}$$

The method may also feature calculating box height, box width, box area, or box aspect ratio.

Box Height $$\text{BoxHeight}_{j,k} = \bar{y}_{j,k,1} - \bar{y}_{j,k,3} \tag{45}$$

Box Width $$\text{BoxWidth}_{j,k} = \bar{x}_{j,k,2} - \bar{x}_{j,k,4} \tag{46}$$

Box Aspect Ratio $$\text{AspectRatio}_{j,k} = \frac{\text{BoxHeight}_{j,k}}{\text{BoxWidth}_{j,k}} \tag{47}$$

Box Area $$\text{BoxArea}_{j,k} = \text{BoxHeight}_{j,k} \times \text{BoxWidth}_{j,k} \tag{48}$$

The method may also feature calculating conjugacy of eye movement or variance from perfect conjugacy of eye movement, such as, for example, $$\text{Conj varXtop} = \frac{\Sigma(\hat{x}_1)^2 - 0}{\Sigma \hat{x}_1}, \tag{57}$$

$$\text{Conj varXrit} = \frac{\Sigma(\hat{x}_2)^2 - 0}{\Sigma \hat{x}_2}, \tag{58}$$

$$\text{Conj varXbot} = \frac{\Sigma(\hat{x}_3)^2 - 0}{\Sigma \hat{x}_3}, \tag{59}$$

$$\text{Conj varXlef} = \frac{\Sigma(\hat{x}_4)^2 - 0}{\Sigma \hat{x}_4}, \tag{60}$$

$$\text{Conj varYtop} = \frac{\Sigma(\hat{y}_1)^2 - 0}{\Sigma \hat{y}_1}, \tag{61}$$

$$\text{Conj varYrit} = \frac{\Sigma(\hat{y}_2)^2 - 0}{\Sigma \hat{y}_2}, \tag{62}$$

$$\text{Conj varYbot} = \frac{\Sigma(\hat{y}_3)^2 - 0}{\Sigma \hat{y}_3}, \tag{63}$$

$$\text{Conj varYlef} = \frac{\Sigma(\hat{y}_4)^2 - 0}{\Sigma \hat{y}_4}, \tag{64}$$

$$\text{Conj CorrXYtop} = \frac{\Sigma \hat{x}_1 \hat{y}_1}{\Sigma \hat{x}_1 - 1}, \tag{65}$$

$$\text{Conj } CorrXYrit = \frac{\Sigma \hat{x}_2 \hat{y}_2}{\Sigma \hat{x}_2 - 1} \quad (66)$$

$$\text{Conj } CorrXYbot = \frac{\Sigma \hat{x}_3 \hat{y}_3}{\Sigma \hat{x}_3 - 1} \quad (67)$$

$$\text{Conj } CorrXYlef = \frac{\Sigma \hat{x}_4 \hat{y}_4}{\Sigma \hat{x}_4 - 1} \quad (68)$$

or variance x ratio top/bottom (conjugacy), variance y ratio top/bottom (conjugacy), variance x ratio left/right (conjugacy), or variance y ratio left/right (conjugacy).

In some instances, one or more of the L height, L width, L area, L varXrit, L varXlef, L varTotal, R height, R width, R area, R varYtop, R varXrit, R varXlef, R varTotal, Conj varX, Conj varXrit, Conj varXbot, Conj varXlef and Conj varYlef may be especially useful for demonstrating or detecting or assessing structural or non-structural traumatic brain injury such as, for instance, a concussion, subconcussion or blast injury. In some instances, two, three, four, five, six, seven, eight, nine, ten or more metrics may be observed or determined.

A standard deviation or p value of 0.25, 0.3, 0.4, 0.5, 0.75, 0.8, 0.9, 1.0, 1.5, 2.0, 2.5 or more may reflect that a subject has structural or non-structural traumatic brain injury such as, for instance, a concussion, subconcussion or blast injury. As such, the methods described herein may be used to detect concussion and assess or determine the severity of the same.

In a twenty fourth aspect, the invention provides a kit useful for detecting, screening for or quantitating structural and non-structural traumatic brain injury in a subject, containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a twenty fifth aspect, the invention provides a computer system. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

Eye Movement Tracking Device

According to the methods described, tracking eye movement may be performed using any suitable device such as, for example, an Eyelink® 1000 binocular eye tracker (500 Hz sampling, SR Research). The eye tracking movement samples may be obtained at any suitable frequency, such as for instance, 10 Hz to 10,000 Hz or more. The subject may be positioned an appropriate distance from the device, such as, for example, 10, 20, 30, 40, 50, 55, 60, 70, 80, 90 cm or more, or even a meter or more from the device screen. In some instances, the subject's head may be stabilized, such as, for instance by using a chinrest or similar stabilizing mechanism. The subject may be seated or reclining. Preferably, the presentation monitor of the device is adjusted so as to substantially match the subject's gaze direction. The tracking eye movement may be performed for a total of, for example, 30, 60, 90, 120, 150, 180, 200, 220, 240, 270, 300, 330, 360, 400, 450, 500 seconds or more, or for 5, 10, 15, 20, 25, 30, 45, 60, or 90 minutes or more. As such, according to the methods provided, 1,000, 5,000, 10,000, 20,000, 25,000, 50,000, 75,000, 100,000, 150,000, 200,000, 250,000, 300,000 or more samples of eye position may be obtained. Similarly, the tracking eye movement may be performed using a video oculography device, such as, for instance, goggles, or using a web-cam based tracking system.

According to the methods described, analyzing eye movement may be performed by any suitable means. In some instances, a stimulus and an analysis stream are provided that allows interpreting raw eye position data. In some instances, an algorithm may be provided for looking at pupil position directly thereby yielding information about ocular motility. Preferably, a device is adapted into a novel mobile system that may analyze eye movement close in time or substantially concurrent to the eye movement itself.

Tracking Eye Movement in Response to a Moving or Visual Stimulus

According to the methods described, eye movement may be tracked in response to a visual stimulus. In some instances, the visual stimulus may be, for instance, a video such as a music video that may move, for instance clockwise, along the outer edge, of a computer monitor. In some instances, such a video may be provided starting at the upper or lower, left or right hand corners, of a screen. The visual stimulus such as a video, e.g. a music video, may be provided in a substantially square aperture with an area of approximately 10, 12, 14, 16, 18, 20, 25, or degrees, for example, approximately 1/10, 1/8, 1/6, 1/5, 1/4, 1/3, 1/2 of the size of the screen or so. The visual stimulus, such as, for example a music video, may play substantially continuously during the eye movement tracking, and it may in some instances move across the screen at a relatively or substantially constant speed. For instance, such a visual stimulus, for instance, a music video may cover each edge of a monitor in about 2, 5, 10, 15, 20, 30, 45 or 60 seconds or so. Therefore, in some instances, a full cycle may take, for instance, 10, 20, 30, 40, 50, 60, 75, 100, 120, 150, 180 seconds or so. Multiple cycles of such a visual stimulus, for instance a music video may be played, for instance, one, two, three, four, five, six, seven, eight, nine, ten, twelve, fifteen, twenty or more full cycles. As such, the visual stimulus may be provided, the eye movement may be tracked, in effect, in some instances the video may be played for a total of, for example, 30, 60, 90, 120, 150, 180, 200, 220, 240, 270, 300, 330, 360, 400, 450, 500 seconds or more. In instances where the visual stimulus is in the form of a video, a countdown video may be played in the starting position for, for instance, 5, 10, 15, 20, 25, or 30 seconds or more before beginning the visual stimulus, e.g. video, to provide subjects sufficient time to orient to the visual stimulus. Likewise, the visual stimulus, for instance a video, may be continued for an addition 2, 5, 10, 15, 20, 30, 45 or 60 seconds or so after the eye movement tracking is performed to reduce or substantially avoid boundary effects. The same result could be obtained by having the visual stimulus moving over any distance x relative to any amount of time t. The ideal stimulus would move however in both the x and y Cartesian planes to optimize the assessment capability of the method.

According to the methods described, comparing eye movement of a first eye of the subject to eye movement of a second eye of the subject, may be performed by analyzing data. Data from the tracking eye movement may provide an indication of whether an individual subject's gaze is conjugate (eyes are moving together) versus disconjugate. Comparing eye movement of a first eye of the subject to eye movement of a second eye of the subject may feature generating scatterplots. Comparing eye movement of a first eye of the subject to eye movement of a second eye of the subject, may feature plotting the horizontal eye position along one axis and vertical eye position along an orthogonal axis. Such comparing eye movement of the subject to a control, or comparing eye movement of a first eye of the subject to eye movement of a second eye of the subject, may feature generating, plotting pairs of (x,y) values, for instance, 50,000, 100,000 or more pairs of values (x,y). Such pairs of values (x,y) may be plotted representing, for instance, the two components of the instantaneous angle of pupil reflection (horizontal, vertical) over a period of time, for instance, 100 or 200 seconds or more.

As such, comparing eye movement of a first eye of the subject to eye movement of a second eye of the subject, may feature generating figures substantially resembling boxes that reflect the trajectory traveled by the visual stimulation, such as when it moves across a screen. In healthy controls, these figures substantially resembling boxes may look like, for instance, substantially equilateral rectangles or squares, reflecting the trajectory traveled by the visual stimulus across a screen. In instances of neurological damage or increased intracranial pressure, such figures may not substantially resemble a box, a rectangle or a square. In fact, in some instances, the cranial nerve having reduced or impaired function or conduction may be identified. In some instances, the figures generated that reflect the trajectory traveled by the visual stimulation may demonstrate abnormal distribution of or absence of normal plotting pairs in particular areas. Increased variability along the y-axis may for example reflect cranial nerve II dysfunction. Decreased variability along the y-axis, or decreased height to width ratio may reflect CN III dysfunction. Increased height to width ratio may reflect CN IV or VI dysfunction. The height of the box may be mathematically determined by assessing the position of the pupil as the video traverses the top and bottom of the presented visual stimulus. This "actual" height may be different from the perceived height mathematically, since the perceived height can represent aberrant pupillary motion due to the patient's ocular motility dysfunction. The integrity of the box walls may also be indicative of other types of dysfunction. Both cranial nerve palsies and mass effect may cause defects in box trajectory. Supratentorial mass lesions and CN III defects may impact the top and/or bottom of the box. Infratentorial mass lesions or CN VI palsies may impact the sides of the box. For instance, in the case of the left eye, the upper left quadrant of the figure may reflect activity, function or conduction of cranial nerves III and VI, the lower left quadrant of the figure may reflect activity, function or conduction of cranial nerves III and IV, while the upper right quadrant and the lower right quadrants may reflect activity, function or conduction of cranial nerve III. In the case of the right eye, the upper and lower left quadrants of the figure may reflect activity, function or conduction of cranial nerve III, the lower right quadrant of the figure may reflect activity, function or conduction of cranial nerve III, while the upper right quadrant and the lower right quadrant may reflect activity, function or conduction of cranial nerves IV and VI.

Comparing eye movement of a first eye of the subject to eye movement of a second eye of the subject, may feature determining the distribution of certain measurements in the control population and comparing the subject with these control distributions. In such instances, visual stimulus trajectory may be divided into four time components, for instance, two, three, four, five, six or more repetitions of the first few, for instance, 2, 5, 10, 15, 20 or so seconds of each rotation cycle. In such instances, comparing eye movement of the subject to a control may feature evaluating such variables as the relative variance in each arm, and the relative integrity of each arm.

Comparing eye movement of the subject to a control, or comparing eye movement of a first eye of the subject to eye movement of a second eye of the subject, may also feature measuring the integrity of each subject's values. In instances featuring generating figures substantially resembling boxes that reflect the trajectory traveled by the visual stimulation, such as when it moves across a screen, the sides or arms of the figures (e.g. the top of the box and the bottom of the box) may be z-scored using the mean and standard deviation calculated from the control population. The resulting score may indicate how different the subject's values are compared with the control values, such as, for instance, in units of standard deviations.

According to the methods described, identifying the subject as having eye movement significantly different from the control, or identifying the subject as having eye movement of a first eye that is significantly different from eye movement of a second eye, may be performed using a z-score. Because 95% of all values in a normal distribution lie within two standard deviations of the mean, a z-score of 2 may be used as a significance threshold. Subjects with z-scores above, for instance, 2 in either or both, or 1, 2, 3, or 4 sides or arms of the figures may be judged to have significant disturbances of ocular motility.

Identifying the subject as having eye movement significantly different from the control, or identifying the subject as having eye movement of a first eye that is significantly different from eye movement of a second eye, may feature determining relative variance. In some instances, multiple such as 1,000, 2,000, 3,000, 5,000, 10,000, 20,000 or more point distributions may be generated by, for instance, taking multiple samples from a multiple number of values randomly chosen with replacement from the multiple control values. For each subject, the relative variance in either or both, or 1, 2, 3, or 4 sides or arms of the figures may be compared respectively with the corresponding control distribution, and the percent of the control distribution with variance below that of the test value may be determined. A p-value of 0.05 a widely accepted measure of statistical significance corresponds to 95% of control values falling below the test value. In such instances, subjects with variance higher than 95% of the values in the control distributions may be determined to have significant disturbances of ocular motility. The video may also move in other trajectories not resembling a rectangle, such as a triangle, circle or linear or nonlinear trajectories. As long as the trajectories can be resolved into vectors along Cartesian coordinates (horizontal vertical or x,y) the same principles apply. In short, any trajectory (e.g. any shape, or line, or curve, etc.) studied over time may provide information about Central Nervous System function or dysfunction.

Comparing the movement of one eye of a subject to the other eye of a subject may be performed by comparing the x or y Cartesian coordinates at any time point t, for example, by subtracting the x coordinate of the left eye from the x coordinate of the right eye or vice versa, or by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested may be totaled to obtain a measure of total disconjugacy of gaze, which is a surrogate marker for central nervous system integrity. In such a way, it is possible to quantitate the extent of central nervous system (CNS) integrity by quantitating the extent of disconjugate gaze. A comparative study of horizontal, vertical, and total disconjugacy using different kinds of visual stimuli demonstrated that horizontal axis conjugacy was greater than or equal to vertical axis conjugacy. As such, either x or y conjugacy may be used singly to assess the extent of disconjugate gaze.

Eye Movement Tracking without a Moving or Visual Stimulus

Eye movement may also be tracked without using a moving stimulus. It is possible to assess conjugacy without having the stimulus move at all, but by assessing the x or y coordinates over times during naturalistic viewing. For example, eye movement may be tracked during television watching or live viewing of an environment without a specific viewing apparatus such as a monitor or screen.

According to the methods described, comparing the x or y Cartesian coordinates at any time point for the eye movement of a first eye of the subject to the respective x or y Cartesian coordinates at any time point for the eye movement of a second eye of the subject, may be performed by analyzing data. Data from the tracking eye movement may provide an indication of whether an individual subject's gaze is conjugate (eyes are moving together) versus disconjugate. Comparing the x or y Cartesian coordinates at any time point for the eye movement of a first eye of the subject to the respective x or y Cartesian coordinates at any time point for the eye movement of a second eye of the subject, may feature generating scatterplots. Comparing the x or y Cartesian coordinates at any time point for the eye movement of a first eye of the subject to the respective x or y Cartesian coordinates at any time point for the eye movement of a second eye of the subject, may feature plotting the difference between the horizontal eye positions along one axis and time along an orthogonal axis, or the difference between the vertical eye positions along one axis and time along an orthogonal axis. Such comparing the x or y Cartesian coordinates at any time point for the eye movement of a first eye of the subject to the respective x or y Cartesian coordinates at any time point for the eye movement of a second eye of the subject, may feature generating, plotting pairs of (x or y) values, for instance, 25,000, 50,000, 75,000, 100,000, 150,000 or more pairs of values (x or y). Such pairs of values (x or y) may be plotted representing, for instance, the two components of the instantaneous angle of pupil reflection (horizontal, vertical) over a period of time, for instance, 100 or 200 or 250 or 300 seconds or more.

As such, comparing the x or y Cartesian coordinates at any time point for the eye movement of a first eye of the subject to the respective x or y Cartesian coordinates at the time point for the eye movement of a second eye of the subject, may allow generating plots assessing conjugacy of eye movements over time.

Comparing the x or y Cartesian coordinates at any time point for the eye movement of a first eye of the subject to the respective x or y Cartesian coordinates at the time point for the eye movement of a second eye of the subject, may feature determining the distribution of certain measurements in the control population and comparing the subject with these control distributions. In such instances, visual stimulus trajectory may be divided into four time components, for instance, two, three, four, five, six or more repetitions of the first few, for instance, 2, 5, 10, 15, 20 or so seconds of each rotation cycle. In such instances, comparing the x or y Cartesian coordinates at any time point for the eye movement of a first eye of the subject to the respective x or y Cartesian coordinates at any time point for the eye movement of a second eye of the subject may feature evaluating such variables as the relative variance in each arm, and the relative integrity of each arm.

Comparing the x or y Cartesian coordinates at any time point for the eye movement of a first eye of the subject to the respective x or y Cartesian coordinates at the time point for the eye movement of a second eye of the subject may be performed by comparing the x or y Cartesian coordinates at any time point t, for example, by subtracting the x coordinate of the left eye from the x coordinate of the right eye or vice versa, or by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested may be totaled to obtain a measure of total disconjugacy of gaze, which may be a surrogate marker for central nervous system integrity. In such a way, it is possible to quantitate the extent of central nervous system (CNS) integrity by quantitating the extent of disconjugate gaze. A comparative study of horizontal, vertical, and total disconjugacy using different kinds of visual stimuli demonstrated that horizontal axis conjugacy was greater than or equal to vertical axis conjugacy. As such, either x or y conjugacy may be used singly to assess the extent of disconjugate gaze.

Providing a sum of the differences between all of the x coordinates of the first eye compared to the second eye over the time tested or providing a sum of the differences in y coordinates of the first eye compared to the second eye over the time tested or both may be performed subsequent to comparing the x or y Cartesian coordinates at the time point t. For example, by subtracting the x coordinate of the left eye from the x coordinate of the right eye or vice versa. Also, by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested can be summed to obtain a measure of total disconjugacy of gaze, or as an average of five eyebox trajectory cycles formulaically represented as follows:

$$X_{Avg,ik} = \frac{\sum_{j=1}^{5} X_{i,j,k}}{5}, \text{ for all } i = 1:N, k = 1:2,$$

where $X_{ijk}$ refers to the x-coordinate of the pupil, and k refers to the left or right eye of a subject. In cases where a subject's data was missing at any given time point in the five cycles, the denominator of the equation was the number of cycles where the data was present. The difference in the x or y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero vertical or horizontal pupil position difference between each eye. The variance for either horizontal (x) or vertical (substitute y for x) movement may be computed as follows:

$$\text{Var}_x = \frac{1}{N} \sum_{i=1}^{N} \left([(X]_{Avg,i1} - X_{Avg,i2}) - 0\right)^2$$

Providing a total sum of the differences between both x and y coordinates of the first eye compared to the second eye over the time tested may be performed by calculating the total variance in both the horizontal and vertical planes between the first and the second eyes. The total variance may be computed as follows:

$$\text{Var}_{Tot} = \text{Var}_x + \text{Var}_y.$$

In some instances, the $\text{Var}_x$ or the $\text{Var}_y$ or both, calculated as described herein, may be 0.05, 0.07, 0.1, 0.15, 0.20, 0.25, 0.30, 0.40, 0.50, 0.60, 0.75, 0.90, 1.0, 1.10, 1.25, 1.50, 1.75, or 2.0 or more. Similarly, in some instances, the $\text{Var}_{Tot}$ calculated as described herein, may be 0.1, 0.15, 0.20, 0.25, 0.30, 0.40, 0.50, 0.60, 0.75, 0.90, 1.0, 1.10, 1.25, 1.50, 1.75, 2.0, 2.50, 3.0 or 4.0 or more, in subjects having a neurological disease or condition characterized by or featuring disconjugacy of gaze or strabismus.

BRIEF DESCRIPTION OF THE FIGURES

FIG. 1A and FIG. 2B) demonstrates that as the aperture containing a video moves in a rectangular pattern, different nerves move the pupils. FIG. 1A demonstrates movement of the left eye, and FIG. 1B demonstrates movement of the right eye. Cranial nerve III moves the pupil up and down. Cranial nerve VI moves it laterally. This data was obtained on a monocular eye tracker with sequential tracking of each eye. The video goes around five times with each tracking recorded in a separate color (red, green, cyan, magenta, blue).

FIG. 2A and FIG. 2B represent the eye-box trajectory of a normal subject tracked binocularly (FIG. 2A, left eye; FIG. 2B right eye). Note that the eyes appear to be moving relatively the same, with some differences. FIGS. 2C and 2D are time-course representations (FIG. 2C, left eye; FIG. 2D right eye), in which the x-axis is the Cartesian coordinate of the eye position and the y-axis is time.

FIGS. 3A and 3B represent eye-box trajectories (FIG. 3A, left eye; FIG. 3B right eye). FIGS. 3C and 3D are time-course representations (FIG. 3C, left eye; FIG. 3D right eye), in which the x-axis is the Cartesian coordinate of the eye position and the y-axis is time. The eyes are not as conjugate as the subject in FIGS. 2A-D.

FIGS. 4A-D demonstrate the binocular eye movement tracking of a subject with a mild IIIrd nerve palsy recruited from the ophthalmology clinic. The subject reported increased lacrimation but no diplopia. FIGS. 4A and 4B represent eye-box trajectories (FIG. 4A, left eye; FIG. 4B right eye). FIGS. 4C and 4D are time-course representations (FIG. 4C, left eye; FIG. 4D right eye), in which the x-axis is the Cartesian coordinate of the eye position and the y-axis is time. The eyes are not as conjugate as the subject in FIGS. 2A-D in the x-plane but are completely disconjugate in the y-plane. The eye tracking anomaly appears contralateral to the ocular pathology.

FIGS. 5A and 5B represent eye-box trajectories (FIG. 5A, left eye; FIG. 5B right eye). FIGS. 5C and 5D are time-course representations (FIG. 5C, left eye; FIG. 5D right eye), in which the x-axis is the Cartesian coordinate of the eye position and the y-axis is time. The subject was unable to watch much of the video, but for the little that he did watch, his y, more so than his x, was disconjugate. His head computed tomography scan did not show any evidence of acute structural injury. The eye tracking is thus showing concussion (radiographically silent) brain injury.

FIG. 6B y-plane). A subject with third nerve palsy shows only diconjugacy in the y-plane (FIG. 6E, x-plane; FIG. 6F y-plane). A subject with structural brain injury has disconjugacy in both x and y planes (FIG. 6G, x-plane; FIG. 6H y-plane), as does a concussion subject (FIG. 6C, x-plane; FIG. 6D y-plane).

FIGS. 15A-F provide a representation of the binocular eye movement tracking of a normal subject. FIGS. 15A-B provide box plots of eye movement in response to a moving stimulus. The aspect ratio for each eye is provided. FIGS. 15C-D provide graphic representation of the eye movement tracking for each eye over time. FIGS. 15E-F provide graphical representation of the variance in x-axis movement between the left and right eye and the variance in y-axis movement between the left and right eye. Total variance of x and y coordinates of eye movement over time is provided.

FIGS. 16A-L provide a representation of the eye movement of a patient with conjunctivitis due to a blocked lacrimal duct. FIGS. 16A-B provide box plots of eye movement. The aspect ratio for each eye is provided. FIGS. 16C-D provide graphic representation of the eye movement tracking for each eye over time. FIGS. 16E-F provide graphical representation of the variance in x-axis movement between the left and right eye and the variance in y-axis movement between the left and right eye. Total variance of x and y coordinates of eye movement over time is provided. The same information is provided after resolution of symptoms. FIGS. 16G-H provide box plots of eye movement. The aspect ratio for each eye is provided. FIGS. 16I-J provide graphic representation of the eye movement tracking for each eye over time. FIGS. 16K-L provide graphical representation of the variance in x-axis movement between the left and right eye and the variance in y-axis movement between the left and right eye. Total variance of x and y coordinates of eye movement over time is provided. Total variance (disconjugacy) is markedly improved after resolution of symptoms.

FIGS. 17A-F provide a representation of the eye movement of a 9 year old patient with a history of lymphoma and exotrophic strabismus. FIGS. 17A-B provide box plots of eye movement. The aspect ratio for each eye is provided. FIGS. 17C-D provide graphic representation of the eye movement tracking for each eye over time. FIGS. 17E-F provide graphical representation of the variance in x-axis movement between the left and right eye and the variance in y-axis movement between the left and right eye. Total variance of x and y coordinates of eye movement over time is provided.

FIGS. 18A-L provide a representation of the eye movement of subjects with cranial nerve palsies. FIGS. 18A-B provide box plots of eye movement in a patient having a cranial nerve IV palsy. The aspect ratio for each eye is provided. FIGS. 18C-D provide graphical representation of the variance in x-axis movement between the left and right eye and the variance in y-axis movement between the left and right eye. Total variance of x and y coordinates of eye movement over time is provided. FIGS. 18E-F provide box plots of eye movement in a patient having a diabetic cranial nerve III palsy. The aspect ratio for each eye is provided. FIGS. 18G-H provide graphical representation of variance over time. FIGS. 18I-J provide box plots of eye movement in a patient having a post-surgical cranial nerve VI palsy. The aspect ratio for each eye is provided. FIGS. 18K-L provide graphical representation of variance over time.

FIGS. 19A-L provide a representation of the eye movement of a 35 year old patient with a ruptured cerebral aneurysm resulting in subarachnoid hemorrhage. FIGS. 19A=B provide box plots of eye movement. The aspect ratio for each eye is provided. FIGS. 19C-D provide graphic representation of the eye movement tracking for each eye over time. FIGS. 19E-F provide graphical representation of variance over time. The total variance of x and y coordinates is provided. FIGS. 19G-H provide box plots of eye movement in the patient 6 days later, after embolization of the aneurysm. The aspect ratio for each eye is provided. FIGS. 19I-J provide graphic representation of the eye movement tracking for each eye over time. FIGS. 19K-L provide graphical representation of the variance in x-axis movement between the left and right eye and the variance in y-axis movement between the left and right eye. Total variance of x and y coordinates of eye movement over time is provided.

FIGS. 20A-F provide a representation of the eye movement of a brain injured subject. FIGS. 20A=B provide box plots of eye movement. The aspect ratio for each eye is provided. FIGS. 20C-D provide graphic representation of the eye movement tracking for each eye over time. FIGS. 20E-F provide graphical representation of the variance in x-axis movement between the left and right eye and the variance in y-axis movement between the left and right eye. Total variance of x and y coordinates of eye movement over time is provided.

FIGS. 21A-F provide a representation of the eye movement of a subject suffering a concussion. FIGS. 21A=B provide box plots of eye movement. The aspect ratio for each eye is provided. FIGS. 21C-D provide graphic representation of the eye movement tracking for each eye over time. FIGS. 21E-F provide graphical representation of variance over time. The total variance of x and y coordinates is provided.

FIG. 22A-L provide a representation of the eye movement of a subject suffering a concussion. FIGS. 22A-B provide box plots of eye movement on the day of the fall resulting in the concussion. The aspect ratio for each eye is provided. FIGS. 22C-D provide graphic representation of the eye movement tracking for each eye over time. Disconjugacy is calculated or quantified. FIGS. 22E-F provide box plots of eye movement ten days after the fall resulting in the concussion. The aspect ratio for each eye is provided. FIGS. 22G-H provide graphical representation of the variance in x-axis movement between the left and right eye and the variance in y-axis movement between the left and right eye. Total variance of x and y coordinates of eye movement over time is provided. Disconjugacy is calculated or quantified. FIGS. 22I-J provide box plots of eye movement three weeks after the fall resulting in the concussion. The aspect ratio for each eye is provided. FIGS. 22K-L provide graphic representation of the eye movement tracking for each eye over time. Disconjugacy is calculated or quantified.

FIGS. 23A-N provide box plots of eye movement tracking (left and right eyes). The aspect ratio for each eye is provided. FIGS. 23O-Q provide graphic representation of the eye movement tracking for each eye over time demonstrating the variance in x-axis movement between the left and right eye and the variance in y-axis movement between the left and right eye.

FIGS. 24A-N provide box plots of eye movement tracking (left and right eyes). The aspect ratio for each eye is provided. FIGS. 24O-Q provide graphic representation of the eye movement tracking for each eye over time demonstrating the variance in x-axis movement between the left and right eye and the variance in y-axis movement between the left and right eye. Conjugacy is calculated or quantified at 0.0169.

FIGS. 25A-Q provide a representation of the disconjugate gaze in a subject with a surgically severed cranial nerve III. FIGS. 25A-N provide box plots of eye movement tracking (left and right eyes). The aspect ratio for each eye is provided. FIGS. 25O-Q provide graphic representation of the eye movement tracking for each eye over time demonstrating the variance in x-axis movement between the left and right eye and the variance in y-axis movement between the left and right eye. Disconjugacy is calculated or quantified at 2.2711.

FIG. 26A shows head CT findings include bilateral parafalcine posterior vertex subdural hematomas measuring up to 8 mm in thickness. There were multiple punctuate-subcentimeter bifrontal contusions, right greater than left. There was a 4 mm left parafalcine subdural hematoma. He had no significant ophthalmic history following his last optometric visit 10 years prior. No other major body injuries. Quantitative serum alcohol level was 130 mg/dl. Medications administered up to 24 hours prior to recruitment included acetaminophen 325 mg, bacitracin, moxifloxacin hydrochloride. FIG. 26B represents eye movement tracking box plots 2 days after triage. The patient was positive for 12/22 symptoms according to SCAT3 with a severity score of 45/132 and GCS score of 13/15. Total SAC score of 17/30. FIG. 26C represents eye movement tracking box plots 13 days after triage. The patient was positive for 10/22 symptoms according to SCAT3 with a severity score of 27/132 and GCS score of 15/15. Total SAC score of 24/30. Medications administered up to 24 hours prior to eye tracking included ibuprofen.

FIG. 27A is a head CT showed a mixed attenuation predominantly hyperdense subdural fluid collection over the left cerebral convexity measuring up to 1.7 cm in thickness with associated mass effect upon the left lateral ventricle and 7 mm left to right midline shift of the septum pellucidum. The patient underwent craniotomy and was recruited for the study from NSICU on the third postoperative day. She denied word finding difficulty and was neurologically non-focal at the time of recruitment and reported no ophthalmic history. Medications administered up to 24 hours prior to recruitment included Keppra, Ancef, Nexium, Heparin, Acetaminophen, Zofran. There were no drugs or alcohol reported for the past 24 hours. FIG. 27B represents eye movement tracking box plots 3 days post operatively and 17 days post injury patient. The patient was positive for 6/22 symptoms according to SCAT3 with a severity score of 17/132 and GCS score of 15/15. Total SAC score of 18/30. FIG. 27C represents eye movement tracking box plots at 35 days post surgery and 49 days post injury. The patient was positive for 13/22 symptoms according to SCAT3 with a severity score of 32/132 and GCS score of 15/15. Total SAC score of 27/30. No medications, drugs or alcohol 24 hours prior.

FIGS. 28A-D represent findings from a 22 year old right-handed male recruited from the emergency room who was participating in a skateboard competition and experienced a fall from 10-15 feet landing on his unhelmeted head. He lost consciousness for approximately 30 minutes and then was agitated, confused and amnestic for the event. His trauma bay GCS was 15 and he had a moderate sized left scalp hematoma on physical examination. FIG. 28A show head CT findings included a comminuted minimally displaced fracture of the left occipitoparietal bone with extension to the anterior aspect of the left temporal bone. There was also a small underlying left subdural hematoma with pneumocephalus. There was partial opacification of the left mastoid air cells, and a non-displaced fracture through the tympanic roof could not be completely excluded. He had no significant ophthalmic history other than eye pressure at the time of recruitment, and his last optometric visit was a year prior. His cranial trauma history included that 1.5 years ago he fell with loss of consciousness. Medications administered up to 24 hours prior to recruitment included levetiracetam 500 mg/100, 0.82% NaCl Premix, Ondansetron 4 mg/50 mL, Acetaminophen 325 mg. FIG. 28B represents eye movement tracking box plots 1 day after injury. The patient was positive for 13/22 SCAT3 symptoms with a severity score of 62/132 and GCS score of 14/15. The total SAC score was 19/30. FIG. 28C represents eye movement tracking box plots 12 days after injury. The patient was positive for 19/22 SCAT3 symptoms with a severity score of 81/132 and GCS score of 15/15. The total SAC score was 17/30. FIG. 28D represents eye movement tracking box plots 66 days after injury. The patient was positive for 19/22 SCAT3 symptoms with a severity score of 69/132 and GCS score of 15/15. The total SAC score was 24/30. No medications, drugs or alcohol were consumed in the 24 hours prior to tracking on any occasion.

FIG. 29A. Represents eye movement tracking box plots 8 days after injury. No SCAT was performed initially. FIG. 29B. Represents eye movement tracking box plots 16 days after injury. The patient was positive for 16/22 SCAT3 symptoms with a severity score of 18/132 and GCS of 15/15. Total SAC score of 22/30. FIG. 29C. Represents eye movement tracking box plots 34 days after injury. The patient was positive for 10/22 SCAT3 symptoms with a severity score of 27/132 and GCS of 15/15. Total SAC score of 22/30. FIG. 29D. Represents eye movement tracking box plots 75 days after injury. The patient was positive for 13/22 SCAT3 symptoms with a severity score of 39/132 and GCS of 15/15. Total SAC score of 26/30.

FIG. 30A. Represents eye movement tracking box plots a few hours after triage. The patient was positive for 14/22 SCAT3 symptoms with a severity score of 72/132 and GCS score of 15/15. His total SAC score was 19/30. He reported feeling severely worse than baseline. FIG. 30B. Represents eye movement tracking box plots at 92 days post triage. The patient was positive for 10/22 SCAT3 symptoms with a severity score of 40/132 and GCS score of 15/15. His total SAC score was 21/30.

FIGS. 31A-D represent the findings from a 53 year old right-handed female recruited from the ER after falling on the street down bus steps, impacting her face. She denied loss of conscious or amnesia and presented immobilized with cervical collar. On examination she had a lip laceration. She had a medical history significant for migraines and bitemporal hemianopsia due to benign pituitary adenoma. Head CT showed moderate multifocal white matter disease to right putamen, posteriorly in the right caudate head and left frontal corona radiate, may be ischemic in origin, and bilateral proptosis. Her last optometric visit was one month prior to recruitment, and she wears corrective lenses and bifocal contact in right eye. Medications administered up to 24 hours prior to recruitment included diovan, lidocaine, hydrochloide 600 mg, acetaminphen 650 mg, vitamins, and tylenol. FIG. 31A. Represents eye movement tracking box plots a few hours after triage. The patient was positive for 16/22 SCAT3 symptoms with a severity score of 40/132 and GCS score of 15/15. The total SAC score was 23/30. FIG. 31B. Represents eye movement tracking box plots at 10 days post injury. The patient was positive for 4/22 SCAT3 symptoms with a severity score of 17/132 and GCS score of 15/15. The total SAC score was 20/30. FIG. 31C. Represents eye movement tracking box plots 17 days post injury. FIG. 31D. Represents eye movement tracking box plots at 113 days post injury. The patient was positive for 16/22 SCAT3 symptoms with a severity score of 48/132 and GCS score of 15/15. The total SAC score was 27/30.

DETAILED DESCRIPTION OF THE INVENTION

Figure 1B:
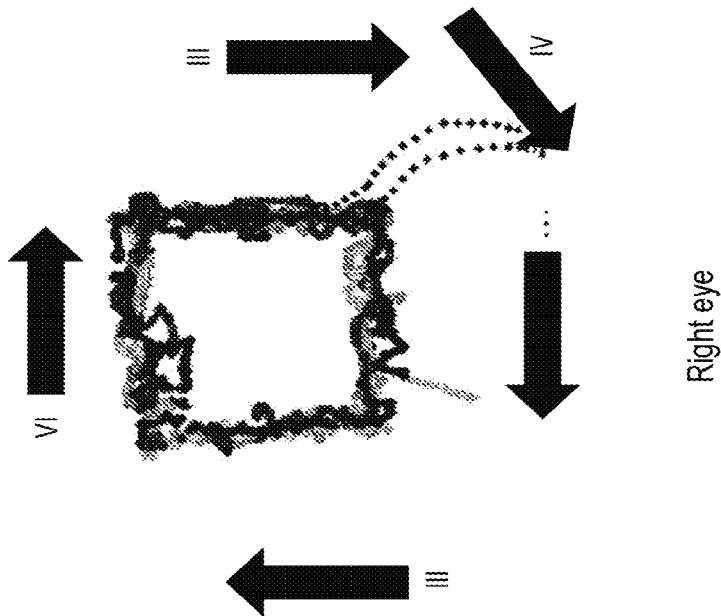

Before the present methods are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims. As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

Definitions

The terms used herein have the meanings recognized and known to those of skill in the art, however, for convenience and completeness, particular terms and their meanings are set forth below.

"Subject" or "patient" refers to a mammal, preferably a human, in need of or undergoing treatment or screening for a condition, disorder or disease such as, for instance, increased intracranial pressure.

By "assessing central nervous system integrity" is meant identifying one or more symptoms that may indicate a pathology of or affecting the central nervous system, or identifying, assessing, quantifying or diagnosing a pathology of the central nervous system. The pathology may be, for instance, one or more of increased intracranial pressure, hydrocephalus, concussion, dementia, schizophrenia, amyotrophic lateral sclerosis, muscular sclerosis, autism and Fragile X disease.

By "localizing a central nervous system lesion" is meant in some instances determining information that may predict a likely position of a lesion, for instance, determining the side of the body, for instance, left or right, where a lesion may likely be located within the central nervous system. In other instances, "localizing a central nervous system lesion" may mean determining a particular fossa or compartment, such as, for instance, a fascia compartment or brain ventricle in which a lesion is likely located within the central nervous system.

By "having eye movement of a first eye that is significantly different from eye movement of a second eye" is meant displaying eye movement in a first eye over 5, 10, 25, 50, 100, 1,000, 5,000, 10,000 or more observations, tracked with at least x, y coordinate positions, that is at least 5%, 10%, 15%, 20%, 25%, 30%, 40%, 50%, 75%, or 100% or more variant compared to the corresponding eye movement observations tracked from the second eye. The 5%, 10%, 15%, 20%, 25%, 30%, 40%, 50%, 75%, or 100% or more variant may be calculated or observed either numerically or graphically. Alternatively, "having eye movement of a first eye that is significantly different from eye movement of a second eye" is meant displaying eye movement in a first eye over 5, 10, 25, 50, 100, 1,000, 5,000, 10,000 or more observations, tracked with at least x, y coordinate positions, that, when graphically displayed in a scatterplot as described herein, is at least 5°, 10°, 15°, 20°, 25°, 30°, 40°, 50°, 60°, 75° or 90° or more variant compared to the corresponding eye movement observations tracked and graphically displayed on a scatterplot as described herein from the second eye.

Elevated Intracranial Pressure

The methods described herein are distinct from conventional methods. As applied to determining intracranial pressure, a conventional ICP monitor determines the brain's pressure number in one spot, an $O_2$ monitor determines an oxygenation number in one spot, imaging reveals what the brain looks like, but the methods described herein provide methods for testing for physiologic function of the cranial nerves that may reflect factors that may delay axoplasmic transport such as elevated intracranial pressure.

The methods described herein may be used to detect elevated intracranial pressure and assess or determine the severity of the same. Similarly, the methods described herein may be used to localize the intracranial cause of such intracranial pressure and to monitor progression of lesions or diffuse processes within the cranium. Likewise, the methods described herein may be used to detect concussion and assess or determine the severity of the same.

The methods described herein provide high sensitivity. No patient yet evaluated with an abnormal physical exam or films consistent with elevated ICP has had normal eye movement tracking. The methods described herein may be used to reduce the need for CT scans among potential shunt malfunction patients, patients with lesions causing elevated intracranial pressure, and may be used to screen patient populations such as emergency room ER populations, sports participants, soldiers or other combatants, nursing home residents or other populations at risk for falling for elevated intracranial pressure or concussion.

High resolution automated eye movement tracking, occurring over, for instance, about 220 seconds, is a powerful tool for detecting subclinically apparent ocular motility dysfunction, and thus aid in the rapid diagnosis of elevated intracranial pressure or concussion.

While palsies of cranial nerves II, III, IV and VI have all been described in patients with acute hydrocephalus (Tzekov et al., *Pediatric Neurosurgery* 1991; 17(6):317-320 and Chou et al., *Neurosurgery Clinics of North America* 1999; 10(4):587-608), the relative vulnerability of each nerve has not been well established. If length of exposure to the subarachnoid space were the sole predictor of vulnerability to intracranial pressure elevation, the IVth nerve would be most vulnerable (median length 33 mm (Hanson et al., *Neurology* 2004; 62(1):33-36)), the IIIrd nerve would be second most vulnerable (26 mm (Adler et al., *Journal of Neurosurgery* 2002; 96(6):1103-1112)) and IInd and VIth would be approximately equally least vulnerable (5 to 16 mm for II (Murali, R. Injuries of the Cranial Nerves. In: Golfinos PCaJ, ed. *Head Injury.* 4th ed. New York: McGraw Hill; 2000), and 11 mm median length for VI (Hanson et al., *Neurology* 2004; 62(1):33-36)).

The abducens nerve (VI) exits the brainstem from its tethering at the medullopontine junction and courses intracranially before entering Dorello's canal, where it is again tethered by fibrous and osseous structures. Elevation of supratentorial ICP forces the parahippocampal gyri down past the free edge of the tentorium while the brainstem with the tethered VIth nerve moves caudally toward the foramen magnum, stretching the nerve where it enters Dorello's canal (Hanson et al., *Neurology* 2004; 62(1):33-36). Posterior fossa lesions pushing the cerebellum and brainstem forward may directly compress the VIth nerve against the clivus (Hanson et al., *Neurology* 2004; 62(1):33-36). It is also possible that the increased reporting of VIth nerve palsies may be due to their easier detection on clinical examination than III and IVth nerve palsies.

The data presented herein does not feature a calibration step in eye movement tracking. Thus patients need not reliably follow instructions, and the data does not filter out the possible effects of cranial neuropathy. Unlike other studies (Contreras et al., *Brain research* 2011; 1398:55-63; Maruta et al., *The Journal of Head Trauma Rehabilitation* 2010; 25(4):293-305; Contreras et al., *Journal of Biological Physics* 2008; 34 (3-4):381-392 and Trojano et al., *J Neurol* 2012; (published online; ahead of print)) the data presented herein does not use saccade count or spatial accuracy as the measure. In addition to results based on the moving aperture's periodic envelope presented in this paper, the methodology also affords a very fine-scale data showing eye movements in response to the successive frames of the movie itself.

The methods described herein build on pre-existing methods that rely on intact ocular motility to address clinical questions. (Lee et al., *Brain research.* 2011; 1399:59-65; Contreras et al., *Brain research* 2011; 1398:55-63; Maruta et al., *The Journal of Head Trauma Rehabilitation* 2010; 25(4):293-305). The methods described herein differ in several ways. First, the present methods feature diagnosing specific clinical conditions related to vision and ocular motility reflecting the function of cranial nerves II, III, IV, VI and associated nuclei rather than measuring cognitive impairment due to primarily cortical mild to moderate traumatic brain injury. Second, the present methods use more fine-scale information, using, for instance, about 100,000 measurements to pull out subtle differences that can be lost through the somewhat arbitrary thresholding of velocity measures into saccades. Third, the present methods do not use measurements of spatial accuracy, which requires transforming the raw data by a series of scaling and rotating processes whose effectiveness depends on the ability of their subjects to follow precise commands reliably. In such methods previously used, it is necessary to exclude the vast majority of neurologically compromised patients. Further, such methods previously used lose any information related to the function of cranial nerves II, III, IV and VI, because the spatial distortions expected to result from damage to these nerves is reversed in the process of spatial calibration.

Trojano et al., *J Neurol* 2012; (published online; ahead of print) recently described uncalibrated eye movement measurements in a population of minimally conscious and persistently vegetative patients. The methods described herein differ in several ways. First, Trojano et al. report data from 11 rather than 25 healthy control subjects. Second, Trojano et al. evaluate chronic disorders of consciousness rather than acute changes in intracranial pressure. Third, Trojano et al. sample eye movements at 60 Hz rather than 500 Hz, effectively reducing the power of the data 100-fold. Fourth, Trojano et al. report differences in On-target and off-target fixations between the groups, despite not having spatially calibrated the data, making these values noisy. Finally, Trojano et al. use static stimuli moving in a quasi-periodic way. The methods described herein use moving images shown within an aperture that moves periodically and allows assessing both coarse and fine eye movement characteristics in both controls and patients.

Clinical Implications

The data presented herein are consistent with compartmentalization of subarachnoid spaces, as several of the patients demonstrate elevated ICP on one side of the brain, but not the other. The methods for ICP assessment described herein represent a significant advantage over conventional radiographic studies because while the latter depict how the brain appears, our technique captures how well it functions. CT scanning may require brief sedation in a pediatric population and risks radiation exposure, while MR may require prolonged sedation. Brain imaging may not be diagnostic of elevated ICP in patients with chronically enlarged ventricles without classic findings such as transependymal flow on T2 weighted MR imaging (Mizrachi et al., *J Neuroophthalmol.* 2006; 26(4):260-263). Patients with non-compliant and slit ventricles may also have elevated ICP in the absence of radiographic abnormality (Engel et al., *Neurosurgery* 1979; 5(5):549-552). Shunt tapping risks infection and malfunction, particularly in patients with slit ventricles. Invasive monitoring risks intracranial hemorrhage. Thus additional low-risk, rapid techniques for assessment of hydrocephalus or elevated ICP may be useful to those assessing populations at risk for these pathologies.

The methods described herein provide a useful adjunct for diagnosis of elevated ICP and the prospective monitoring of such patients at risk for its development. No patients with elevated ICP by history, physical examination and radiology have demonstrated normal ocular motility, demonstrating that the methods described herein are sensitive. The data presented herein demonstrate that patients with grossly intact extraocular movements on physical exam, and relatively minimal changes in pathology, may have profound disruption on high resolution tracking.

The methods described herein provide a useful adjunct for diagnosis of concussion and prospective monitoring of such patients at risk for developing the same. The data presented herein demonstrate that patients with grossly intact extraocular movements on physical exam, and relatively minimal changes in pathology, may have profound disruption on high resolution tracking.

Given the diverse baseline ocular pathology of hydrocephalic patients alone (Dennis et al., *Arch Neurol.* October 1981; 38(10):607-615; Zeiner et al., *Childs Nery Syst.* 1985; 1(2):115-122 and Altintas et al., *Graefe's archive for clinical and experimental ophthalmology=Albrecht von Graefes Archiv fur klinische and experimentelle Ophthalmologic.* 2005; 243(12):1213-1217), tracking results may need to be compared to each patient's own baseline data. Similarly subjects with a history of traumatic brain injury may have tracking results that may need to be compared to each patient's own baseline data.

The data presented herein demonstrates in part that it is possible to diagnose elevated intracranial pressure and concussion by analysis of eye movements during watching of a video. The methods described herein are significantly different from other technologies since imaging studies enable one to see the brain and invasive techniques enable determination of an arbitrary pressure or oxygenation number. The methods described herein actually assess physiologic functioning.

The methods described herein have many clinical applications including, for instance, i) assessing function of cranial nerves II, III, IV and VI, and perhaps even VII, VIII, and/or X; ii) detecting and quantitatively monitoring any process impeding or improving the function of the above (e.g. demonstrating elevated ICP or increased brain mass effect, that may be applied to such things as aneurysms, multiple sclerosis, sarcoidosis, tumors, aging, alcohol abuse, intoxicants/narcotics, etc.), iii) localizing pathology and identifying the nature of that pathology within the brain (e.g. differentiating between lesions that compress nerves and those that only create mass effect or elevate ICP far away); iv) monitoring patients via home computer/webcam, in-hospital or outpatient "TV shows" that perform "neuro-checks" on a regular basis; v) quantitatively measuring outcome for assessment of persistently vegetative and minimally conscious state, aphasia, and recovery from brain injury, particularly concussion; vi) characterizing types of aphasia and localizing pathology; vii) quantitatively assessing dementia/cognitive function and neurodegenerative diseases. Likewise, the methods described herein may provide means for in-person screening such as to, for example, assess vision, assess ocular motility, and assess cognitive dysfunction all relatively simultaneously (e.g. for a driver's or pilot's license, employment etc.). Further, the methods described herein may be used to assess variance, which appears to increase with cognitive decay. This could be used, for instance, to target advertising by stratification of intelligence. Further, the methods described herein may be used to assess disconjugate gaze, that apparently increases with cognitive decay. Still further, the methods described herein may be used for intelligence or neurologic function testing.

Conjugacy of Eye Movement

The present invention features a novel eye movement tracking method that is useful for quantitating gaze conjugacy, and thus disconjugacy, during naturalistic viewing. It may be performed while a subject watches television or a video moving inside an aperture with a set trajectory for about 220 seconds at a fixed distance from a viewing monitor. It may also be performed as the subject views natural stimuli over time. The position of each pupil may be recorded over time elapsed as the video travels on its time course, enabling detection of impaired ability to move the pupils relative to time and therefore relative to each other. This method has high test-retest reliability in control subjects without significant neurologic or ophthalmic impairments using both a stationary and portable eye tracking device.

Eye movement tracking for neuropsychiatric and brain injury research (Heitger, et al., *Brain*, 2009; 132: 2850-2870; Maruta, et al., *J Head Trauma Rehabil.*, 2010; 25: 293-305) has been performed for nearly 30 years and can evaluate smooth pursuit, saccades, fixation, pupil size and other aspects of gaze. Spatial calibration of the eye tracker is generally performed for each individual being tracked. With calibration, the eye-tracker measures the relative position of pupil and corneal reflection for a period of about 400-800 ms while the subject looks at a target or targets of known position to generate meaningful spatial coordinates during subsequent pupil movement. The process of spatial calibration implies relatively preserved neurologic function because it requires that the subject is able to follow commands and look at specific points.

The process of spatial calibration may mask deficits in ocular motility. If there is a persistent and replicable weakness in movement of an eye, the camera may interpret the eye's ability to move in the direction of that weakness as the full potential range of motion in that direction due to the calibration process. In other words if the subject is directed to look at a position but consistently only moves halfway there, the calibration process may account for that when tracking subsequent eye movements and interpret movements to the halfway point as occurring at the full range of normal motion. If during calibration one eye only makes it halfway to the target, but the other eye is fully there, the camera may interpret both eyes as being together when one performs half the eye movement as the other. Thus binocular spatial calibration may preclude detection of disconjugate gaze unless each eye is calibrated separately using a dichoptic apparatus (Schotter, et al., *PLoS One*, 2012; 7: e35608).

The present invention provides a novel technique for non-spatially calibrated tracking performed while subjects watch a music video moving inside an aperture on a computer monitor. The aperture moves around the monitor periphery at a known rate so that the position of the pupil can be predicted at any given time based on the time elapsed since the start of the video. By using elapsed time, rather than spatial calibration, the method detects impaired ability to move one pupil relative to the other. Uncalibrated tracking not only does not compensate for impaired motility, but also can be used in patients who do not follow commands such as aphasics, foreign-language speakers, persistently vegetative individuals and small children. It can also be used on animals.

If the subject's eyes are positioned about 55 cm from the center of the 30×35 cm viewing monitor, the method and associated algorithm elicits pupil movement in a maximum range of about 15° in any direction from midposition, or approximately 30° total from top to bottom or side to side. Thus, in some instances, the method and associated algorithm may not require or assess the full range of ocular motility, nor the entire visual field. Use of a larger monitor, or one positioned closer to the subject would enable assessment of these.

The observed and measured conjugacy was significantly higher in the horizontal plane than vertical. This may reflect any of multiple factors: (1) the shape of the monitor was not a perfect square but rather a 17" diameter rectangle. Each side was traversed in 10 seconds so the eyes had a greater distance to travel horizontally than vertically. Because the eyes were moving faster horizontally they may possibly be more conjugate. (2) Humans have stronger event related desynchronization on electroencephalogram with horizontal versus vertical eye movements (Kaiser, et al., *Clin Neurophysiol.*, 2009; 120: 1988-1993). Humans may have evolved to have higher conjugacy in the horizontal plane than in the vertical because more prey and predators are likely to be at near the same altitude rather than above or below. Other species have demonstrated differences in vertical versus horizontal eye movements (Lisberger, et al., *J Neurophysiol.*, 1989; 61: 173-185). (3) The control population is predominantly English speaking and thus reads from left to right, and reads faster horizontally than vertically (Seo, et al., *Vision Res.*, 2002; 42: 1325-1337). Testing of a population that reads vertically may potentially yield higher vertical conjugacy.

The technique described herein differs from uncalibrated tracking using static stimuli for On-target and off-target fixations in a population of minimally conscious and persistently vegetative patients that have open eyes (Trojano, et al., J Neurol., 2012 (published online; ahead of print)). The moving images shown within an aperture that moves periodically allow assessing both coarse and fine eye movement characteristics in both controls and neurologically impaired subjects. Unlike other studies (Contreras, et al., *Brain Res.*, 2011; 1398: 55-63; Contreras, et al., *J Biol Phys.*, 2008; 34: 381-392; Maruta, et al., *J Head Trauma Rehabil.*, 2010; 25: 293-305; Trojano, et al., J Neurol., 2012 (published online; ahead of print)) the present methods do not use saccade count or spatial accuracy which requires transformation of raw data by a series of scaling and rotating processes whose effectiveness depends on the ability of their subjects to follow precise commands reliably. The present methods also differ from gaze estimation, which requires either a fixed head position or multiple light sources and cameras to localize the pupil (Guestrin, et al., *IEEE Trans Biomed Eng.*, 2006; 53: 1124-1133).

Video oculography is a relatively newer technique that uses infrared cameras mounted in goggles to track the center of the pupil's position as the eye moves. It has been demonstrated to be useful in screening for neurovestibular and labyrinthine dysfunction and most recently in distinguishing these from vertebrobasilar stroke (Newman-Toker, et al., *Stroke,* 2013; 44: 1158-1161). Video oculography generally relies on spatial calibration (Hong, et al., *Behav Res Methods,* 2005; 37: 133-138; Schreiber, et al., *IEEE Trans Biomed Eng.,* 2004; 51: 676-679). The use of our non-calibrated stimulus algorithm with video oculography rather than a sole eye tracking camera might be an interesting subject for future study.

The methods described herein provide both sensitivity and specificity. Because so many different cortical functions are required for watching a video, any process impeding global cranial function or specific cranial nerve function will likely be revealed by the present methods. Tracking may be confounded in patients with a history of prior brain insult, who are intoxicated, or are under the influence of pharmacologic agents. Patients' cognitive abilities, attention span and distractibility will impact the quality of ocular motility data.

The methods described herein are useful for screening for strabismus. In a population of 14,006 consecutive patients examined at a pediatric eye clinic in Rome, 2.72% demonstrated either A or V-pattern strabismus (Dickmann, et al., *Ophthalmic Epidemiol.,* 2012; 19: 302-305). A-pattern was associated with a greater prevalence of neurological impairment, hydrocephalus and meningomyelocele, while those with V-pattern exhibited a greater prevalence of craniosynostosis and malformative syndromes (Dickmann, et al., *Ophthalmic Epidemiol.,* 2012; 19: 302-305). Delays in treatment of strabismus onset following binocular vision maturation may be associated with permanent disruption of stereopsis and sensory fusion (Fawcett, *Curr Opin Ophthalmol.,* 2005; 16: 298-302).

Given the relatively low prevalence of strabismus, the methods described herein are useful for the rapid automated assessment of acquired disconjugacy. Such disconjugacy may be due to neurologic causes including trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. Disconjugacy may also be due to ophthalmologic causes such as conjunctivitis, ophthalmoplegia, ocular injury or other diseases. As such, the methods described herein are useful for screening for strabismus or congenital disconjugate gaze, screening for acquired disconjugate gaze due to neurologic causes including trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. Disconjugacy may also be due to ophthalmologic causes such as conjunctivitis, ophthalmoplegia, ocular injury or other diseases, and assessing reading/learning disorders.

Binocular Eye Movement Monitoring

When the human brain is physiologically intact, the eyes move together with a conjugate gaze. Only by deliberate conscious effort can an individual overcome this mechanism (eg when they deliberately "cross" the eyes.) A failure of the eyes to move in complete synchrony is called disconjugate gaze.

Binocular tracking may be used to compare the non-spatially calibrated trajectory of one eye to the other. Subtle differences between the trajectories of the two eyes may be detected. These differences provide valuable information regarding the physiologic function or dysfunction of the movement of one eye relative to the other. In the absence of known structural ocular injury, such differences reflect physiologic differences in the function of the two sides of the brain. Since brain lesions due to stroke, trauma or concussion, tumors, demyelinating disease, hydrocephalus, degenerative disease, etc. are rarely completely symmetric, comparing the eye movement of one eye to the eye movement of the other eye may be used to either confirm the presence of a lesion, to differentiate the existence of a lesion from other more global factors that may affect a person's ability to participate in an eye tracking task, such as fatigue, intoxication, medications, drug abuse, malingering, or lack of willingness to participate in an eye tracking task.

Thus binocular tracking and directly comparing the trajectories obtained over time, rather than with spatial calibration, may be used to diagnose pathology and to distinguish between these diagnoses and global factors that may impact eye tracking. In addition to or instead of an eye tracking camera, a video oculography device such as goggles may be used to evaluate eye movements over time rather than with spatial calibration. The eye tracking device may also be located remotely and function via the internet or other visualization mechanism.

Computing System

Figure 13:
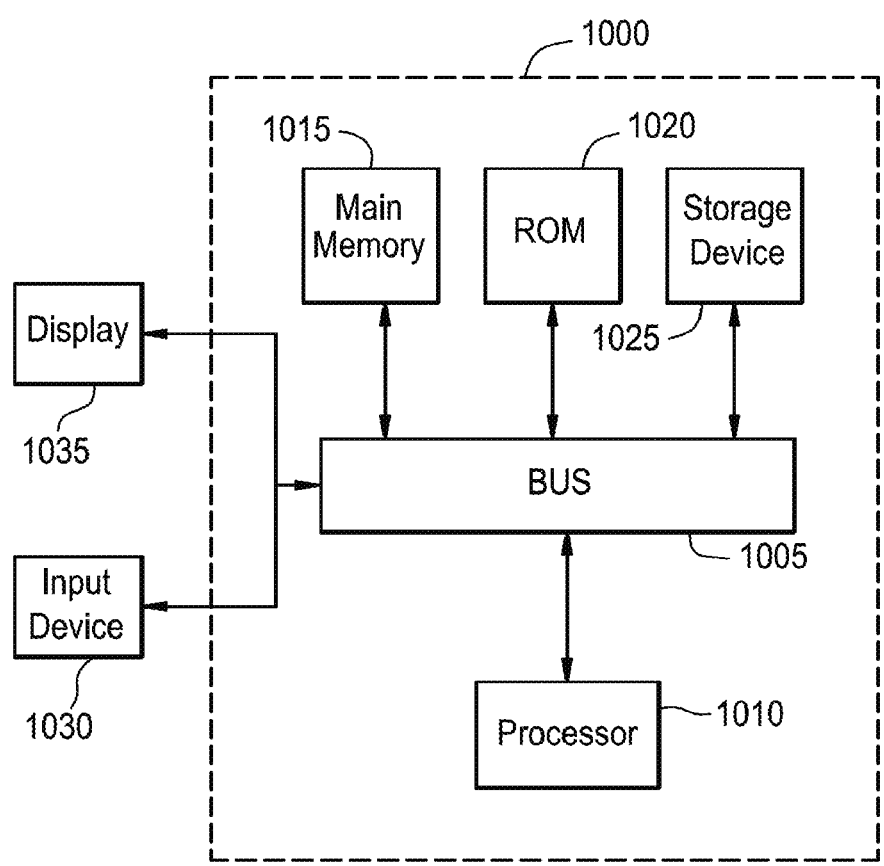
FIG. 13 is a block diagram of a computer system in accordance with an illustrative implementation.
Figure 14:
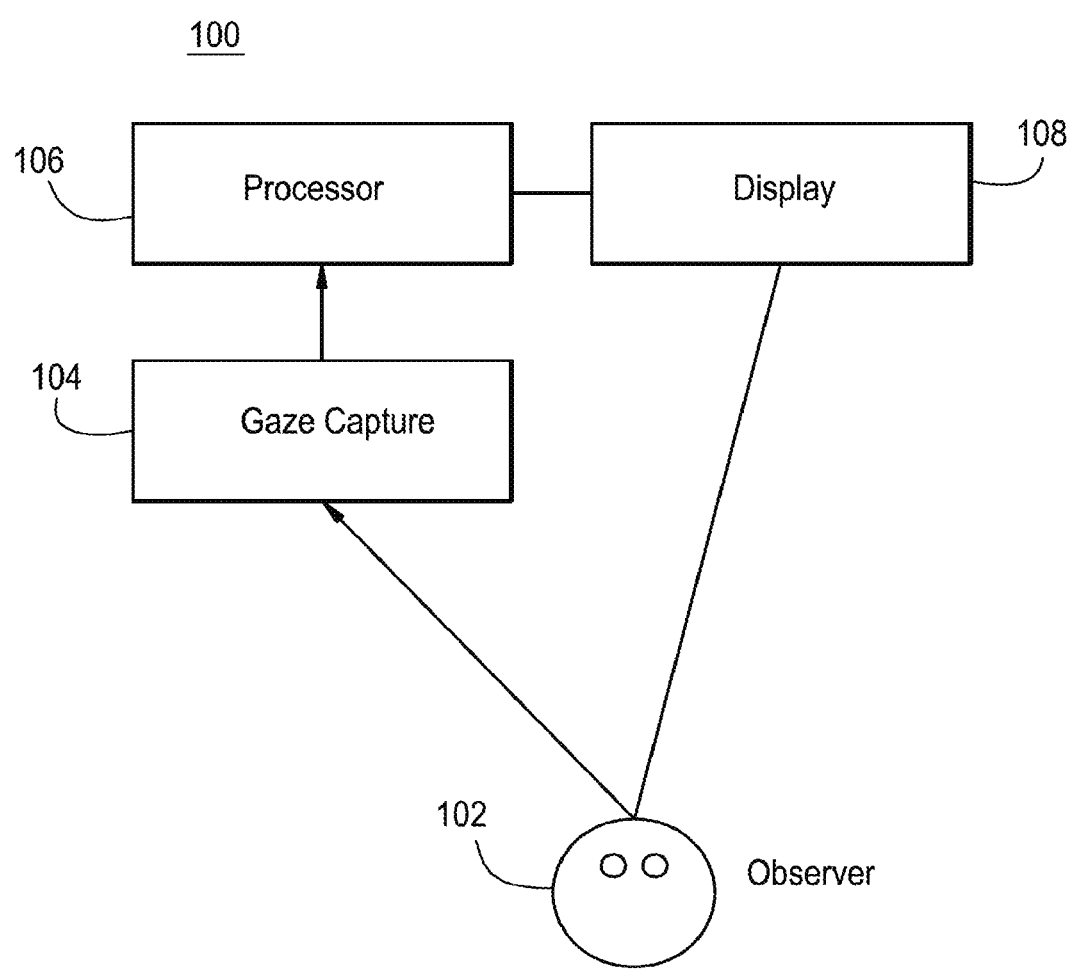
FIG. 14 is a schematic diagram showing a configuration of how a subject's eye movements are measured, analyzed and displayed by such a computer system.
Figure 15E:
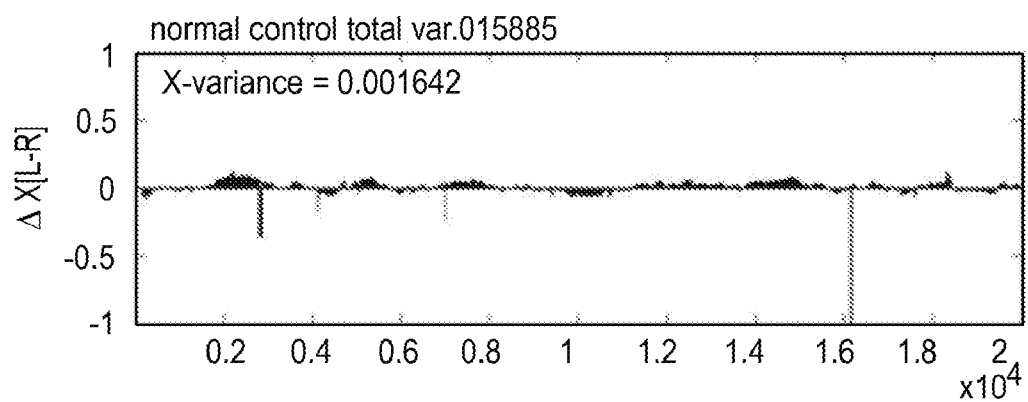
Figure 15F:
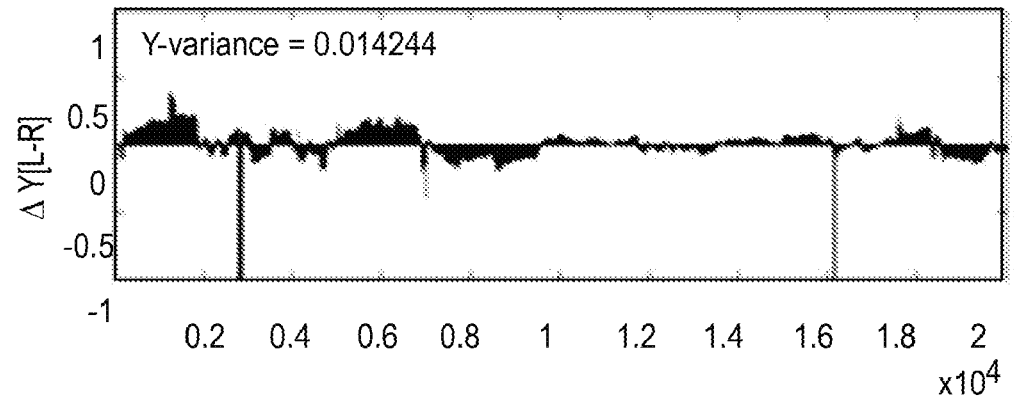
Figure 16B:
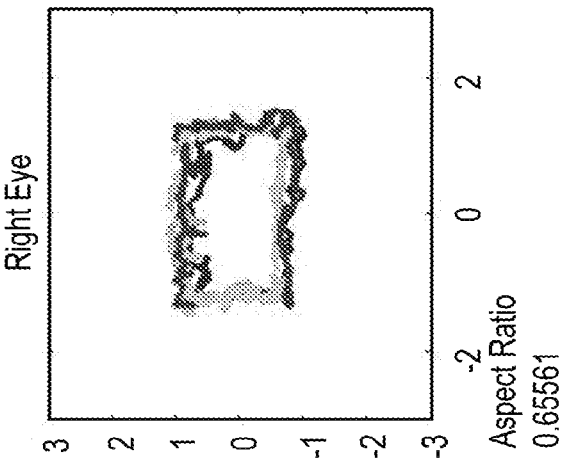
Figure 16A:
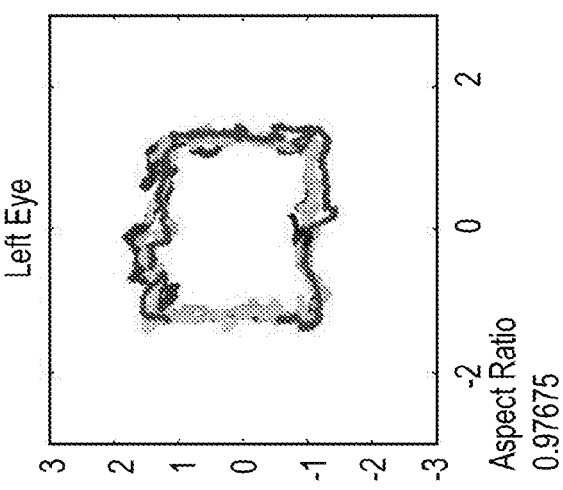
Figure 16D:
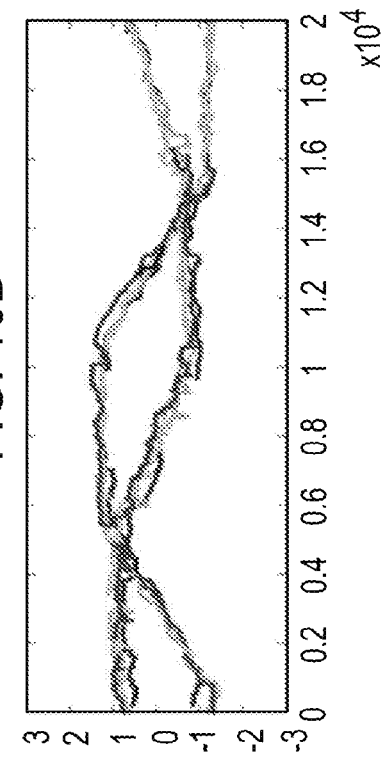
Figure 16C:
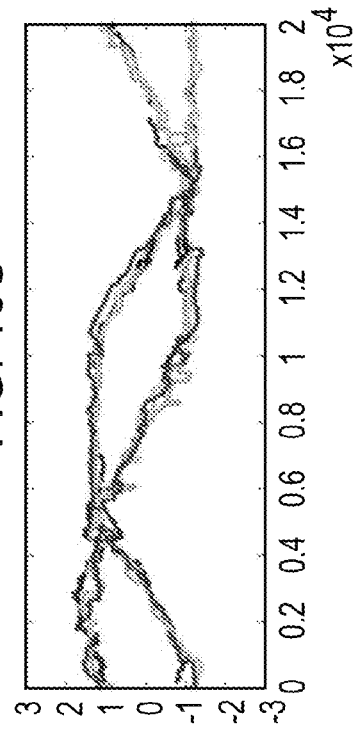
Figure 16E:
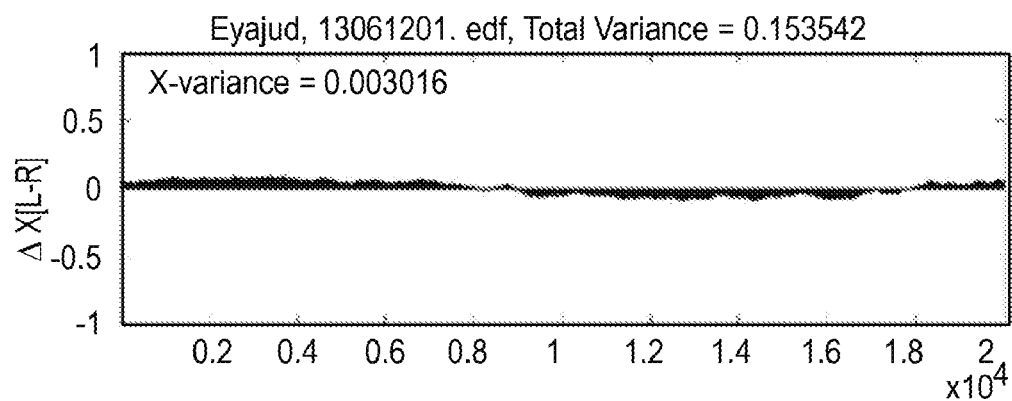
Figure 16F:
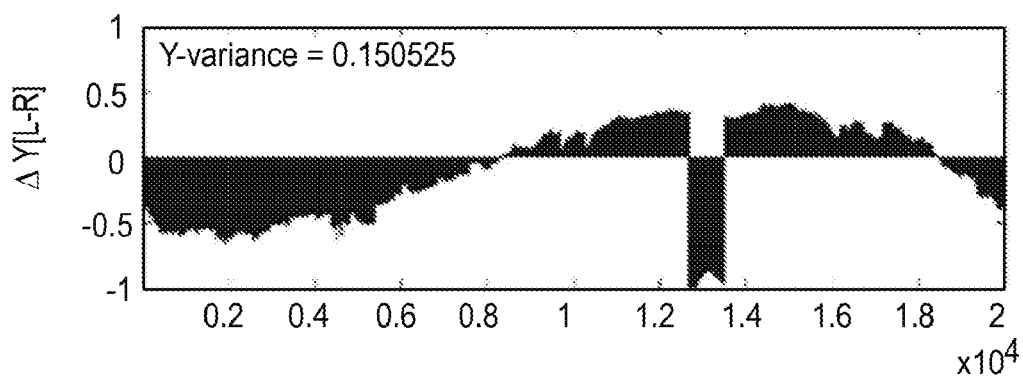
Figure 16K:
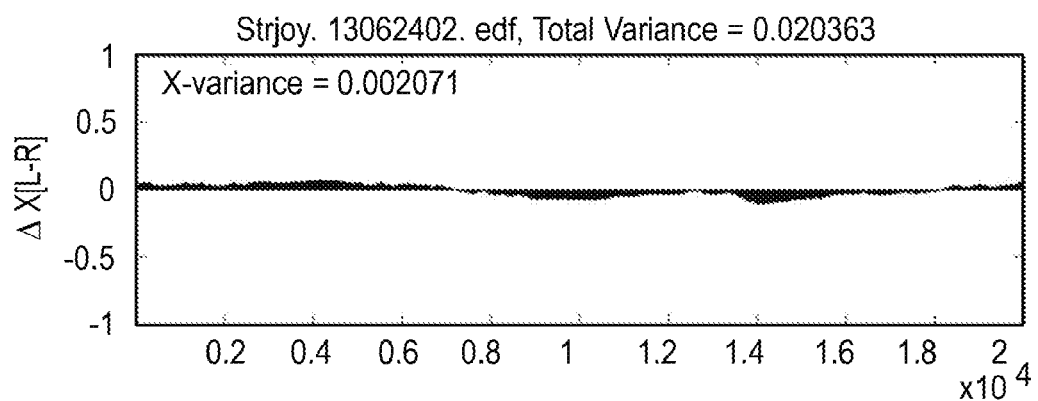
Figure 16L:
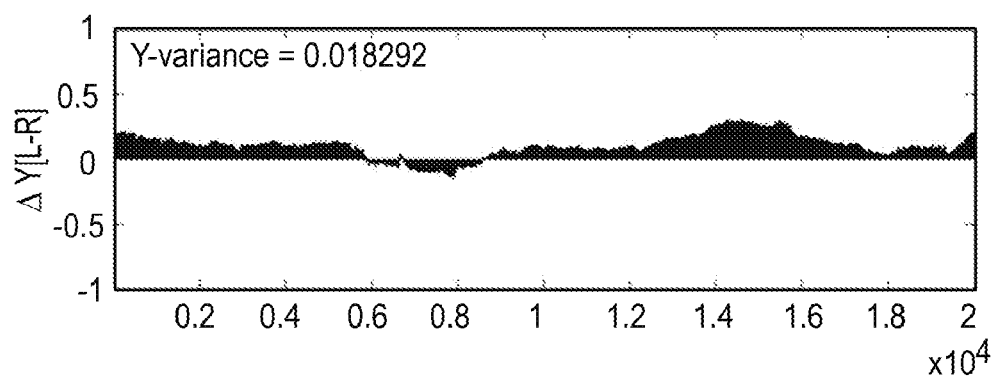
Figure 17E:
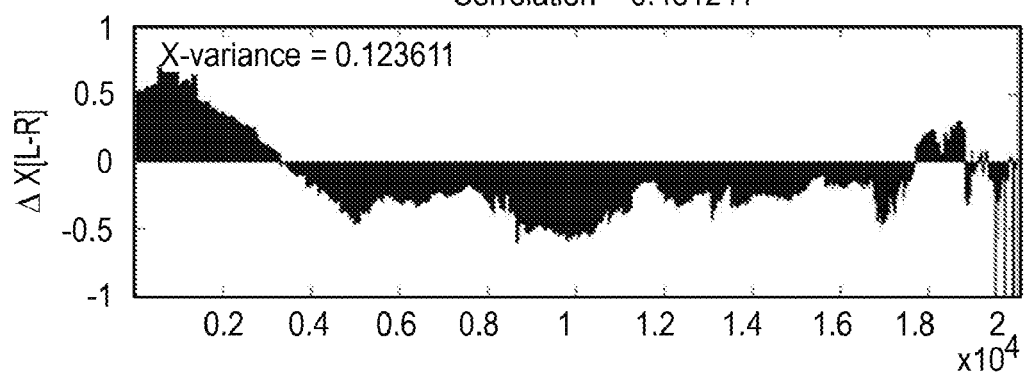
Figure 17F:
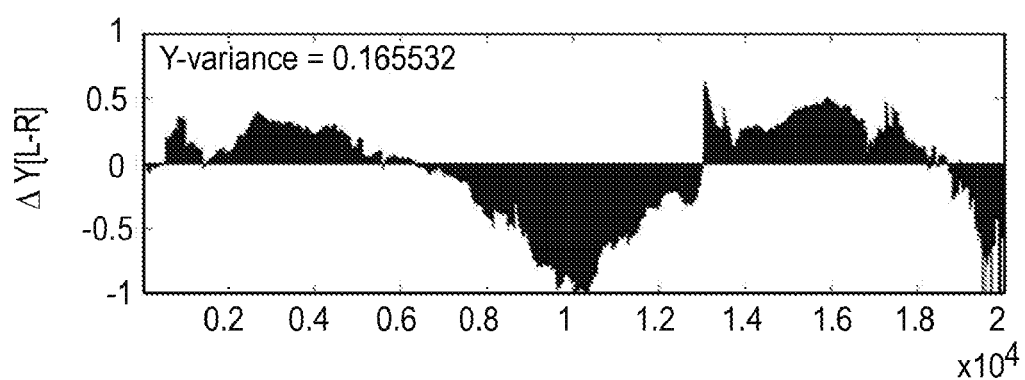
Figure 18E:
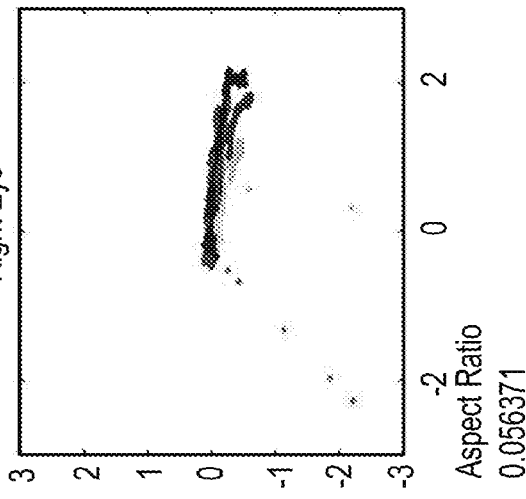
Figure 18F:
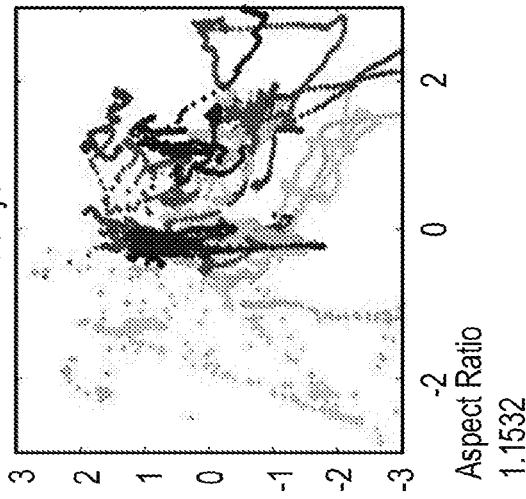
Figure 18G:
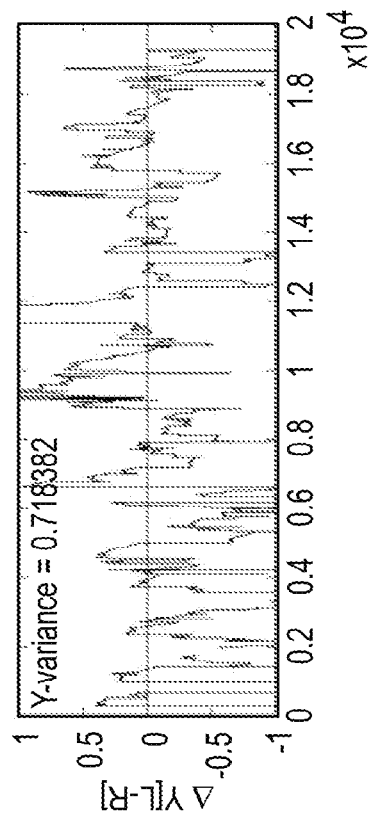
Figure 18H:
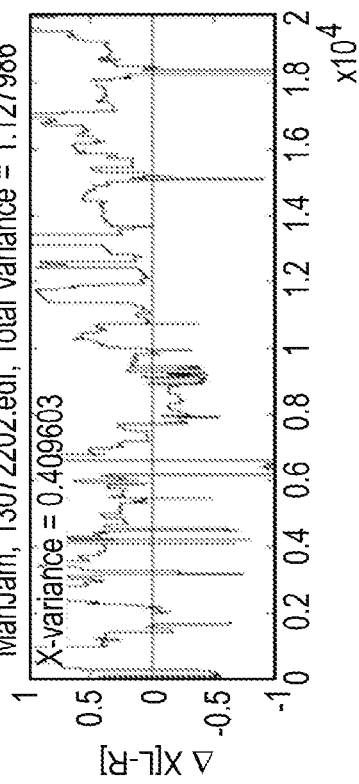
Figure 19A:
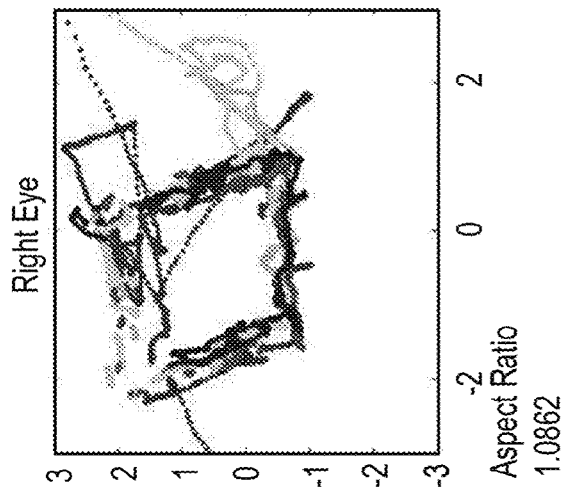
Figure 19B:
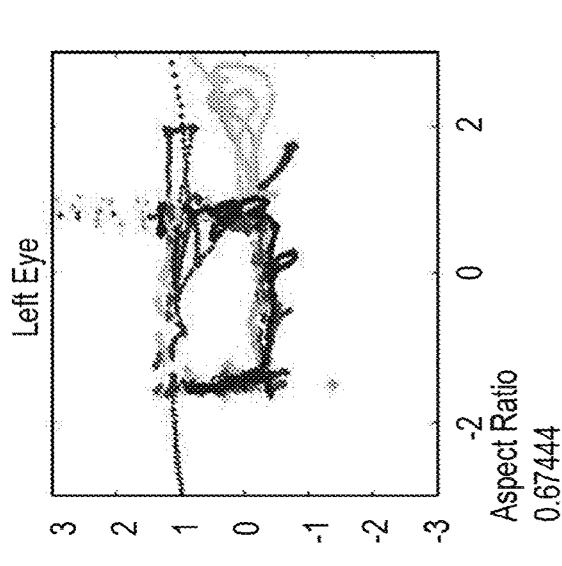
Figure 19C:
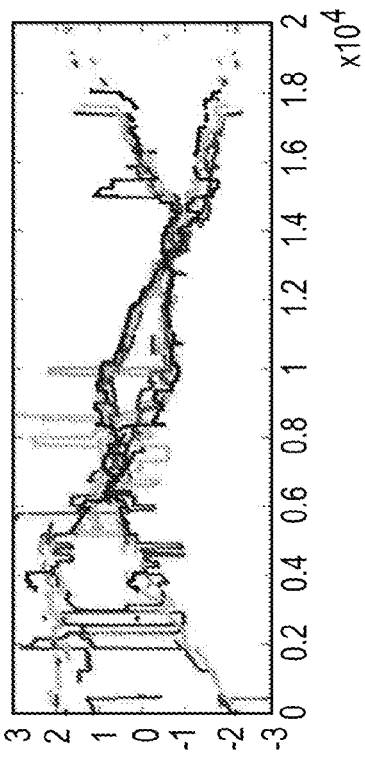
Figure 19D:
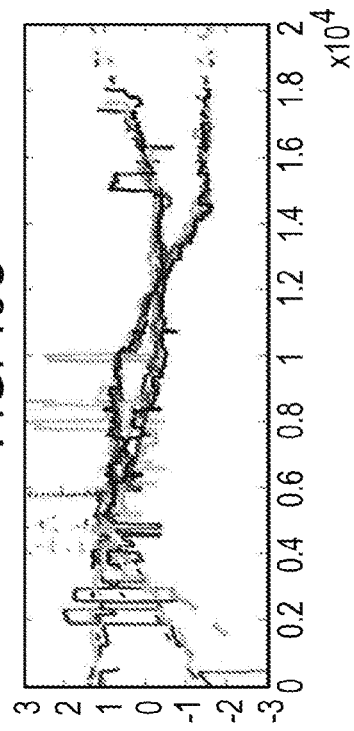
Figure 19E:
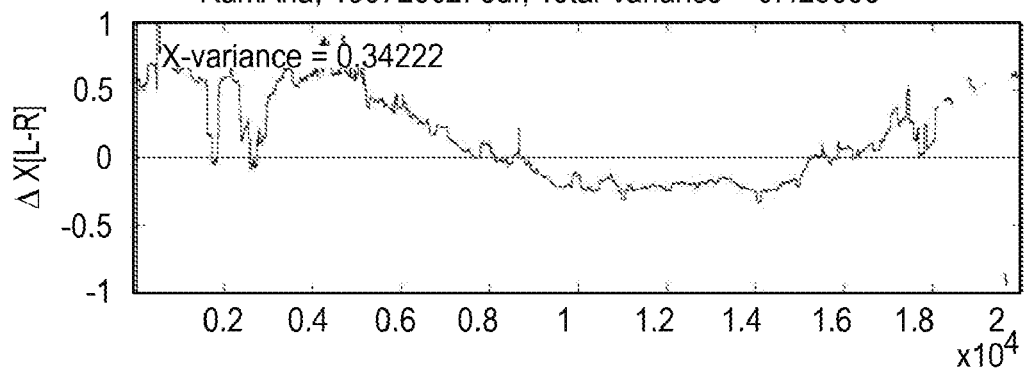
Figure 19F:
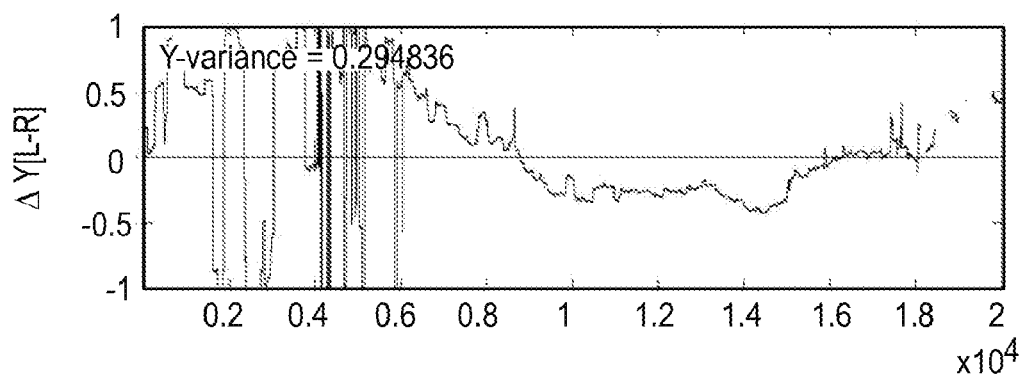
Figure 19K:
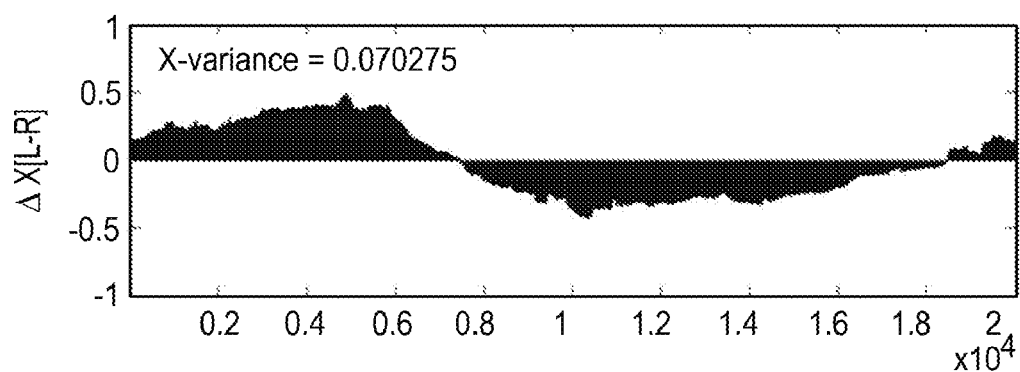
Figure 19L:
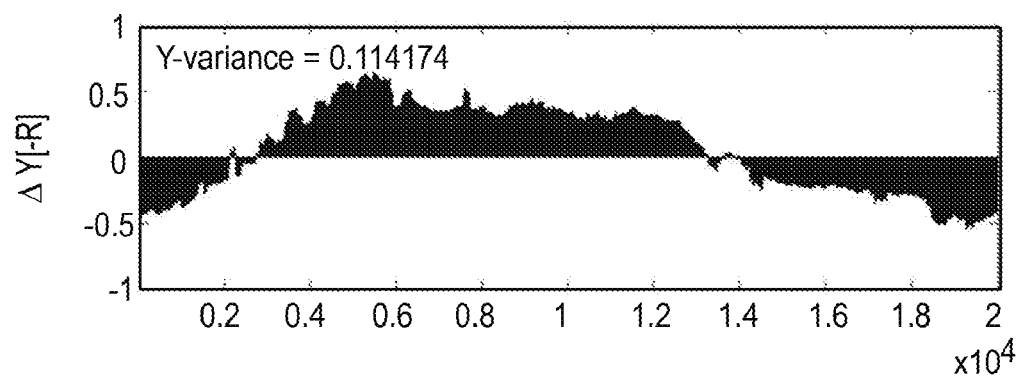
Figure 20E:
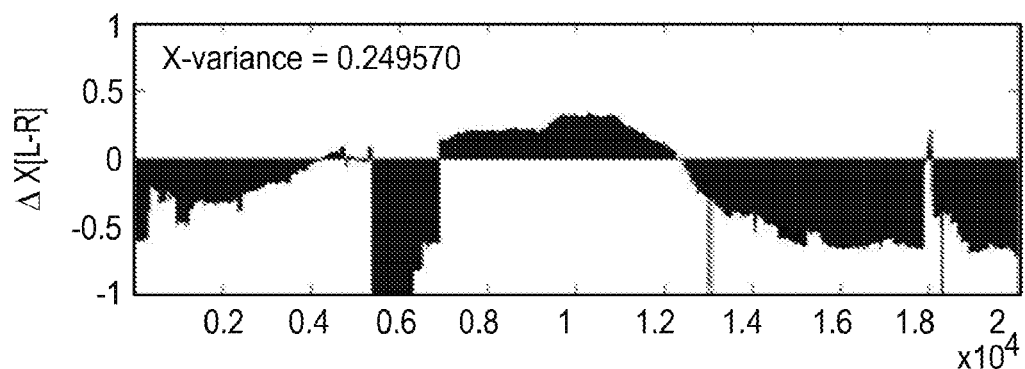
Figure 20F:
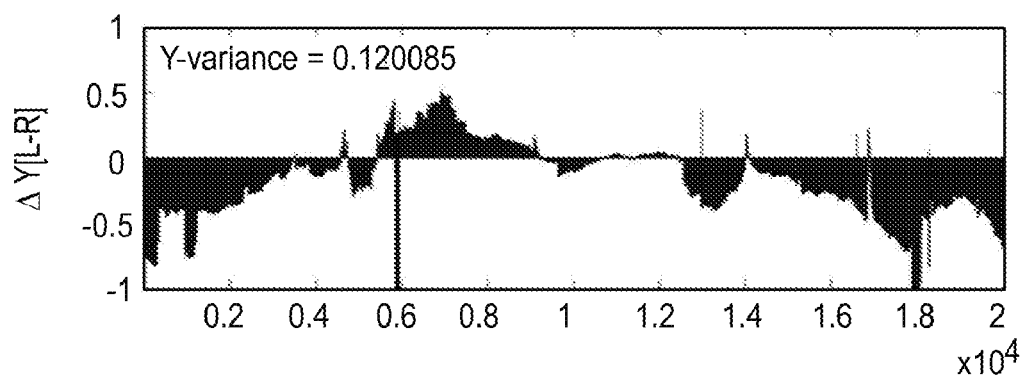
Figure 21E:
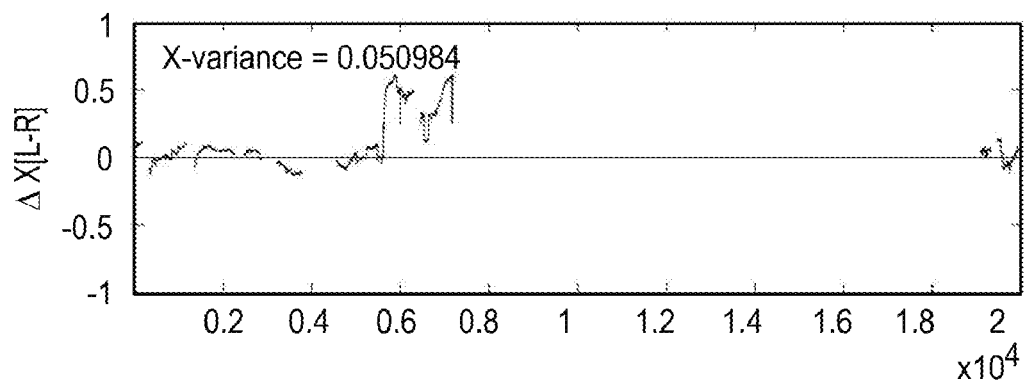
Figure 21F:
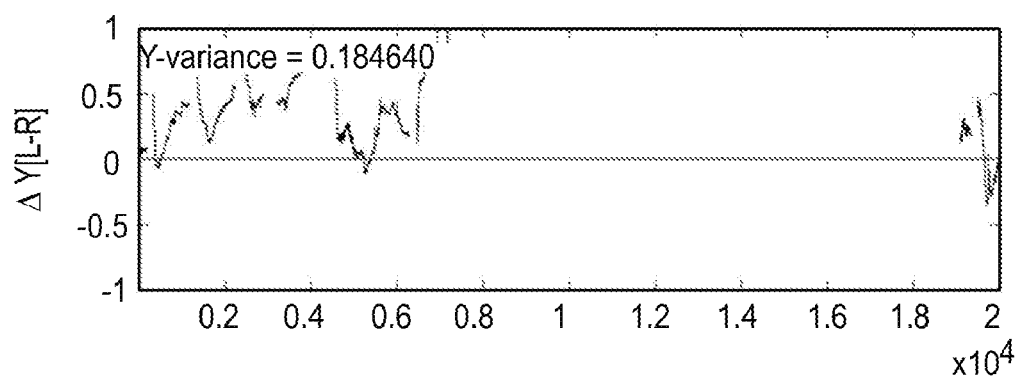
Figure 22E:
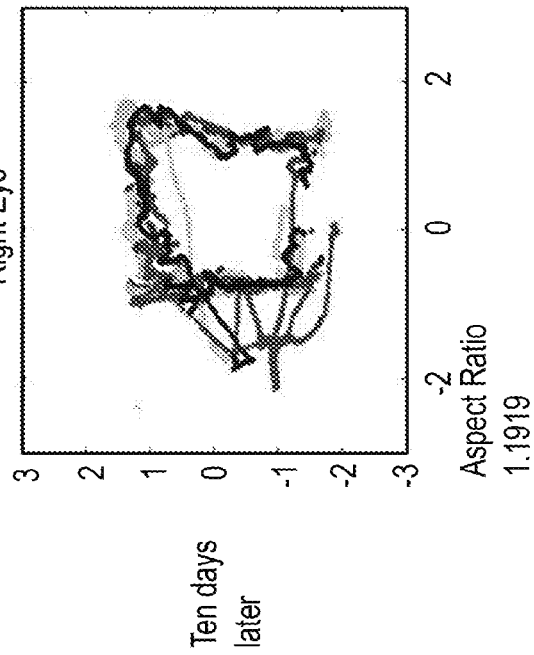
Figure 22F:
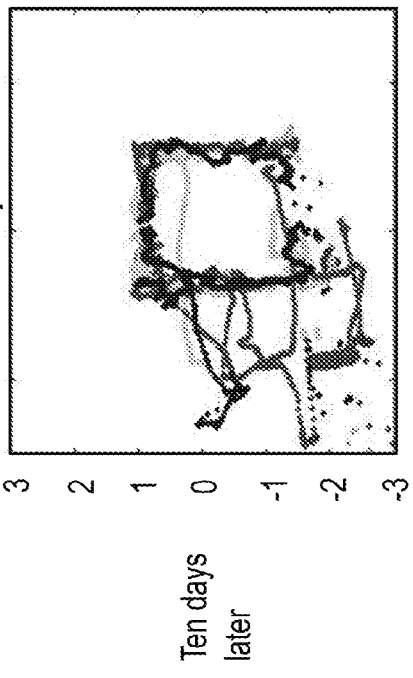
Figure 22G:
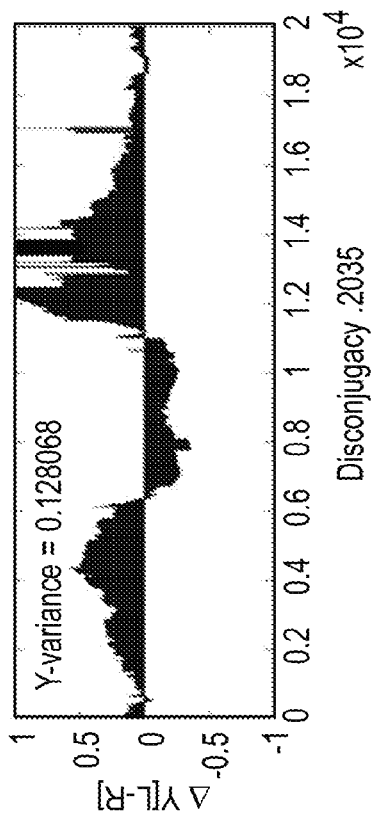
Figure 22H:
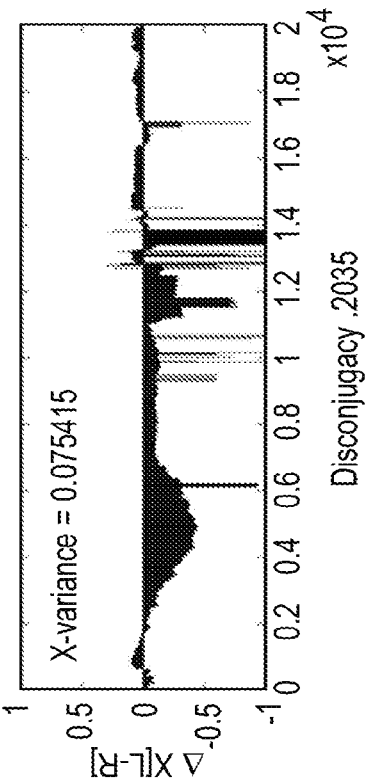
Figure 23A:
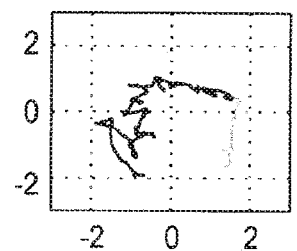
FIGS. 23A-Q provide a representation of the disconjugate gaze in a subject suffering a severed cranial nerve III.
Figure 23B:
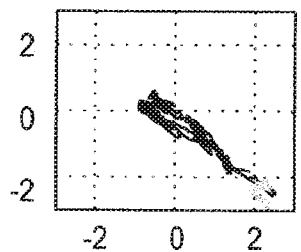
Figure 23C:
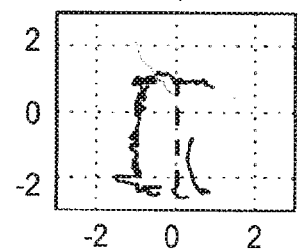
Figure 23D:
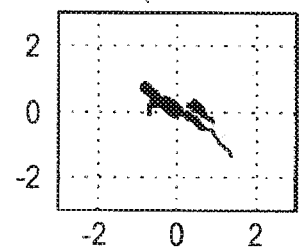
Figure 23E:
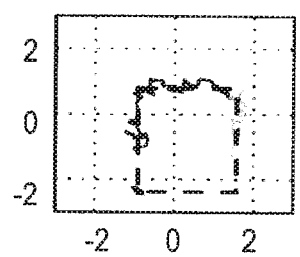
Figure 23F:
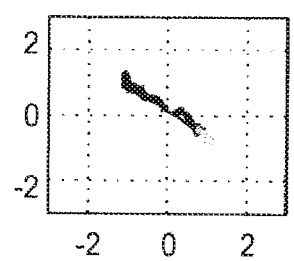
Figure 23G:
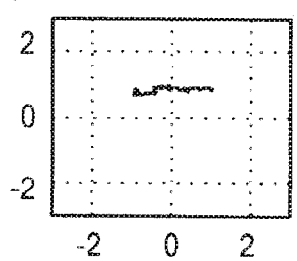
Figure 23H:
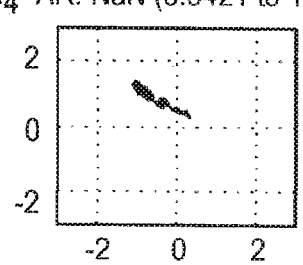
Figure 23I:
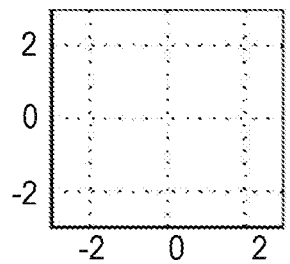
Figure 23J:
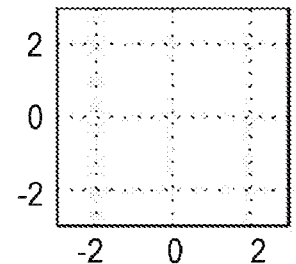
Figure 23K:
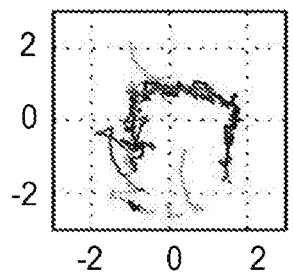
Figure 23L:
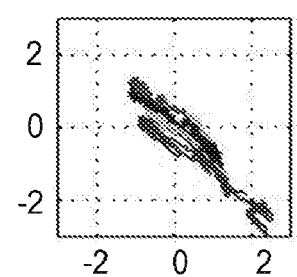
Figure 23M:
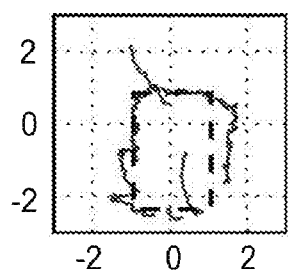
Figure 23N:
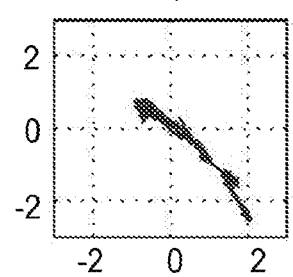
Figure 23O:
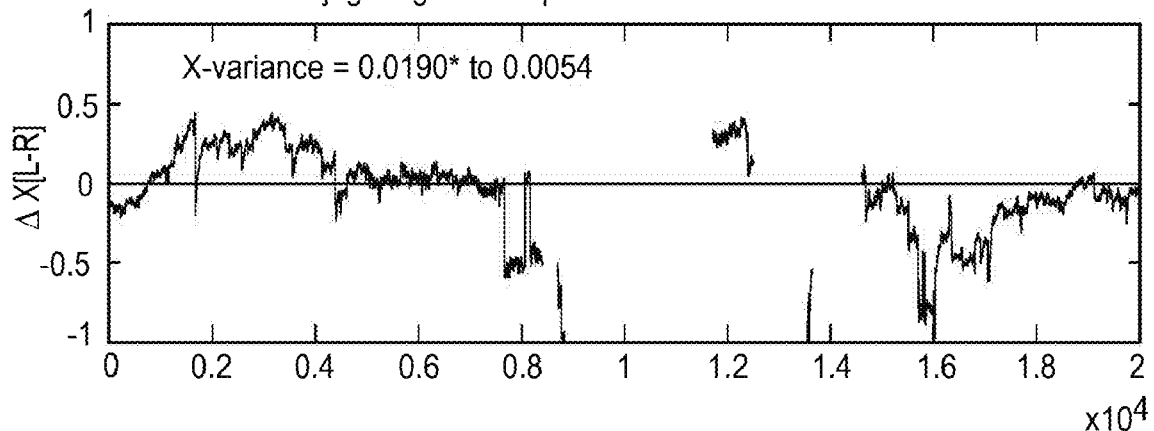
Figure 23P:
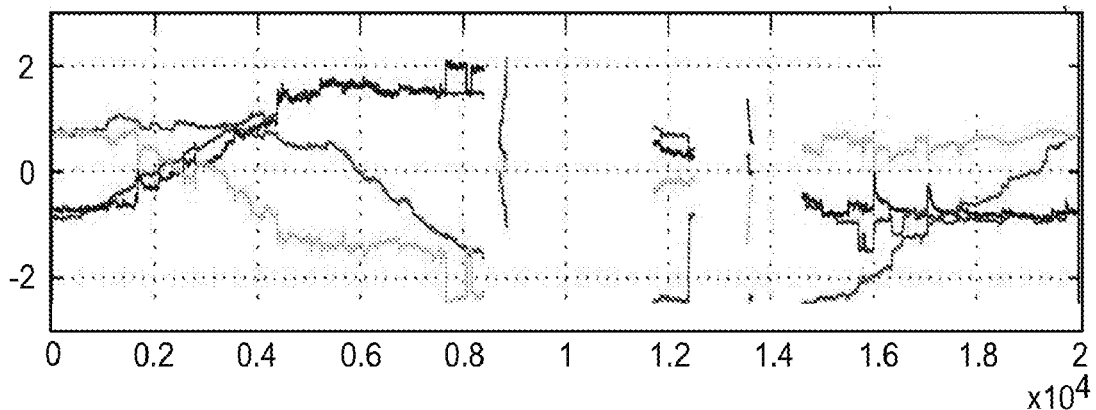
Figure 23Q:
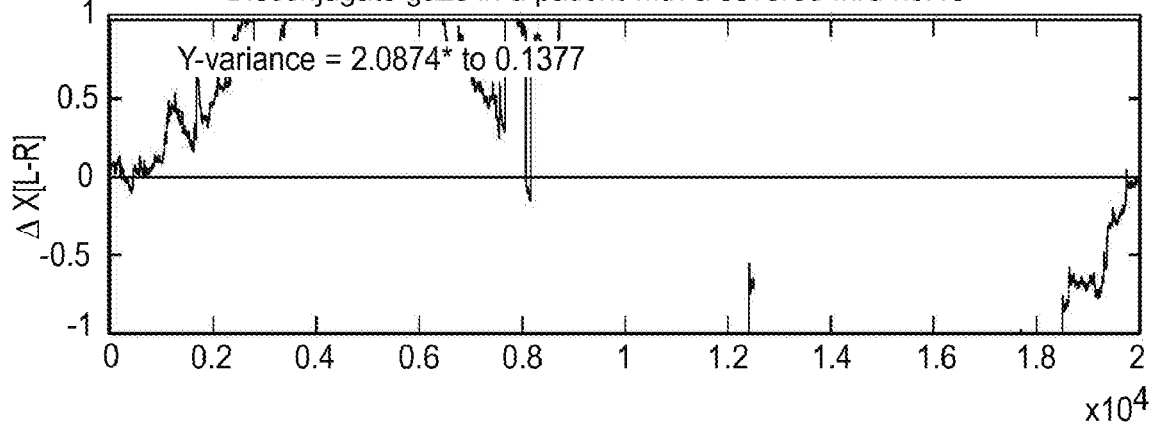
Figure 24A:
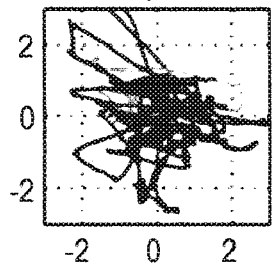
FIGS. 24A-Q provide a representation of the conjugate gaze in a normal subject while watching television.
Figure 24B:
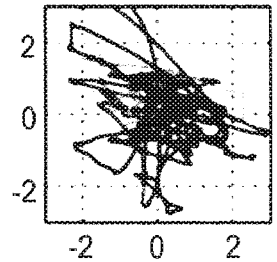
Figure 24C:
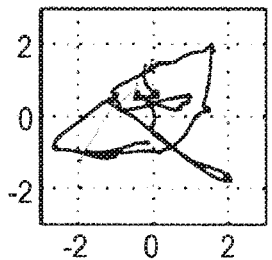
Figure 24D:
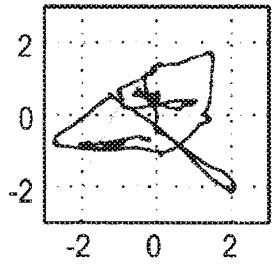
Figure 24E:
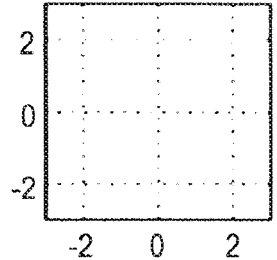
Figure 24F:
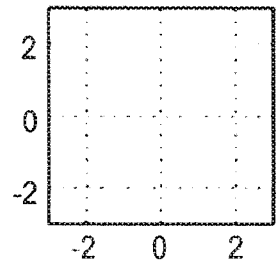
Figure 24G:
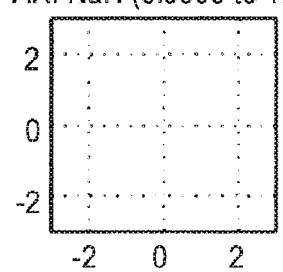
Figure 24H:
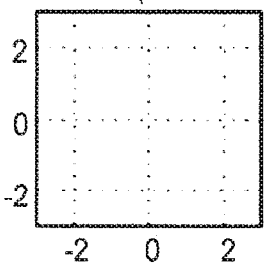
Figure 24I:
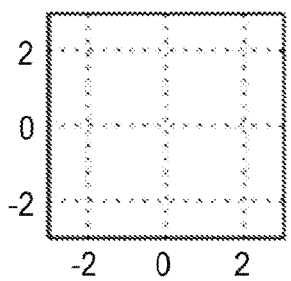
Figure 24J:
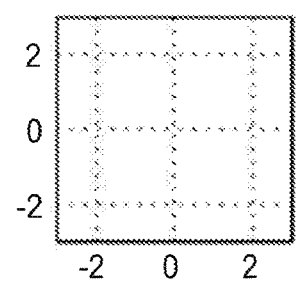
Figure 24J:
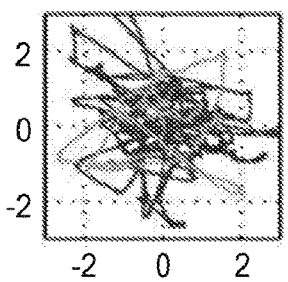
Figure 24L:
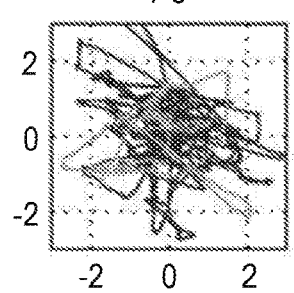
Figure 24M:
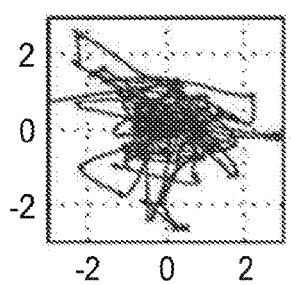
Figure 24N:
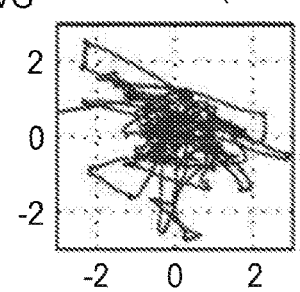
Figure 24O:
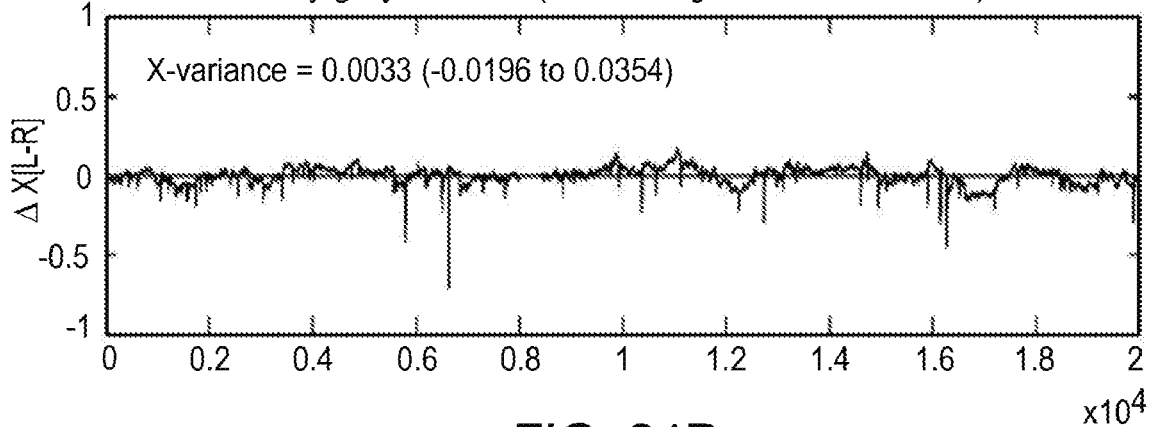
Figure 24P:
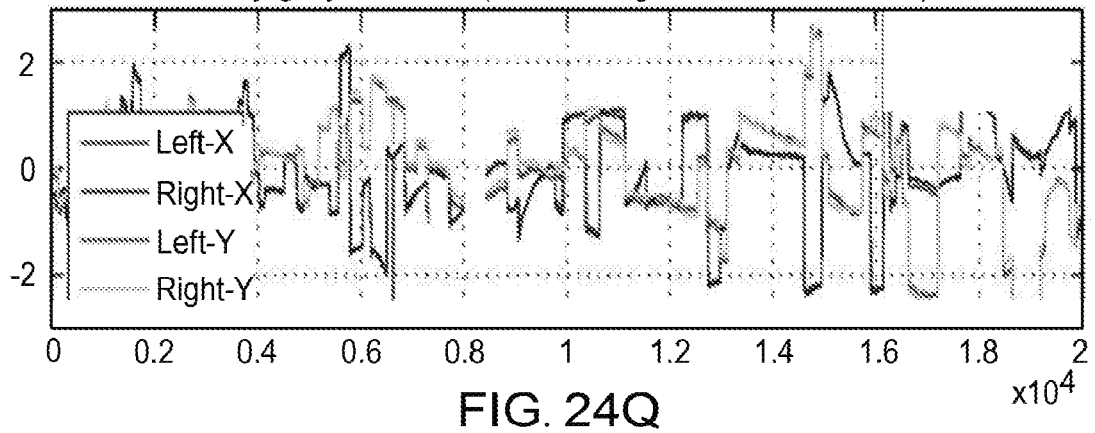
Figure 24Q:
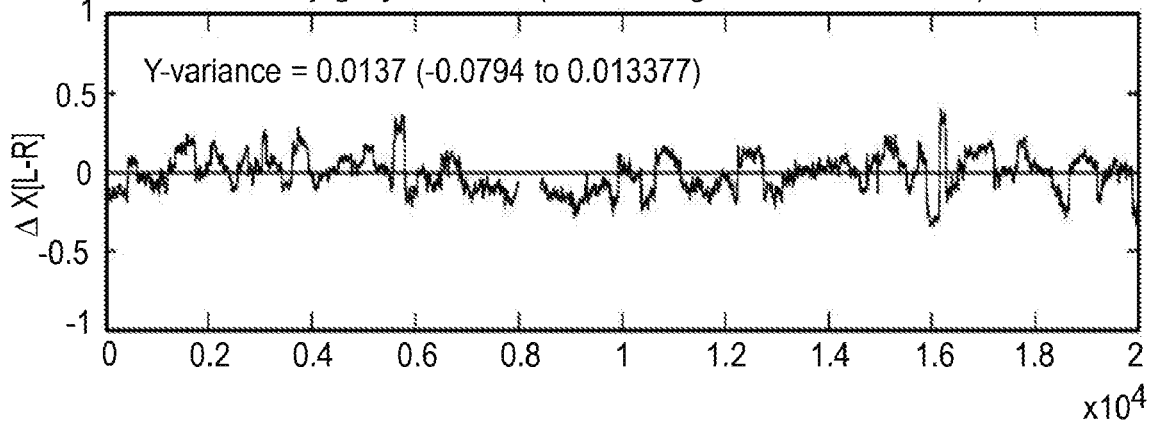
Figure 25I:
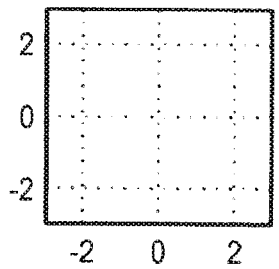
Figure 25J:
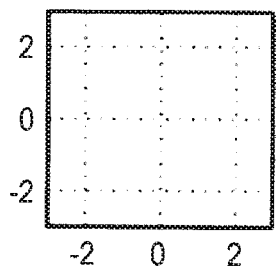
Figure 25K:
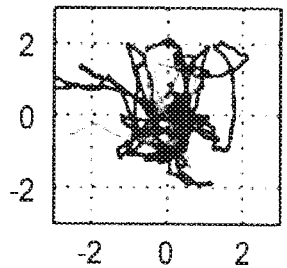
Figure 25L:
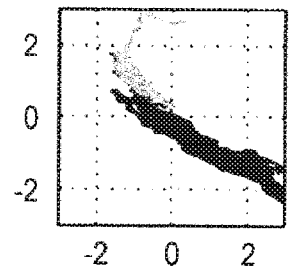
Figure 25M:
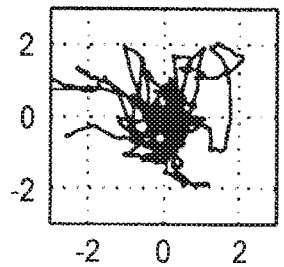
Figure 25N:
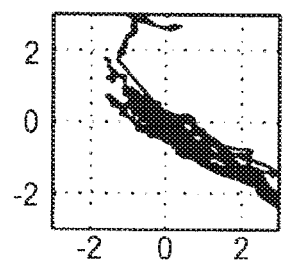
Figure 26A:
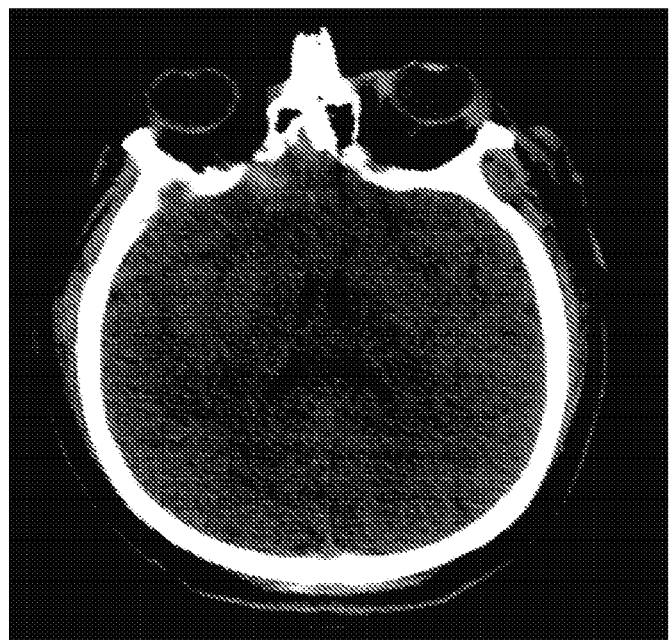
FIGS. 26A-C represent findings from a 38 year old right-handed male recruited from the emergency room after being hit by a car while riding his bicycle. The patient was brought in with a backboard and C-collar, intoxicated with reported loss of consciousness and normal vitals but intermittent confusion with retrograde amnesia. On physical examination he was alert and oriented ×3, had a right eye hematoma and a posterior vertex soft tissue hematoma. He had active bleeding over a 5 cm vertical laceration overlying the left maxilla.
Figure 26B:
Figure 26C:
Figure 27A:
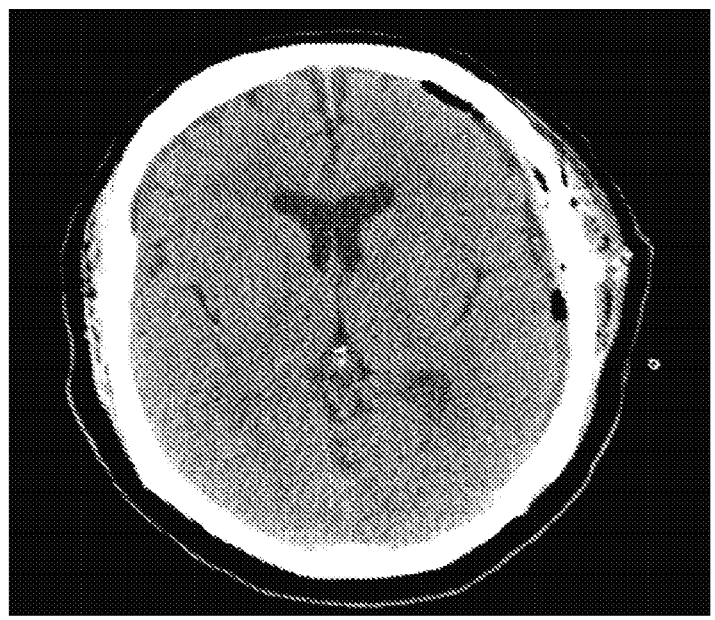
FIGS. 27A-C represent findings from a 37 year old right-handed female. The patient fell 2 weeks prior to seeking medical care. She denied loss of consciousness at the time. After taking aspirin, she developed word finding difficulty 4 days prior to admission. She presented to the emergency room where her examination was otherwise non-focal.
Figure 27B:
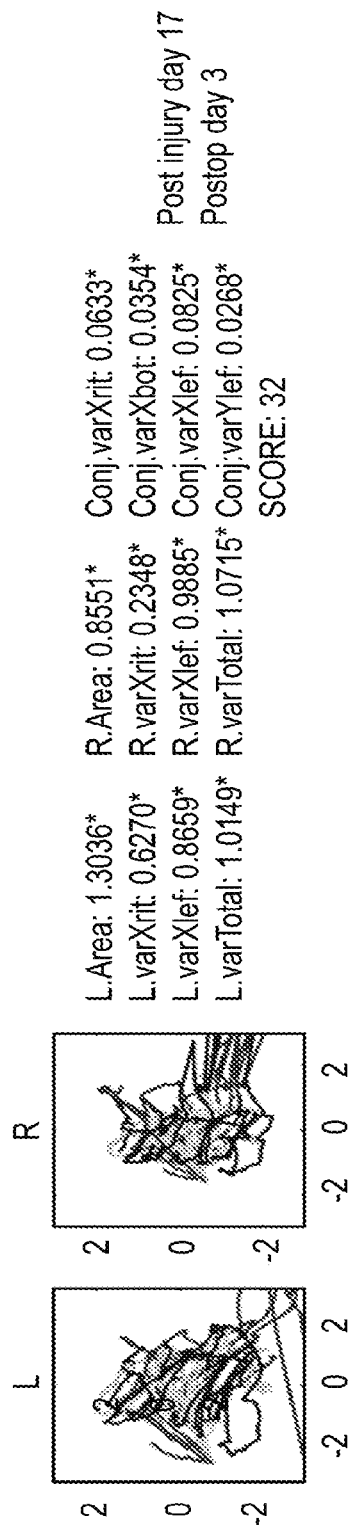
Figure 27C:
Figure 28A:
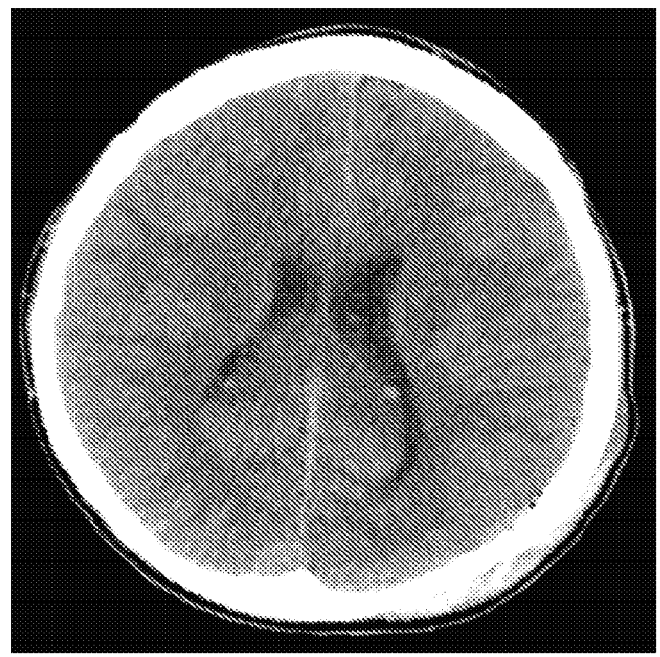
Figure 29A:
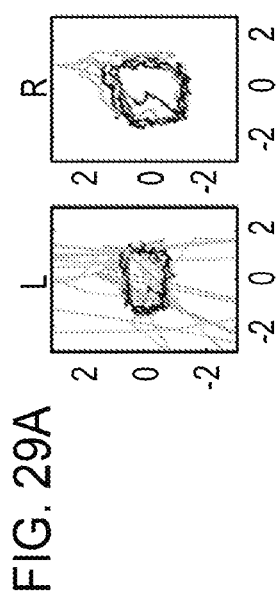
FIGS. 29A-D represent the findings from a 23 year old right-handed male who fell from height of 30 feet. The Patient was awake, alert and hypotensive in the field, GCS 14. He reported diffuse pain including in head, no vomiting. The neurological examination was non-focal, but the patient was intubated for chest and pelvis injuries. He had no ophthalmic history other than an optometric visit 6 months prior. He wears corrective lenses for astigmatism and reports a learning disability. Medications administered within 24 hours prior to eye tracking included albuterol, vancomycin hydrochloride, piperacilin tazobactam, aztreonam, pentacel.
Figure 29B:
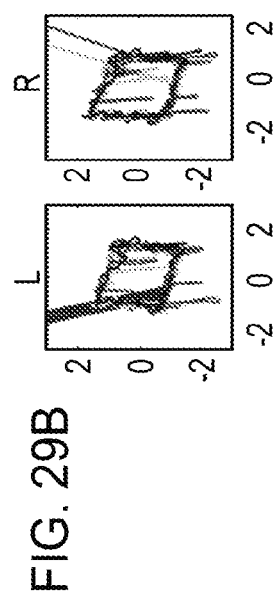
Figure 29C:
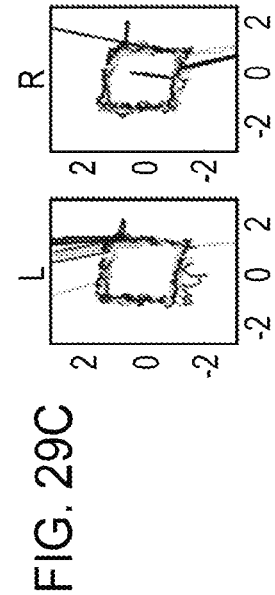
Figure 29D:
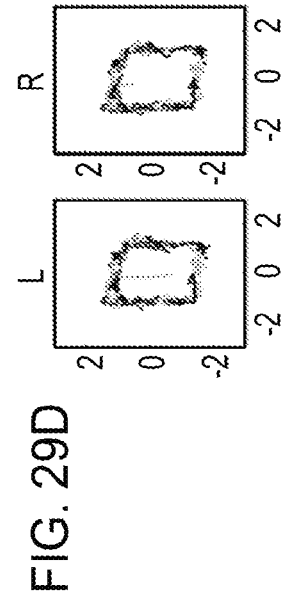
Figure 30A:
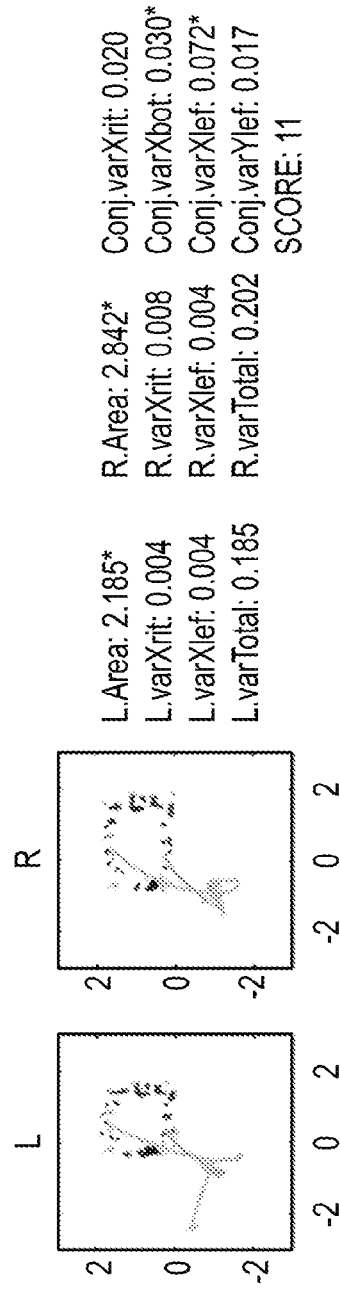
FIGS. 30A-B represent the findings from a 47 year old right-handed male recruited from the emergency room. The patient was inebriated and crashed his bicycle into a parked truck. He was unhelmeted. He vomited and then became unresponsive. Upon arrival, he was intubated, GCS 3T. Radiograph revealed a broken clavicle. Quantitative serum alcohol level was 284 mg/dl. He had no ophthalmic history following an optometric visit many years ago. Upon recruitment 24 hours later the patient was extubated, alert and oriented ×3. Medications administered up to 24 hours prior to recruitment included claritin and hydrocodone-acetaminophen, lidocaine, etomidate, and succinylcholine.
Figure 30B:
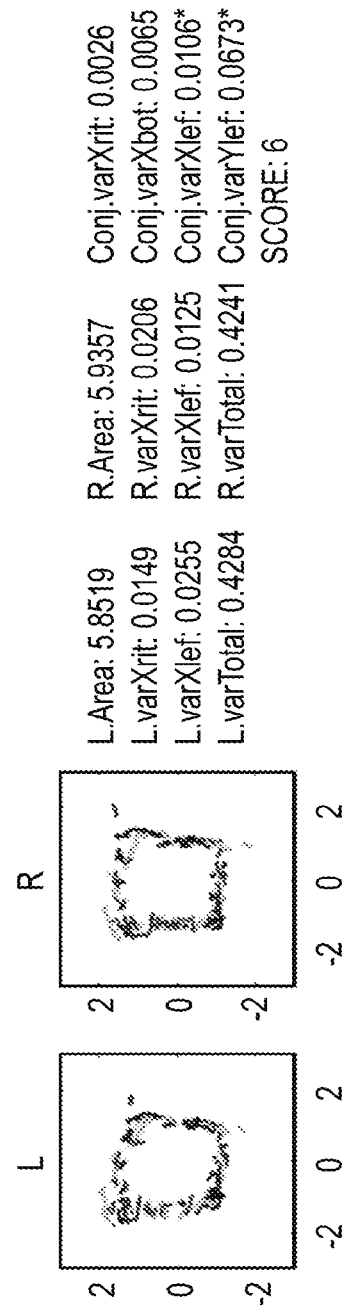
Figure 32:
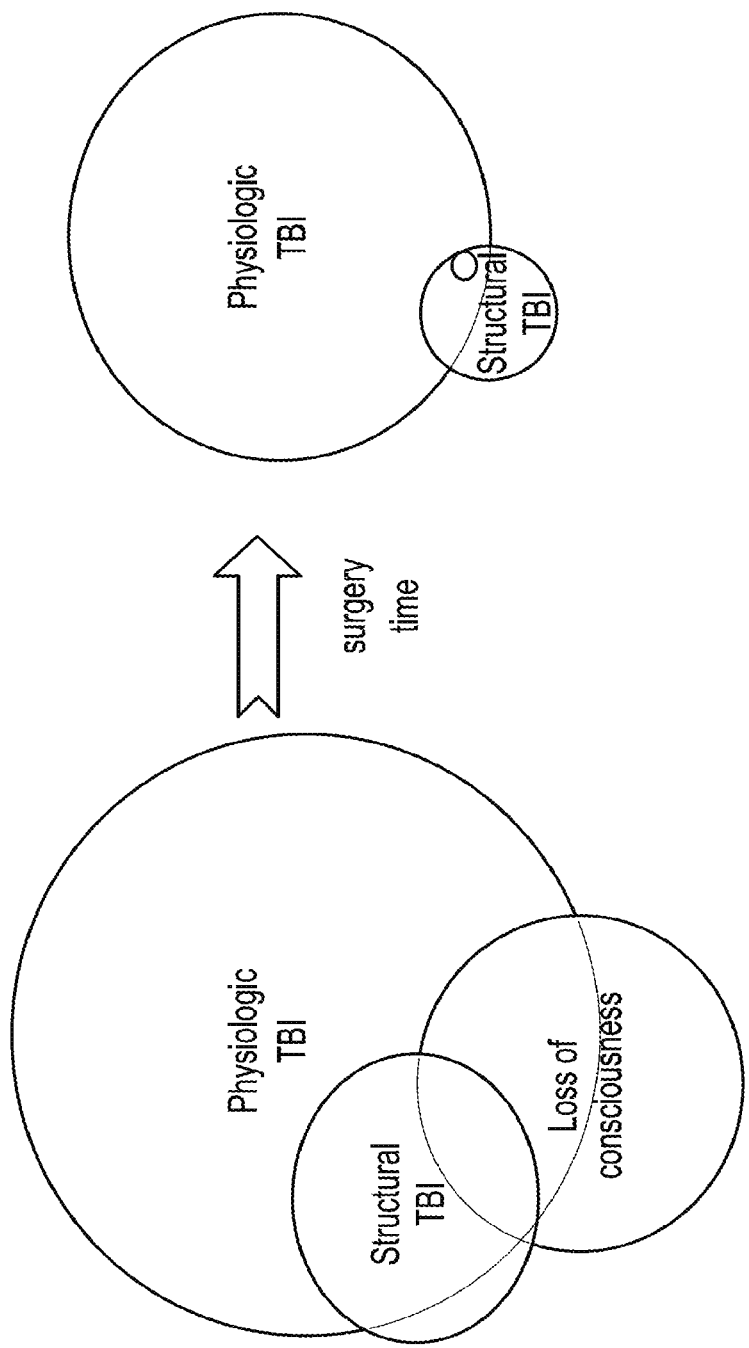
FIG. 32 represents graphically that while MRI and CT can detect structural traumatic brain injury (TBI), eye tracking can detect physiologic disruption of cerebral function.

A computing system according to the invention is described in FIGS. 13-14 Implementations of the observer matter and the functional operations described herein can be implemented in other types of digital electronic circuitry, or in computer software, firmware, or hardware, including the structures disclosed in this specification and their structural equivalents, or in combinations of one or more of them. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

Implementations of the observer matter and the operations described herein can be implemented in digital electronic circuitry, or in computer software, firmware, or hardware, including the structures disclosed in this specification and their structural equivalents, or in combinations of one or more of them. The observer matter described herein can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described herein can be performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the observer matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Described herein are many specific implementation details, these should not be construed as limitations on the scope of any inventions or of what may be claimed, but rather as descriptions of features specific to particular implementations of particular inventions. Certain features described herein in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

The Relationship of Aspect Ratio and Variance as Measures of the Signal

When the (x,y) pairs are plotted to show the 'box plots,' they have been preprocessed because the absolute values of the raw data are of limited use since changes in the signal over time are most important. There are many ways to normalize data, including dividing by the mean, by the standard deviation, or by the variance. Furthermore, the standard deviation or variance can be computed for all the data at once or x can be normalized using the variance of x and y can be normalized using the variance of y. Any normalization procedure for periodic data likely includes subtracting the mean, so the signal can be plotted as signal change alternating around zero. All of these transformations are conventional and widely used in data analysis by those of ordinary skill in the art. The details depend on the question being asked and the type of modeling or statistical testing being used.

In creating the box plots described herein, the raw data is preprocessed as follows: for the x (horizontal) and y (vertical) vectors independently, the mean is subtracted and divided by the standard deviation (which is the square root of the variance). This puts all the data in the same relative frame (zero-mean, max and min about 1 and −1). This is the reason the boxes look square (even if the stimulus presentation monitor is not square).

This means that 'long' and 'short' sides are reflecting relative variability. If the variability is high, the denominator is high and the measure value low. So, for example, if the variability of the horizontal (x) data is high relative to the variability of the vertical (y) data, the horizontal aspect of the box will be relatively smaller, and the result will be a tall skinny box (higher aspect ratio). Conversely, if the variability of the vertical (y) data is high relative to the variability of the horizontal (x) data, the vertical range will be reduced and the result will be a short fat box (lower aspect ratio).

Thus, particular implementations of the observer matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Disconjugate Eye Tracking Assessment

The methods described herein provide means for assessing or quantifying disconjugate gaze or disconjugate eye movement. These means feature receiving an array of pupil x and y coordinates that may be generated or obtained according to the methods described herein. These coordinates may be averaged across, for instance, five eyebox trajectory cycles. Formulaically this can be represented as follows:

$$X_{Avg,ik} = \frac{\sum_{j=1}^{5} X_{ijk}}{5}, \text{ for all } i = 1:N, k = 1:2,$$

where $X_{ijk}$ refers to the x-coordinate of the pupil, and k refers to the left or right eye of a subject. The difference in the x and y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero lateral or longitudinal pupil position difference between each eye. The variance may be computed as follows:

$$\text{Var}_x = \frac{1}{N} \sum_{i=1}^{N} (X_{Avg,i} - 0)^2.$$

The total variance may be computed as follows:

$$\text{Var}_{Tot} = \text{Var}_x + \text{Var}_y$$

The variance in X, Y, and the total variance may be plotted in order to assess the amount of disconjugation (i.e. disconjugate gaze) present in a subject.

Conjugacy of Eye Movement

The methods described herein may identify strabismus. In a population of 14,006 consecutive patients examined at a pediatric eye clinic in Rome, 2.72% demonstrated either A or V-pattern strabismus (Dickmann, et al., *Ophthalmic Epidemiol.*, 2012; 19: 302-305). A-pattern was associated with a greater prevalence of neurological impairment, hydrocephalus and meningomyelocele, while those with V-pattern exhibited a greater prevalence of craniosynostosis and malformative syndromes (Dickmann, et al., *Ophthalmic Epidemiol.*, 2012; 19: 302-305). Delays in treatment of strabismus onset following binocular vision maturation may be associated with permanent disruption of stereopsis and sensory fusion (Fawcett, *Curr Opin Ophthalmol.*, 2005; 16: 298-302).

Given the relatively low prevalence of strabismus, the methods described herein are useful for the rapid automated assessment of acquired disconjugacy. Such disconjugacy may be due to neurologic causes including trauma, hydrocephalus, demyelination, inflammation, infection, degenerative disease, neoplasm/paraneoplastic syndrome, metabolic disease including diabetes, or vascular disruption such as stroke, hemorrhage or aneurysm formation. Disconjugacy may also be due to ophthalmologic causes such as conjunctivitis, ophthalmoplegia, ocular injury or other diseases. The methods described herein may feature assessing conjugacy or disconjugacy of eye movement in correlation with structural and non-structural traumatic brain injury, including concussion or blast injury.

Structurally and Non-Structurally Brain Injured Subjects

A purpose of the prospective observational study described herein was to quantitate differences in eye tracking of structurally and non-structurally brain injured subjects relative to non-brain but bodily injured and healthy non-injured controls to identify the eye tracking parameters associated with structural and non-structural injury. Another purpose was to identify a correlation between impaired eye tracking and clinical neurologic functioning. Eye tracking and clinical concussion assessments were performed on 44 injured subjects, and eye tracking was performed only on 31 healthy normal controls. 51 eye tracking parameters were assessed in each patient. 10 parameters showed statistically significant differences between negative controls (healthy normal people and corporally injured trauma patients) and both positive controls (patients with structural brain injury) and patients with non-structural brain injury. 8 additional parameters showed statistically significant differences between negative controls (healthy normal people and corporally injured trauma patients) and patients with either structural or non-structural brain injury. 10 of the eye tracking measures showed statistically significant correlation between SCAT or SAC scores, demonstrating that these eye tracking parameters correlated with a validated clinical outcome measure.

In order to assess ocular motility including the function of cranial nerves III, IV, and VI and associated nuclei, a novel technique for automated eye movement tracking was developed using temporal rather than spatial calibration. The position of the pupil is predicted based on time elapsed since the start of the video rather than spatial calibration, enabling detection of impaired ability to move the pupil relative to normal controls or the opposite eye. Temporal calibration offers the additional advantage of utility to populations that may not be willing or able to cooperate with calibration instructions such as young children, foreign-language speakers, minimally conscious persons, or aphasics.

The data presented herein quantitates differences in eye tracking of structurally and non-structurally brain injured subjects relative to non-brain but bodily injured and healthy non-injured controls to identify the parameters associated with structural and non-structural injury. The data presented herein further establish a correlation between impaired eye tracking and clinical neurologic functioning.

General Quantification Methods

Raw x and y cartesian coordinates of pupil position are collected and stored in a one-dimensional vector:

$$x_i, \quad (1)$$

$$y_i, \quad (2)$$

This data is normalized according to the following form:

$$\bar{x}_i = \frac{x_i - \text{Mean}(x)}{\sigma_x}, \quad (3)$$

$$\bar{y}_i = \frac{y_i - \text{Mean}(y)}{\sigma_y}. \quad (4)$$

Index i corresponds to an individual data point. The size of i depends on the eye tracking hardware capture frequency and the time of tracking. The data is then sorted by eye (j=1:2, left, right), cycle (current stimulus method features an aperture that moves around the computer screen for five cycles) (k=1:5, first, second, third, fourth, fifth) and box segment (l=1:4, top, right, bottom, left). Implicit, is that each j, k, l has its own data points, n, whose size is also governed by the hardware tracking frequency and time length.

$$\bar{x}_i \to \bar{x}_{j,k,l}, \quad (5)$$

$$\bar{y}_i \to \bar{y}_{j,k,l}, \quad (6)$$

Individual Metrics
Segment Mean $$\bar{x}_{j,k,l}, \quad (7)$$

$$\bar{y}_{j,k,l}, \quad (8)$$

Corresponds to the arithmetic average of all data points on each segment l for all j, k. The result is one number representing each segment l.

Median

Corresponds to the statistical median of all data points on each segment l for all j, k. The result is one number representing each segment l.

$$\tilde{x}_{j,k,l}, \quad (9)$$

$$\tilde{y}_{j,k,l}, \quad (10)$$

Segment Variance $$\text{Var}(\bar{x}_{j,k,l}), \quad (11)$$

$$\text{Var}(\bar{y}_{j,k,l}). \quad (12)$$

Corresponds to the statistical variance of all data points on each segment l for all j, k. The result is one number representing each segment l.

Specific Metrics $$L.\text{varYtop} = \text{Var}(\bar{y}_{1,average\ k=1:5,1}) \quad (13)$$

$$R.\text{varYtop} = \text{Var}(\bar{y}_{2,average\ k=1:5,1}) \quad (14)$$

$$L.\text{varXrit} = \text{Var}(\bar{x}_{1,average\ k=1:5,2}) \quad (15)$$

$$R.\text{varXrit} = \text{Var}(\bar{x}_{2,average\ k=1:5,2}) \quad (16)$$

$$L.\text{varYbot} = \text{Var}(\bar{y}_{1,average\ k=1:5,3}) \quad (17)$$

$$R.\text{varYbot} = \text{Var}(\bar{y}_{2,average\ k=1:5,3}) \quad (18)$$

$$L.\text{varXlef} = \text{Var}(\bar{x}_{1,average\ k=1:5,4}) \quad (19)$$

$$R.\text{varXlef} = \text{Var}(\bar{x}_{2,average\ k=1:5,4}) \quad (20)$$

$$L.\text{varTotal} = \text{Average}(\text{Var}(\bar{x}_{1,average\ k=1:5}) + \text{Var}(\bar{y}_{1,average\ k=1:5})) \quad (21)$$

$$R.\text{varTotal} = \text{Average}(\text{Var}(\bar{x}_{2,average\ k=1:5}) + \text{Var}(\bar{y}_{2,average\ k=1:5})) \quad (22)$$

Segment Standard Deviation $$\sigma_{\bar{x}_{j,k,l}}, \quad (23)$$

$$\sigma_{\bar{y}_{j,k,l}}, \quad (24)$$

Corresponds to the statistical standard deviation of all data points on each segment l for all j, k. The result is one number representing each segment l.

Segment Skew $$\text{Skew}(\bar{x}_{j,k,l}) = \tilde{x}_{j,k,l} - \bar{x}_{j,k,l}, \quad (25)$$

$$\text{Skew}(\bar{y}_{j,k,l}) = \tilde{y}_{j,k,l} - \bar{y}_{j,k,l}, \quad (26)$$

Corresponds to the statistical skew (how far the mean is from the median) of all data points on each segment l for all j, k. The result is one number representing each segment l.

Specific Metrics $$L.\text{SkewTop} = \text{Skew}((\bar{y}_{1,average\ k=1:5,1}) \quad (27)$$

$$R.\text{SkewTop} = \text{Skew}((\bar{y}_{2,average\ k=1:5,1}) \quad (28)$$

$L.\text{SkewRit} = \text{Skew}((\bar{x}_{1,average\ k=1:5,2}))$ (29)

$R.\text{SkewRit} = \text{Skew}((\bar{x}_{2,average\ k=1:5,2}))$ (30)

$L.\text{SkewBot} = \text{Skew}((\bar{y}_{1,average\ k=1:5,3}))$ (31)

$R.\text{SkewBot} = \text{Skew}((\bar{y}_{2,average\ k=1:5,3}))$ (32)

$L.\text{SkewLef} = \text{Skew}(\bar{x}_{1,average\ k=1:5,4})$ (33)

$R.\text{SkewLef} = \text{Skew}(\bar{x}_{2,average\ k=1:5,4})$ (34)

Segment Normalized Skew $$SkewNorm(\bar{x}_{j,k,l}) = \frac{\text{Skew}(\bar{x}_{j,k,l})}{\sigma_{\bar{x}_{j,k,l}}},$$ (35)

$$SkewNorm(\bar{y}_{j,k,l}) = \frac{\text{Skew}(\bar{y}_{j,k,l})}{\sigma_{\bar{y}_{j,k,l}}}.$$ (36)

Specific Metrics $L.\text{SkewTopNorm} = \text{SkewNorm}(\bar{y}_{1,average\ k=1:5,1})$ (37)

$R.\text{SkewTopNorm} = \text{SkewNorm}(\bar{y}_{2,average\ k=1:5,1})$ (38)

$L.\text{SkewRitNorm} = \text{SkewNorm}(\bar{x}_{1,average\ k=1:5,2})$ (39)

$R.\text{SkewRitNorm} = \text{SkewNorm}(\bar{x}_{2,average\ k=1:5,2})$ (40)

$L.\text{SkewBotNorm} = \text{SkewNorm}(\bar{y}_{1,average\ k=1:5,3})$ (41)

$R.\text{SkewBotNorm} = \text{SkewNorm}(\bar{y}_{2,average\ k=1:5,3})$ (42)

$L.\text{SkewLefNorm} = \text{SkewNorm}(\bar{x}_{1,average\ k=1:5,4})$ (43)

$R.\text{SkewLefNorm} = \text{SkewNorm}(\bar{x}_{2,average\ k=1:5,4})$ (44)

Box Height $\text{BoxHeight}_{j,k} = \bar{y}_{j,k,1} - \bar{y}_{j,k,3}$ (45)

Box Width $\text{BoxWidth}_{j,k} = \bar{x}_{j,k,2} - \bar{x}_{j,k,4}$ (46)

Box Aspect Ratio $$AspectRatio_{j,k} = \frac{BoxHeight_{j,k}}{BoxWidth_{j,k}}$$ (47)

Box Area $\text{BoxArea}_{j,k} = \text{BoxHeight}_{j,k} \times \text{BoxWidth}_{j,k}$ (48)

Conjugacy

The five cycles are averaged together to give one averaged cycle, rendering:

$\bar{x}_{j,l},$ (49)

$\bar{y}_{j,l},$ (50)

Then the data from the right eye is subtracted from the left eye to obtain a delta value:

$\hat{x}_l = \bar{x}_{1,l} - \bar{x}_{2,l}$ (51)

$\hat{y}_l = \bar{y}_{1,l} - \bar{y}_{2,l}.$ (52)

Here x represents the left normalized raw x pupil position minus the right normalized raw x pupil position. 1 corresponds to the top, right, bottom and left segments of the box.

Variance (Conjugacy)

The variance here does not follow the traditional form of statistical variance. In the traditional form, the average of the data points is subtracted from the sum of individual data points. In this case, the average is forced to zero, thus inferring that the hypothetical control patient has perfect conjugacy (left and right eye move precisely together).

$$Conj\ varX = \text{Var}(\hat{x}) = \frac{\sum_{l=1}^{4}(\hat{x}_l)^2 - 0}{\sum_{l=1}^{4}\hat{x}_l},$$ (53)

$$Conj\ varY = \text{Var}(\hat{y}) = \frac{\sum_{l=1}^{4}(\hat{y}_l)^2 - 0}{\sum_{l=1}^{4}\hat{y}_l},$$ (54)

$TotalVariance = Conj\ totVar = \text{Var}(\hat{x}) + \text{Var}(\hat{y}),$ (55)

$$CoVariance = Conj\ CorrXY = \frac{\sum_{l=1}^{4}\hat{x}_l\hat{y}_l}{\sum_{l=1}^{4}\hat{x}_l - 1}$$ (56)

Specific Metrics $$Conj\ varXtop = \frac{\Sigma(\hat{x}_1)^2 - 0}{\Sigma\hat{x}_1},$$ (57)

$$Conj\ varXrit = \frac{\Sigma(\hat{x}_2)^2 - 0}{\Sigma\hat{x}_2},$$ (58)

$$Conj\ varXbot = \frac{\Sigma(\hat{x}_3)^2 - 0}{\Sigma\hat{x}_3},$$ (59)

$$Conj\ varXlef = \frac{\Sigma(\hat{x}_4)^2 - 0}{\Sigma\hat{x}_4},$$ (60)

$$Conj\ varYtop = \frac{\Sigma(\hat{y}_1)^2 - 0}{\Sigma\hat{y}_1},$$ (61)

$$Conj\ varYrit = \frac{\Sigma(\hat{y}_2)^2 - 0}{\Sigma\hat{y}_2},$$ (62)

$$Conj\ varYbot = \frac{\Sigma(\hat{y}_3)^2 - 0}{\Sigma\hat{y}_3},$$ (63)

$$Conj\ varYlef = \frac{\Sigma(\hat{y}_4)^2 - 0}{\Sigma\hat{y}_4}$$ (64)

$$Conj\ CorrXYtop = \frac{\Sigma\hat{x}_1\hat{y}_1}{\Sigma\hat{x}_1 - 1},$$ (65)

$$Conj\ CorrXYrit = \frac{\Sigma\hat{x}_2\hat{y}_2}{\Sigma\hat{x}_2 - 1},$$ (66)

$$Conj\ CorrXYbot = \frac{\Sigma\hat{x}_3\hat{y}_3}{\Sigma\hat{x}_3 - 1},$$ (67)

$$Conj\ CorrXYlef = \frac{\Sigma\hat{x}_4\hat{y}_4}{\Sigma\hat{x}_4 - 1}$$ (68)

Variance x Ratio Top/Bottom (Conjugacy)

$$Conj\ varXtopbotRatio = \frac{\text{Var}(\hat{x}_1)}{\text{Var}(\hat{x}_3)}$$ (69)

Variance y Ratio Top/Bottom (Conjugacy)

$$Conj\ varYtopbotRatio = \frac{Var(\hat{y}_1)}{Var(\hat{y}_3)} \quad (70)$$

Variance x Ratio Left/Right (Conjugacy)

$$Conj\ varXlefritRatio = \frac{Var(\hat{x}_4)}{Var(\hat{x}_2)} \quad (71)$$

Variance y Ratio Left/Right (Conjugacy)

$$Conj\ varYlefritRatio = \frac{Var(\hat{y}_4)}{Var(\hat{y}_2)} \quad (72)$$

EXAMPLES

The following examples are set forth to provide those of ordinary skill in the art with a description of how to make and use the methods and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Background

Eye movements contain clinically important information about neurological integrity. Clinical devices may take advantage of the relative ease of automated eye-movement tracking, for applications such as assessing recovery following clinical intervention. A technique was designed that can reliably measure eye movements with precision, without initial spatial calibration. We tracked eye movements without spatial calibration in neurologically intact adults and in neurosurgical patients as they watched a short music video move around the perimeter of a screen for 220 s. Temporal features of the data were measured, rather than traditional spatial measures such as accuracy or speed.

The methods reliably discriminated between the presence and absence of neurological impairment using these uncalibrated measurements. The results indicate that this technique may be extended to assess neurologic integrity and quantify deficits, simply by having patients watch TV.

These methods are useful in a number of contexts, including rapid assessment of potentially neurologically injured individuals, monitoring of patients whose states might fluctuate between impairment and recovery, and measuring the efficacy of rehabilitation or intervention.

Eye movements have long been known to contain clinically relevant information about neurological integrity. Assessment of ocular motility is a standard part of any neurological exam, because it is easy and informative. However, there are some problems with the standard clinical exam including that it is nominally administered by an expert, and generally is only qualitative, not quantitative.

The relative ease, portability, and noninvasiveness of automated eye-movement tracking devices has made it a promising area of translational research, for applications such as testing for concussion on athletic fields and assessing recovery following clinical intervention. Eye movement studies have provided insight into clinical fields from psychiatry to traumatic brain injury (TBI) and rehabilitation, (Trojano, et al., J Neural., 2012, 259(9):1888-95; Gitchel, et al., Arch Neurol., 2012, 69(8):1011-7; Qiu, et al., PLoS One, 2011, 6(10):e25805; Plow, et al., PMR, 3(9):825-35; Heitger, et al., Brain., 2009, 132 (Pt 10):2850-70; Pearson, et al., Br J Sports Med., 2007, 41(9):610-2; Heitger, et al., J Neural Sci., 2007, 15; 253 (1-39 2):34-47; Suh, et al., Neurosci Lett., 2006, 401 (1-2):108-13; Suh, et al., Neurosci Lett., 2006, 410(3):203-7; Heitger, et al., Brain Inj., 2006, 20(8): 807-24; Yang, et al., Image and Vision Computing, 2002, 20(4):273-87; and Heitger, et al., Prog Brain Res., 2002, 40:433-12 48) Studies commonly measure accuracy of spatial fixation, time spent on particular fixation targets, and saccade count. (Trojano, et al., J Neurol., 2012, 259(9): 1888-95 and Foulsham, et al., Vision Res., 2011, 51(17): 1920-31) Despite the promise, it has proven difficult to develop clinical applications based on quantitative measurements of eye-movements, (Heitger, et al., Prog Brain Res., 2002, 40:433-12 48 and Foulsham, et al., Vision Res., 2011, 51(17):1920-31) possibly because spatial calibration can be difficult in clinical settings, and because spatial calibration precludes the use of eye tracking for detection of dysfunctional ocular motility.

The standard use of an eye-tracker requires that the system be calibrated individually for every observer at the start of every measurement session. Calibration involves asking the observer to look at a series of high-contrast dots displayed on a computer monitor. The calibration process may be repeated several times until sufficient accuracy has been achieved. Only then can eye movements be recorded.

It has been difficult to use eye-tracking in clinical applications with observers for whom this calibration process is difficult (e.g., requiring many repetitions) or impossible. Calibration requires a willing observer who can follow commands reliably. Many clinical conditions that result in a loss of neural integrity, such as stroke or brain injury, also render the observer unwilling or unable to follow instruction.

Also problematic for using eye-tracking methods to brain injury or stroke patients, the calibration process itself may reduce the sensitivity of the eye tracking test. For example, consider a patient with impaired vertical ocular motility. Because the calibration process assumes that the eyes cover the full range of locations mapped out by the calibration points, it assigns the maximum pupil angle up and down incorrectly to the 'top' and 'bottom' of the monitor, respectively. In such instances, all future measurements for that observer are adjusted to conform to that incorrect assignment. Thus, impaired ocular motility may be undetected in tests that begin with a spatial calibration of the eye tracker.

Eye movement measurements may reflect severity of damage to the brain, as well as recovery following clinical intervention. The methods described herein were used to test patients from neurosurgery, emergency department and ophthalmology clinics as well as a control set of healthy volunteers. The success of the method involves two features. First, the methods described herein do not use spatial measures of accuracy as a variable of interest. By looking at eye movement trajectories in the time domain rather than the spatial domain, it is possible to quantify measures that do not rely on spatial calibration. Second, the measures are easily visualized and evaluated, making them immediately useful to the clinician or researcher.

Methods

Subjects. Healthy observers were recruited in New York University according to IRB approved protocols as determined by the University Committee on Activities Involving Human Subjects (UCAIHS). All participants provided written informed consent, and the consent forms were approved by UCAIHS. Patients with neurological deficit were recruited from the neurosurgical practice at Bellevue Hospital. Written informed consent from the subjects or their legal proxies were obtained for prospective data collection according to guidelines established by the NYU IRB.

Observers. Because of the potential for uncalibrated eye-tracking to serve as an initial screen, the patient population was not restricted to a specific pathology. Rather, an arbitrary sample of patients who came through the clinic was recruited. The resulting sample was representative of the range of disorders seen in the clinic.

Eye Movement Tracking. Observers' eye movements were recorded using an Eyelink 1000 binocular eye tracker (500 Hz sampling, SR Research). All observers were seated approximately 55 cm from the screen. Some test patients were tracked on multiple visits at different stages of diagnosis, surgery, and recovery.

Visual Stimulus. The visual stimulus provided as a music video that played continuously while it moved clockwise along the outer edges of a computer monitor. Observers were instructed to watch the video. The stimulus was expected to evoke smooth pursuit eye movements as well as possible saccades and microsaccades as the observers scanned the video. The video was presented in a square aperture with an area approximately ⅛ of the size of the screen (about 16° of visual angle). This square aperture started at the upper left hand corner of the screen and moved at a constant speed, taking 10 seconds to traverse each edge of the monitor. A full cycle took 40 seconds, and five full cycles were played, for a total of 200 seconds. A countdown video played in the starting position for 10 seconds before the music video began, to give observers time to orient to the stimulus. Only the 200 seconds of the music video were used for analyses. The eye tracker sampled eye position at 500 Hz, yielding 100,000 samples of eye position over 200 seconds.

Axis Orientation. The camera and monitor were securely mounted, so that 'horizontal' for the camera was the same as 'horizontal' for the monitor. Therefore, the terms 'horizontal' and 'vertical' are defined with respect to the monitor, not with respect to head-tilt. However, the head was typically aligned with the monitor, and a chinrest was used with all controls and about half of the patients, to ensure the continued alignment. The eyetracker converted changes of pupil angle into two orthogonal components which it labeled x, and y, and which in turn referred to horizontal and vertical change, due to the linked orientation of the monitor and camera. Therefore, we also refer to horizontal and vertical components as x and y respectively.

Data preprocessing. There was no spatial calibration so the units of the raw timecourses were of limited value. Therefore, for each observer, the timecourses were normalized by subtracting the mean and dividing by the standard deviation. This was done for each timecourse independently. The different timecourses were treated as distinct data sets from the same test patient or neurologically intact control.

Timecourses. The normalized x- and y-timecourses were plotted across time (FIGS. 1A and B). The clockwise movement of the visual stimulus alternated between horizontal changes and vertical changes, and the x- and y-timecourses in neurologically intact observers show the same alternation.

Visualization: Scatterplots. For visualization, scatterplots of the entire time series were created by plotting the 100,000 (x,y) pairs representing the two orthogonal components of the instantaneous angle of pupil reflection over 200 seconds. In neurologically intact controls, these figures look like boxes, reflecting the timing of the visual stimulus as it moved around the screen.

Quantitative data analysis and statistics. The x- and y-trajectories were fit with sinusoidal functions. The alternations in horizontal and vertical motion of the visual stimulus were thought to result in eye movement trajectories that were approximately sinusoidal with a period of 40 s, but with different phases for x and y. We further hypothesized that (1) the phase difference between x and y should be 45 degrees for neurologically intact controls, reflecting the ¼ cycle alternation of horizontal and vertical eye movements; and (2) the model would fit data from the neurologically intact control observers better than it fit data from the patient group.

Degree of correlation (r) with a sinusoid was calculated for 1 each time course. The square of this value (r2) is a measure of goodness of fit of the model to the data. The correlation values were used because they better suited for statistical analysis. Throughout the text, 'model fit' refers to the correlation values (r).

Phase was calculated as phase of the sine function that best fit the data. The 8 following complementary procedures were used to assess the statistical significance of any differences in these two measures (phase difference and model fit) as compared between the neurologically intact control observers and the test patient observers.

(i) Statistical Analysis 1: hypothesis testing. For each measure, a statistical test was performed to determine whether the data from the test patient population could have come from the same underlying distributions as the data from the neurologically intact control population. For the phase measure, an unpaired t-test was used. For the sinusoidal fit measure, the Kruskal-Wallis analysis of variance (ANOVA) was used which is more appropriate for data that are not normally distributed.

(ii) Statistical Analysis 2: Fisher transformation. The correlation (r) values for each timecourse with the best fitting sinusoid were converted to z-scores using the Fisher transformation $((½)*\ln((1+r)/(1-r)))$. This normalization enables to complete the third step of the analysis.

(iii) Statistical Analysis is classification. The Fisher z-scores provided an estimate of the probability of seeing a particular correlation value for a given timecourse if the underlying population of timecourses had zero mean correlation (the null hypothesis). The null hypothesis would be expected to be true for timecourses that were not fit well by sinusoids, e.g., timecourses from impaired observers. Timecourses with z-scores significantly above zero (e.g., well-matched to the stimulus trajectory) would be expected to come from unimpaired observers. A threshold of z=2 (corresponding to a significance level of alpha=0.05) was used to calculate the specificity and sensitivity of this test, as reported in the Results following.

Results

Eye movements were highly reliable and consistent across the group of neurologically intact control observers ( ).

Discussion

Uncalibrated tracking may provide a quantitative measure of the ability to fixate, attend, and follow a stimulus. These date demonstrate that it is possible to collect reliable high-frequency eye movement data without first completing a spatial calibration for each observer. Many patients are not capable of calibrated eye tracking. The ability to track eye movements in these populations provides new insights about a variety of disorders that disturb the ocular-motor system, including but not limited to brain injury, stroke, and psychiatric disorders. Possible applications include clinical screening, diagnosis, monitoring the efficacy of treatment, and tracking progression of impairment and recovery.

Example 2

Materials and Methods

Subjects. Healthy subjects were recruited in a university setting in accordance with IRB approved protocols. All other subjects were recruited directly from our neurosurgical practice. Informed consent from the subject or their legal proxy was obtained for prospective data collection in all cases in accordance with IRB guidelines.

Eye Movement Tracking. The subjects' eye movements were recorded using an Eyelink 1000 binocular eye tracker (500 Hz sampling, SR Research). Healthy volunteers were seated 55 cm from the screen with their head stabilized using a chinrest. Stimulus was presented on average 55 cm from patient eyes, with the presentation monitor adjusted to match gaze direction. Subjects used a chinrest.

Innovations for tracking patients. Two innovations were provided to measure ocular motility in a patient population. The first was a paradigm, consisting of a stimulus and an analysis stream that allows interpreting raw eye position data. With few exceptions, eye movement studies analyze transformed gaze position, which involves a loss of information and excludes many patients from study. A novel algorithm for looking at pupil position directly, yielding information about ocular motility was developed. A device that can be brought to patients was provided. With few exceptions, eye movement data are collected using a fixed eye tracker at an unchanging location, which requires subjects to travel to the tracker and to use the chair and chinrest setup that goes with it. The SR Research Eyelink 1000 was adapted into a novel mobile system that allows flexibility in location and subject position, without sacrificing data quality.

Visual Stimulus. A music video that moved clockwise along the outer edge of a computer monitor starting at the upper left hand corner of the screen was provided. Spatial calibration was not performed, and the distance varied between subjects, so that the size of the stimulus in degrees may only be approximated. For a healthy subject seated 55 cm from the screen with good spatial calibration, the stimulus was presented in a square aperture with an area of approximately 16 degrees (approximately ⅛ of the size of the screen). This square aperture, within which a music video played continuously, moved across the screen at a constant speed, taking 10 s to cover each edge of the monitor. A full cycle took 40 s, and five full cycles were played, for a total of 200 s. A countdown video played in the starting position for 10 s before the music video began, to provide all subjects time to orient to the stimulus. The movie continued for an addition 10 seconds after the 200 s trial, to avoid boundary effects from contaminating the data. Only the 200 s of the music video comprising 5 cycles of 40 s each were used in all analyses. At a rate of 500 Hz, this yielded 100,000 samples of eye position over 200 seconds.

Data analysis: (1) Visualization. To create a snapshot of the data from the entire trial that provided a vivid indication of whether an individual subject's ocular motility differs from that of healthy controls, scatterplots of the entire time series were created by plotting the horizontal eye position along one axis and vertical eye position along the orthogonal axis. The 100,000 pairs of values (x,y) were plotted representing the two components of the instantaneous angle of pupil reflection (horizontal, vertical) over 200 seconds. In healthy controls, these figures look like boxes, reflecting the trajectory traveled by the aperture as it moved across the screen. These visualizations confirmed that the raw eye traces did conform to the square spatial trajectory of the stimulus, except in cases of neurological damage.

Data analysis: (2) Time vs. Space. Without spatial calibration, exact measurements of error in the spatial domain are impossible. This problem was avoided by looking at the eye movement trajectories in the time domain, rather than the spatial domain. By using a constantly changing stimulus (a continuously playing movie) with a periodic envelope (the aperture trajectory), it was possible to look at relative eye movements over time. Effectively, each subject's mean trajectory over the path of the aperture served as its own calibration.

Data analysis: (3) Statistics. In order to quantitatively assess the statistical significance of our results, the distribution of certain measurements in the control population was determined, and each subject was compared with these control distributions for each measure. The stimulus trajectory was divided into four time components: The first arm consisted of five repetitions of the first 10 seconds of each rotation cycle (e.g., seconds 1:10, 41:50, 81:90, 121:130, and 161:170). The second, third and fourth arms were defined accordingly. Two variables were evaluated: the relative variance in each arm, and the relative integrity of each arm. Relative variance was calculated as mean variance across 5 repetitions within an arm divided by variance of the whole time course. Integrity was calculated as the percent of missing values in each arm. We defined 2 tests based on these measurements, and performed the same tests in the controls and the patients. The results of these tests in the control population were used to determine the control distributions. The results of these tests for each patient were compared to the appropriate control distribution, and confidence intervals were defined as follows.

Integrity. For the integrity measure, each patient's pair of values from arms 1 (the top of the box) and 3 (the bottom of the box) was z-scored using the mean and standard deviation calculated from the control population. The resulting score indicated how different the patient values were compared with the control values, in units of standard deviations. Because 95% of all values in a normal distribution lie within two standard deviations of the mean, a z-score of 2 was used as a significance threshold. Patients with z-scores above 2 in either or both arms were thus judged to have significant disturbances of ocular motility.

Relative variance. Because relative variance is a ratio, it cannot be analyzed using z-scores, since the assumption of a normal distribution does not hold for ratios. Instead, 5,000 point distributions were generated using a bootstrapping method that took 5,000 samples from 25 values randomly chosen with replacement from the 45 control values. For each subject, the relative variance in arms 1 and 3 were compared respectively with the corresponding control distribution, and the percent of the control distribution with variance below that of the test value was determined. A p-value of 0.05 (a widely accepted measure of statistical significance) corresponds to 95% of control values falling below the test value. Thus, subjects with variance higher than 95% of the values in the control distributions were determined to have significant disturbances of ocular motility.

Units. The units of relative variance are related to size in degree of visual angle, but are not exactly identical to degrees of visual angle, because there was no spatial calibration. These may be referred to as time-degrees units.

Results

Successful tracking. Visualization of the eye movement trajectories across healthy controls and patients confirmed that the method successfully measured eye movements without recourse to traditional calibration techniques.

Control distributions. As expected, the control distributions for the integrity measurements were normally distributed with a mean of 0.2 and an average standard deviation of 0.05 (5% deviation). The control distributions of relative variance peaked at 0.25 (reflecting equal variance across the four arms).

Patient measurements. The integrity measures for the 'top' vs. 'bottom' arms of the trajectory for each subject, in units of standard deviation, as compared with the control distributions as described above were calculated. Subjects with cranial nerve palsies or mass effect showed defects in integrity of eye tracing box trajectory. Subjects with relatively greater cranial nerve II palsies due to either compression or papilledema showed streaking vertical lines due to scanning vision.

Example 3

Materials and Methods

Patient Selection. Control subjects were employees, volunteers, visitors and patients at the Bellevue Hospital Center recruited in accordance with Institutional Review Board policy. Inclusion criteria for normal control subjects were: age 7 to 100 years, vision correctable to within 20/500 bilaterally, intact ocular motility, and ability to provide a complete ophthalmologic, medical and neurologic history as well as medications/drugs/alcohol consumed within the 24 hours prior to tracking. Parents were asked to corroborate details of the above for children aged 7-17. Exclusion criteria were history of: strabismus, diplopia, palsy of cranial nerves III, IV or VI, papilledema, optic neuritis or other known disorder affecting cranial nerve II, macular edema, retinal degeneration, dementia or cognitive impairment, hydrocephalus, sarcoidosis, myasthenia gravis, multiple sclerosis or other demyelinating disease, and active or acute epilepsy, stroke/hemorrhage or brain injury sufficiently significant to result in hospitalization. Subjects reporting any minor brain injury regardless of loss of consciousness within the previous week were also excluded.

Additional subjects were recruited from a neurophthalmic practice also in accordance with Institutional Review Board policy. These subjects were selected for participation specifically because they had known palsies of cranial nerves III, IV and VI respectively, or other specific ocular pathology.

Visual Stimulus. Each subjects' eye movements were recorded with an Eyelink 1000 eye tracker at a fixed distance of 55 cm from a computer monitor over a time period of 220 seconds. For the stationary tracker the subject was seated in an adjustable height chair, using an adjustable height chinrest. Portable tracker subjects were seated in either a height adjustable or height-fixed chair, with the monitor height adjusted to the subject. The portable tracker chinrest was attached to the monitor, while the stationary tracker chinrest was attached to the same table as the computer monitor. The visual stimuli were the music videos Shakira Waka-Waka, K'naan Wavin' Flag, or the Under the Sea song from the Little Mermaid. The video was played continuously in a square aperture with an area approximately ⅛ the screen size while moving clockwise along the outer edges of the monitor for five complete cycles of 40 seconds each. The first and last 10 seconds of each data set were discarded to yield 200 seconds of data. The afferent stimulus was presented binocularly and eye tracking was performed binocularly. Subjects were not spatially calibrated to the tracker to enable independent analysis of each pupil position over time.

In a separate example, subjects were assessed for gaze conjugacy using a naturalistic viewing stimulus. This consisted of watching television as eye movements were tracked over time. Subjects were not seated at a fixed distance from the monitor but were able to move their heads during viewing.

Data Analysis. The eye tracker sampled pupil position at 500 Hz, yielding 100,000 samples over 200 seconds. Scatterplots of the entire time series were created by plotting the 100,000 (x, y) pairs representing the two orthogonal components of the instantaneous angle of pupil reflection over time to create 'box trajectories' that reflected the temporal nature of the pupillary movement. These figures look like boxes, reflecting the timing of the aperture as it moved around the screen.

Analysis of Gaze Conjugacy. Comparing the movement of one eye of a subject to the other eye of a subject was performed by comparing the x, y Cartesian coordinates at any time point t. For example by subtracting the x coordinate of the left eye from the x coordinate of the right eye or vice versa. Also by subtracting the y coordinate of the left eye from the y coordinate of the right eye or vice versa. The sums of the differences between all of the x coordinates over the time tested informs regarding horizontal movement of the pupil. The sums of the differences in y coordinates over time informs regarding vertical movement of the pupil. The total sum of the differences between both x and y coordinates over the time tested can be summed to obtain a measure of total disconjugacy of gaze, or as an average of five eyebox trajectory cycles formulaically represented as follows:

$$X_{Avg,ik} = \frac{\sum_{j=1}^{5} X_{ijk}}{5}, \text{ for all } i = 1:N, k = 1:2,$$

where $X_{ijk}$ refers to the x-coordinate of the pupil, and k refers to the left or right eye of a subject. In cases where a subject's data was missing at any given time point in the five cycles, the denominator of the equation was the number of cycles where the data was present. The difference in the x and y position, for the left and right eye, may then be computed. This vector of difference may then be plotted graphically for purposes of assessment and interpretation. To have a single metric expressing the level of pupil disconjugation, a variance of the data may be computed with respect to an expected mean of zero. This is significant because the code assumes that a healthy subject has zero vertical or horizontal pupil position difference between each eye. The variance for either horizontal (x) or vertical (substitute y for x) movement may be computed as follows:

$$\text{Var}_x = \frac{1}{N}\sum_{i=1}^{N}\left([X]_{Avg,i1} - X_{Avg,i2}\right) - 0)^2$$

The total variance in both the horizontal and vertical planes may be computed as follows:

$$\text{Var}_{Tot} = \text{Var}_x + \text{Var}_y.$$

The variance in X, Y, and the total variance may be plotted in order to assess the amount of disconjugation present in a subject.

Statistical Analyses

Statistics were evaluated using R. Conjugacy of eye movement versus age: Normal subjects demonstrated conjugate eye movement that was not impacted by age. A linear regression between total variance and age was calculated. A linear regression t-test was used to determine whether the slope of the regression line was statistically significantly different from 0.

Conjugacy of eye movement compared between genders: A Welch Two Sample t-test was used to determine if the true difference between the mean of male total variance and the mean of female total variance was statistically significantly different from 0.

X (horizontal eye movement) versus Y (vertical eye movement) conjugacy: A paired t-test was used to determine if the mean of the subject-paired differences between the total x-variance and total y-variance was statistically significantly different from 0.

Test-retest on the stationary tracker and from the stationary to the portable tracker: A paired t-test was used to determine if the mean of the subject-paired differences between the total variances for two separate eyetracking sessions was statistically significantly different from 0.

Results 125 unique subjects aged 7 to 75 (mean 34.3±15.7, median 28.2; 51.2% female) were surveyed regarding their past medical history (Table 1), past ophthalmic history (Table 2) and any medications, alcohol or drugs of abuse (Table 3) taken within the last 24 hours. The results indicated that many subjects disclosed prior medical and ophthalmic history and medication usage.

TABLE 1

Neurologic/Cranial History

| Condition/Symptoms | Number of Subjects |
|---|---|
| Concussion | 9 |
| Migraines | 4 |
| Hypertensin | 3 |
| Hypothyroidism | 3 |
| Unspecified Head injury | 3 |
| Vertigo | 2 |
| Diabetes Melitus | 1 |
| Dyslexia | 1 |
| Spinal Injury | 1 |
| 7, 8 Palsy | 1 |

*Note:
Subjects may exhist in Multiple Categories

TABLE 2

Ophthalmic History

| Condition/Symptoms | Number of Subjects |
|---|---|
| Myopia | 25 |
| Astigmatism | 9 |
| Hyperopia | 6 |
| Cataracts | 5 |
| Glaucoma | 2 |
| Keratosis | 2 |
| Retinal Detachment | 2 |
| Adie Syndrome | 1 |
| Chalzion | 1 |
| Corneal Ulcers | 1 |
| Lasik | 1 |
| Orbital Myositis | 1 |
| Presbyopia | 1 |
| Sty | 1 |
| Trauma from foreign object | 1 |
| Other, unspecified | 9 |

*Note:
Subjects may exhist in Multiple Categories

TABLE 3

Medication/Drug Usage in last 24 hrs

| Drugs | Number of Subjects |
|---|---|
| Multivitamin | 11 |
| Synthriod | 5 |
| Vitamin D | 5 |
| Aspirin | 6 |
| Advil | 3 |
| Lisinopril | 3 |
| Lipitor | 3 |
| Simvastatin | 3 |
| Adderall | 2 |
| Calcium | 2 |
| Flovent | 2 |
| Hydrocholorthiazide | 2 |
| Imuran | 2 |
| Insulin (unspecified) | 2 |
| Laxapro | 2 |
| Metoprolol | 2 |
| Norvasc | 2 |
| Spironolactone | 2 |
| Yaz | 2 |
| Albuterol | 1 |
| Allegra | 1 |
| Vitamin B12 | 1 |
| Calcitriol | 1 |
| chondroitin | 1 |
| Citrucel | 1 |
| Clopidogrel | 1 |
| Colcrys | 1 |
| Concerta | 1 |
| Cordia | 1 |
| Diovan | 1 |
| Doxycycline | 1 |
| Esomeprazole | 1 |
| Ferrous Sulfate | 1 |
| Fish Oil | 1 |
| Flonase | 1 |
| Furosemide | 1 |
| Gabapentin | 1 |
| Glyburide | 1 |
| Hydrocortisone | 1 |
| Kombigyze XR | 1 |
| Lantus | 1 |
| Losartan | 1 |
| Lutera | 1 |
| Magnesium Oxide | 1 |
| Methimazole | 1 |
| Motrin | 1 |
| Nexium | 1 |
| Niquil | 1 |
| Nit D | 1 |

TABLE 3-continued

Medication/Drug Usage in last 24 hrs

| Drugs | Number of Subjects |
|---|---|
| Novolog | 1 |
| OCP (unspecified) | 1 |
| Omezaprole | 1 |
| Plavix | 1 |
| Prandin | 1 |
| Prilosec | 1 |
| Singulair | 1 |
| Stribild | 1 |
| Toprol | 1 |
| Trimo-San | 1 |
| Welbutrin | 1 |
| Xyzal | 1 |
| Zyprexa | 1 |
| Zyrtec | 1 |
| Admit to Marijuana | 1 |
| Admit to Alcohol in past 24 | 6 |

*Note:
Subjects may exhist in Multiple Categories

Figure 7:
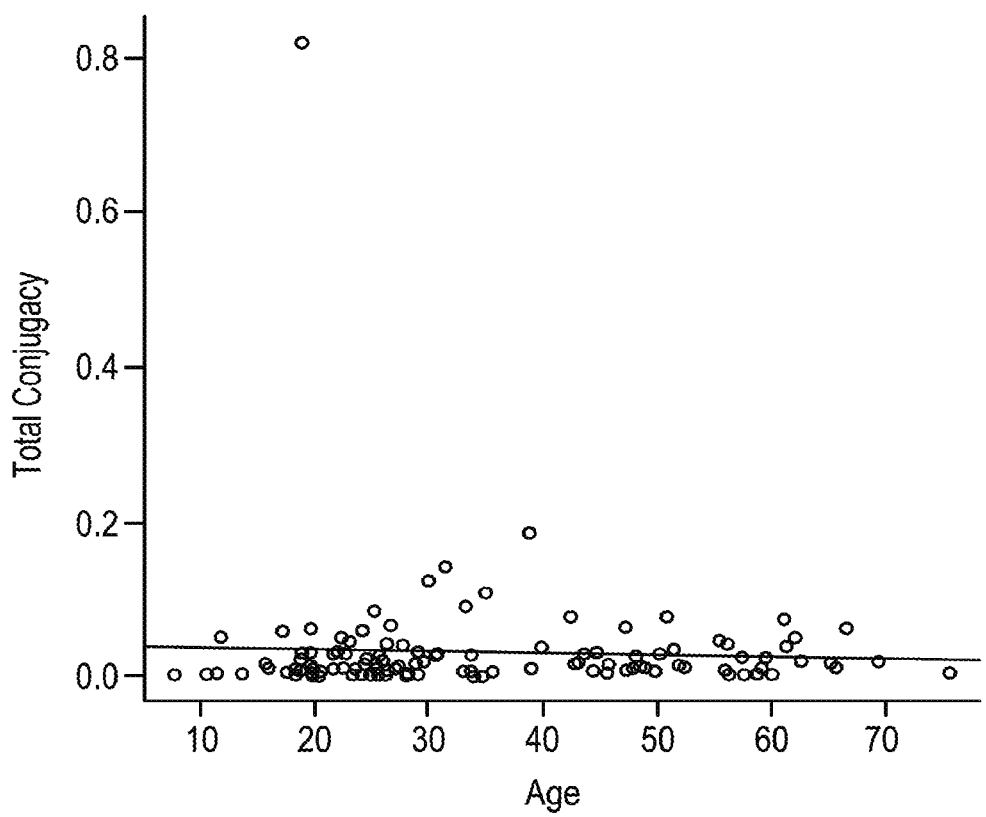
FIG. 7 represents total conjugacy versus age. Normal subjects demonstrated conjugate eye movement that was not impacted by age. A linear regression t-test was used to determine whether the slope of the relationship between total variance and age yielded a regression line statistically significantly different from 0. The test resulted in a t-statistic of −0.523 and a p-value of 0.6017 showing that the slope of the regression line was not statistically significantly different from 0. Thus in our subject population ranging in age from 7 to 75, there was no change in conjugacy of eye movements with age.

Normal subjects demonstrated conjugate eye movement that was not impacted by age (FIG. 7). A linear regression t-test was used to determine whether the slope of the relationship between total variance and age yielded a regression line statistically significantly different from 0. The test resulted in a t-statistic of −0.523 and a p-value of 0.6017 showing that the slope of the regression line was not statistically significantly different from 0. Thus in the subject population ranging in age from 7 to 75, there was no change in conjugacy of eye movements with age.

The single greatest outlier (conjugacy of 0.8214) in the control population was a 23 year old male student who wears corrective contact lenses and takes adderal for attention deficit and hyperactivity disorder. This subject underwent repeat tracking which remained disconjugate, (0.2600) however less than previously. The second greatest outlier (conjugacy 0.486) was a 39 year old male hospital employee who denied any ophthalmic or medical history, as well as the use of alcohol or drugs in the prior 24 hours. In both of these subjects the X-conjugacy was not a statistical outlier and only the y coordinates were disconjugate.

Figure 8:
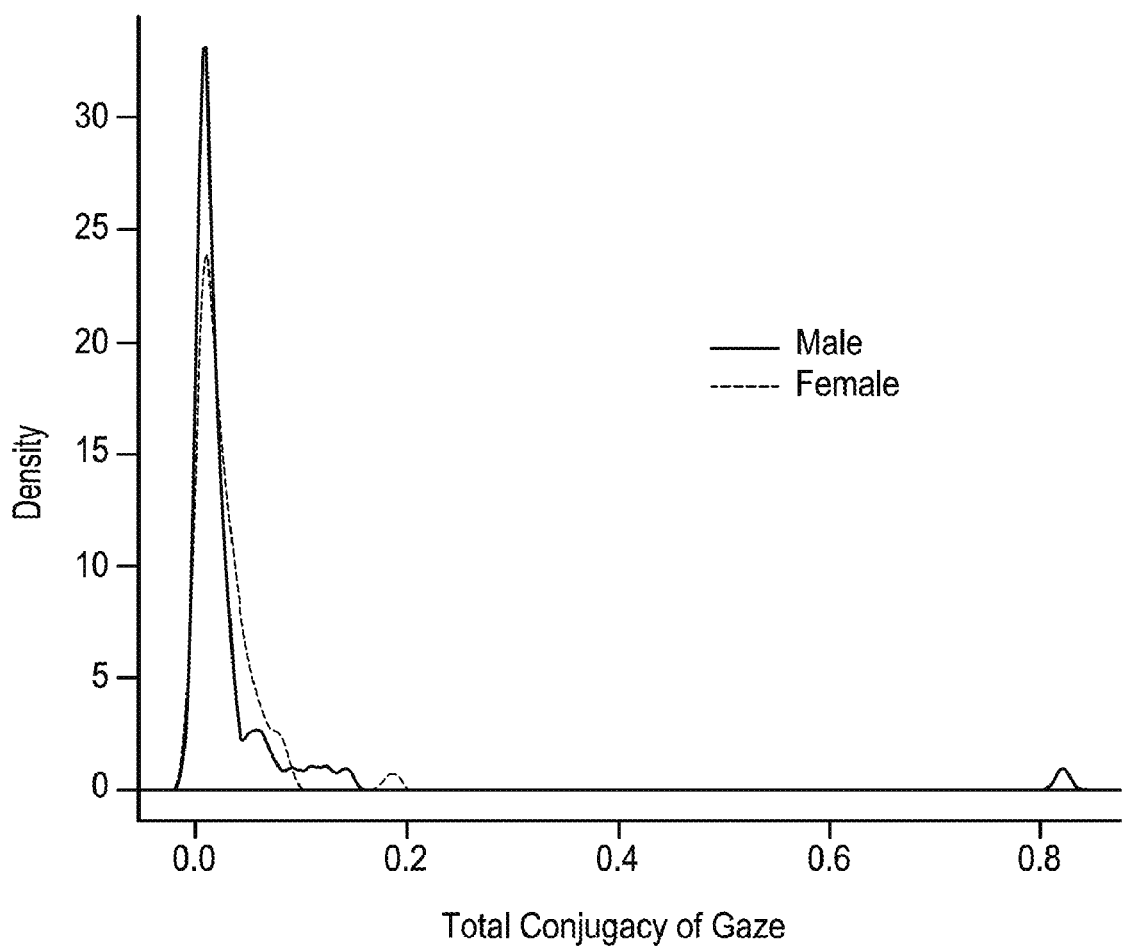
FIG. 8 represents male versus female conjugacy of eye movements. Normal subjects demonstrated conjugate eye movement that was not impacted by gender. A Welch Two Sample t-test with 68.49 degrees of freedom resulted in a t-statistic of 0.6734 and a p-value of 0.5029 showing that the difference in the means was not statistically significantly different from 0.

Normal subjects demonstrated conjugate eye movement that was not impacted by gender (FIG. 8). A Welch Two Sample t-test with 68.49 degrees of freedom resulted in a t-statistic of 0.6734 and a p-value of 0.5029 showing that the difference in the means was not statistically significantly different from 0.

Figure 9:
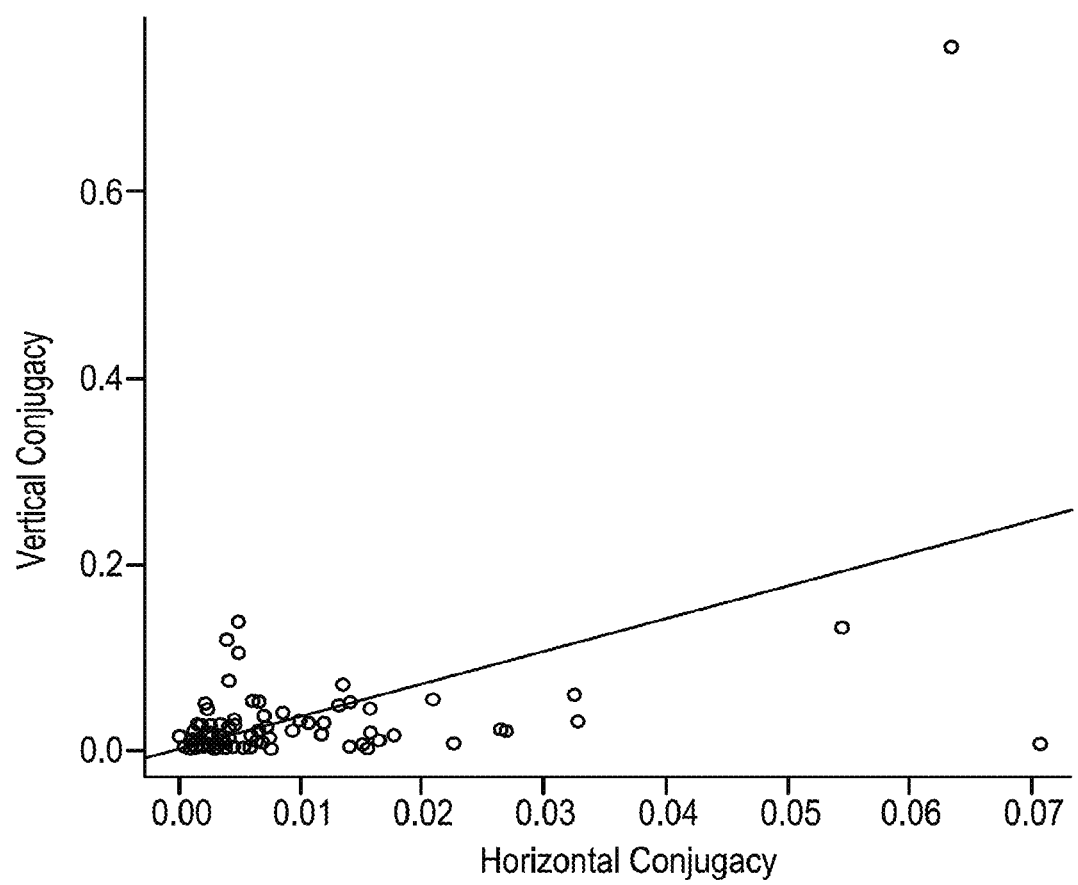
FIG. 9 represents X (horizontal) versus Y (vertical) conjugacy. Normal subjects demonstrated horizontal eye movement that was statistically highly significantly more conjugate than vertical eye movement. A paired t-test was used to determine if the mean of the subject-paired differences between the total x-variance and total y-variance was statistically significantly different from 0. With 124 degrees of freedom, the test resulted in a t-statistic of −3.0263 and a p-value of 0.003011 showing that the mean of the subject-paired differences was statistically highly significantly different from 0. Specifically, it was shown that for a particular subject, x-variance is statistically significantly less than y-variance.

Normal subjects demonstrated horizontal eye movement that was statistically highly significantly more conjugate than vertical eye movement (FIG. 9). A paired t-test was used to determine if the mean of the subject-paired differences between the total x-variance and total y-variance was statistically significantly different from 0. With 124 degrees of freedom, the test resulted in a t-statistic of −3.0263 and a p-value of 0.003011 showing that the mean of the subject-paired differences was statistically highly significantly different from 0. Specifically, it was shown that for a particular subject, x-variance is statistically significantly less than y-variance.

Figure 10:
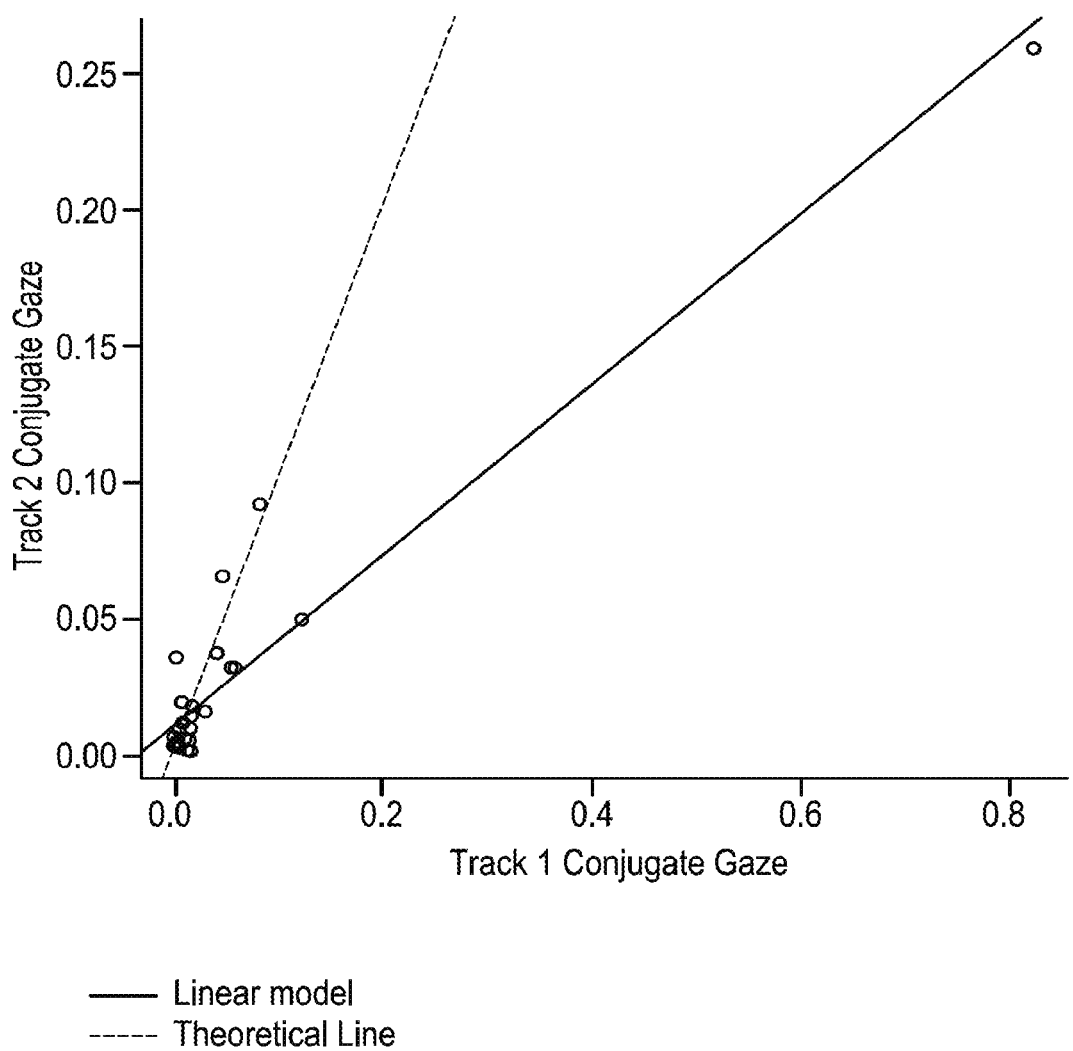
FIG. 10 demonstrates the test-retest reliability of a stationary to stationary tracker. Subjects (n=27) demonstrated high test-retest reliability between two separate eyetracking sessions on the stationary tracker. A paired t-test was used to determine if the mean of the subject-paired differences between the total variances for two separate eyetracking sessions was statistically significantly different from 0. With 26 degrees of freedom, the test resulted in a t-statistic of 1.2778 and a p-value of 0.2126 showing that the mean of the subject-paired differences was not statistically significantly different from 0.

Subjects (n=27) demonstrated high test-retest reliability between two separate eyetracking sessions on the stationary tracker (FIG. 10). A paired t-test was used to determine if the mean of the subject-paired differences between the total variances for two separate eyetracking sessions was statistically significantly different from 0. With 26 degrees of freedom, the test resulted in a t-statistic of 1.2778 and a p-value of 0.2126 showing that the mean of the subject-paired differences was not statistically significantly different from 0.

Figure 11:
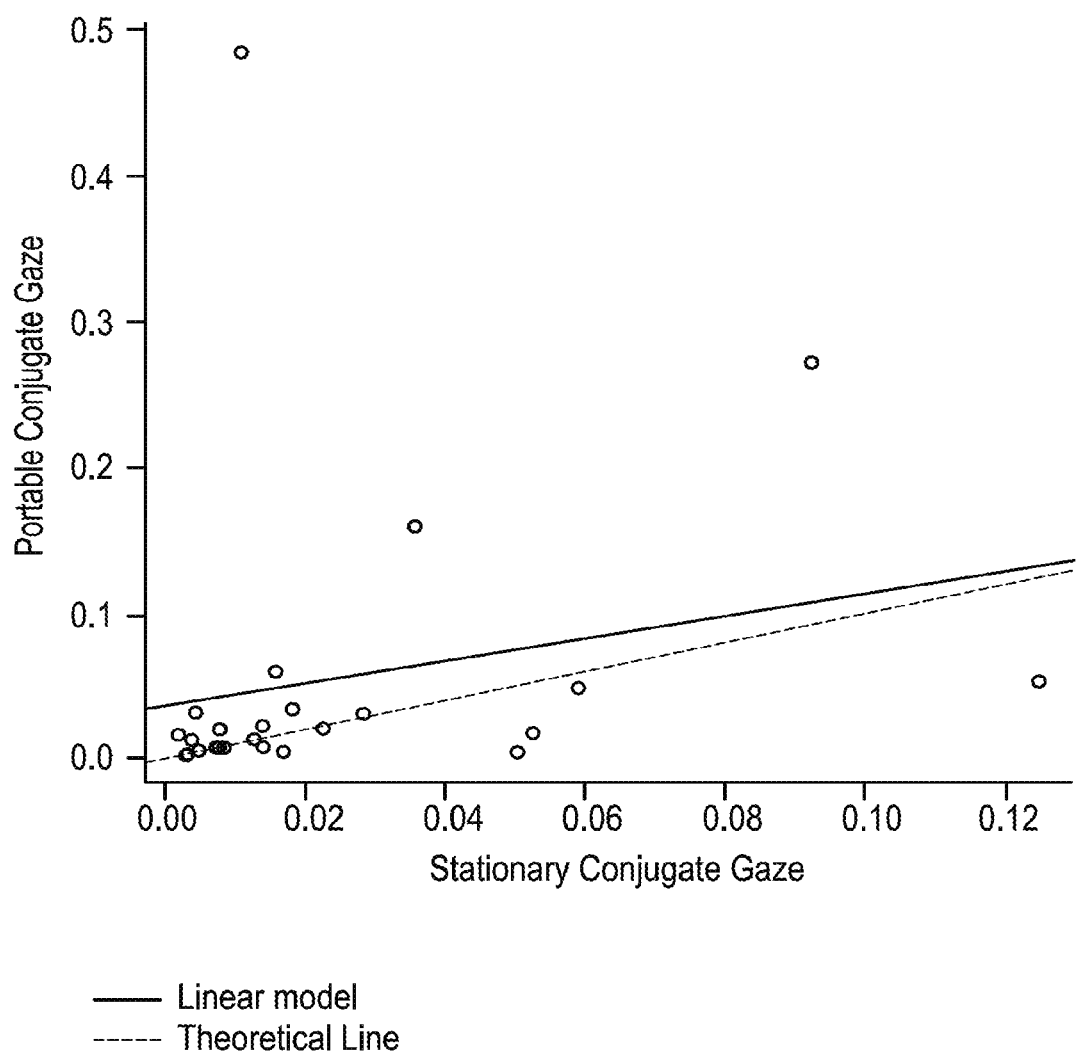
FIG. 11 demonstrates the test retest reliability of a stationary to portable tracker. Subjects (n=24) demonstrated high test-retest reliability between separate eyetracking sessions on the stationary tracker and the portable tracker (FIG. 10). A paired t-test with 23 degrees of freedom (n=24), resulted in a t-statistic of 1.3661 and a p-value of 0.1851 showing that the mean of the subject-paired differences was not statistically significantly different from 0.
Figure 12E:
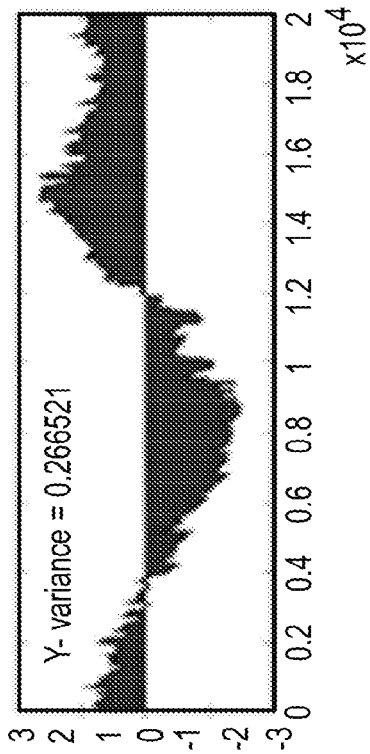
FIGS. 12A-P provide the eye movement tracking trajectories of subjects with cranial nerve IV, III and VI palsies.
Figure 12F:
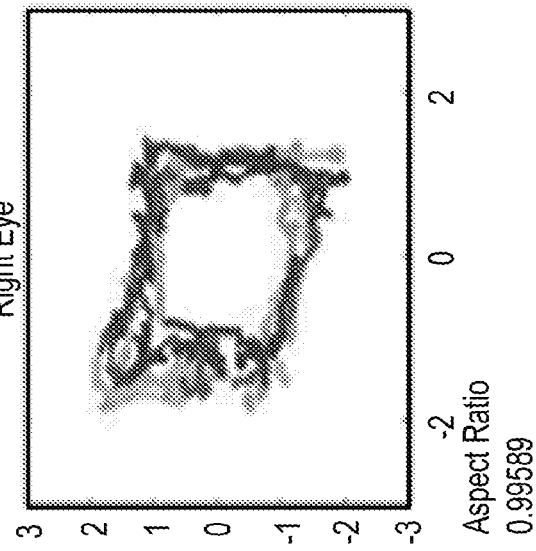
Figure 12G:
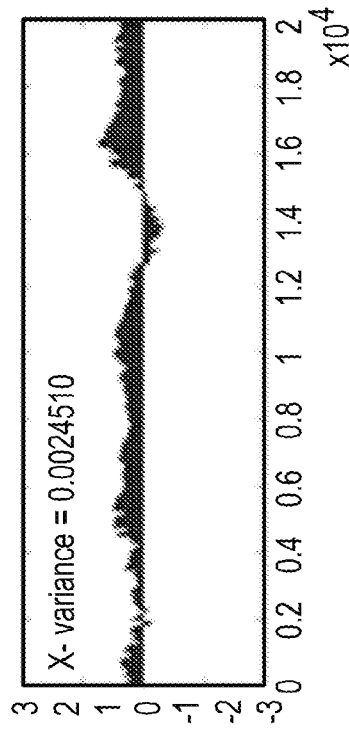
Figure 12H:
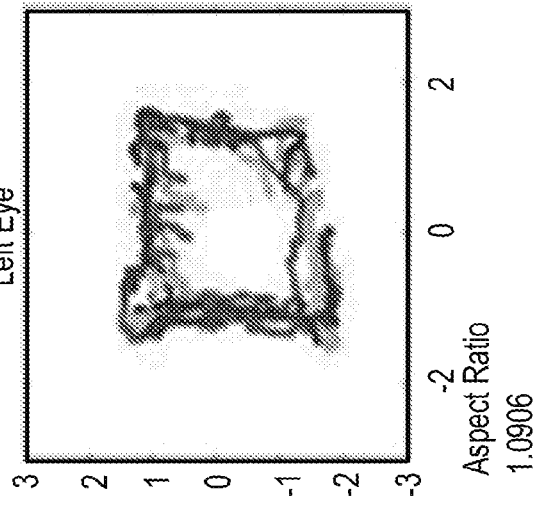
Figure 12I:
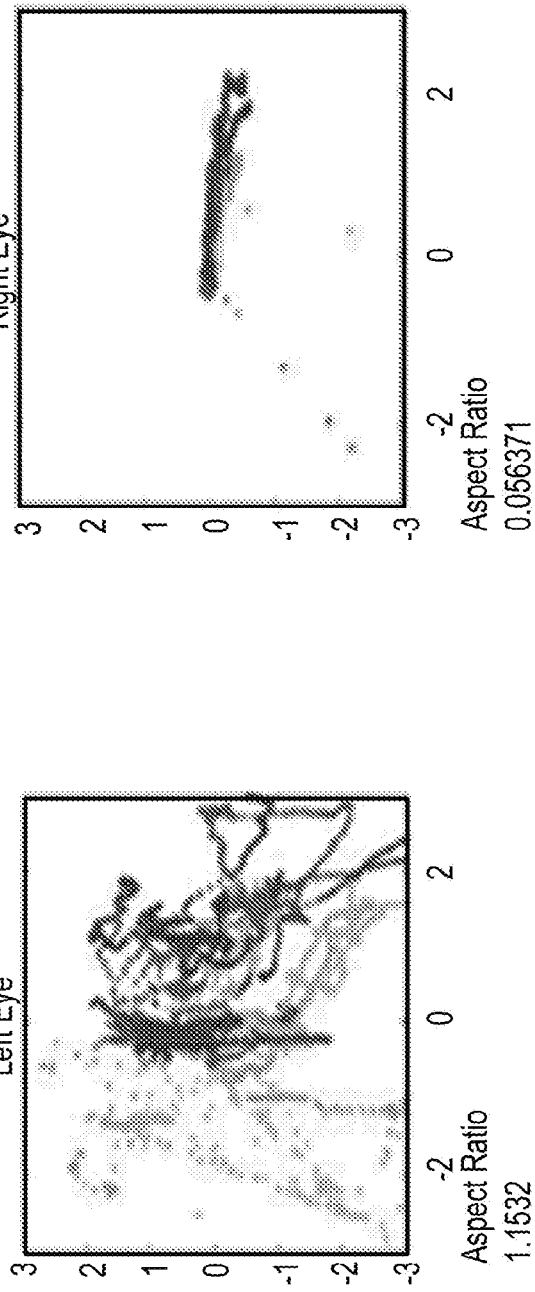
Figure 12J:
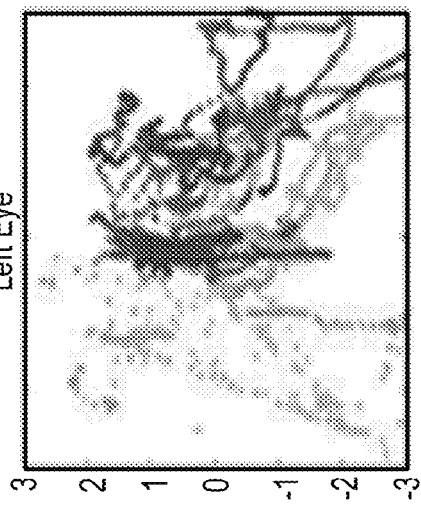
Figure 12K:
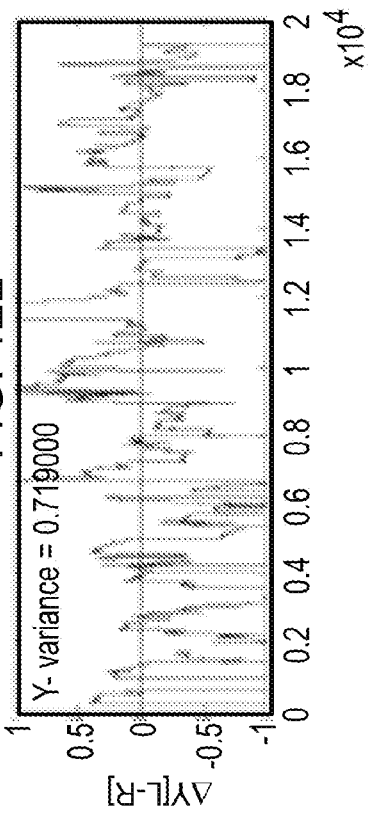
Figure 12L:
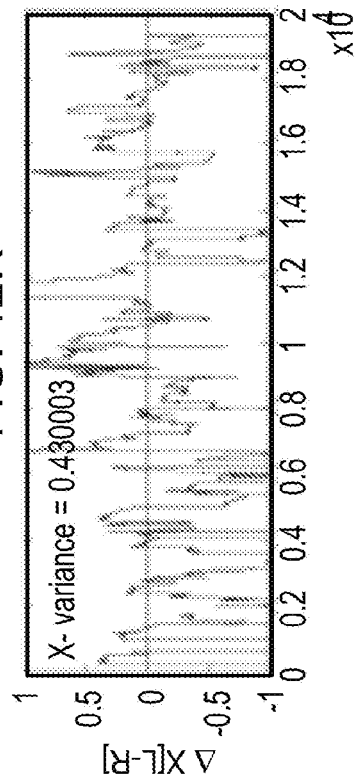

Subjects (n=24) demonstrated high test-retest reliability between separate eyetracking sessions on the stationary tracker and the portable tracker (FIG. 11). A paired t-test with 23 degrees of freedom (n=24), resulted in a t-statistic of 1.3661 and a p-value of 0.1851 showing that the mean of the subject-paired differences was not statistically significantly different from 0.

Figure 1A:
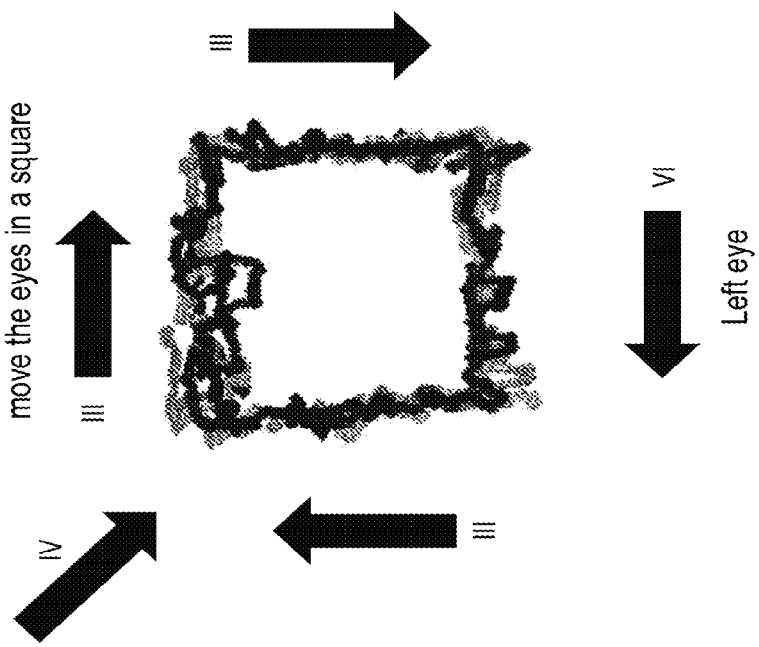
Figure 3A:
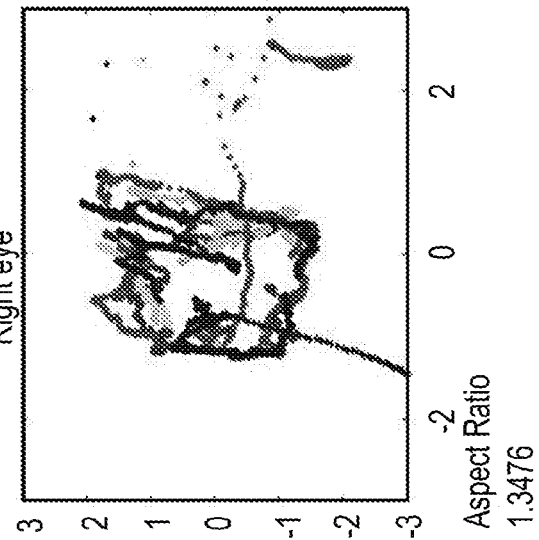
FIGS. 3A-D demonstrate the binocular eye tracking of a subject who underwent surgical evacuation of an acute on chronic subdural hematoma.
Figure 3B:
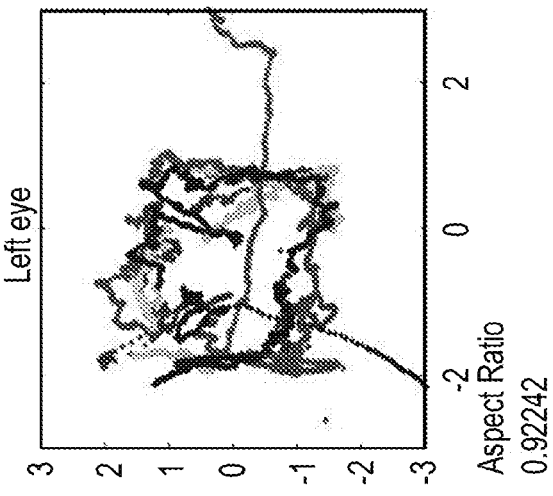
Figure 3C:
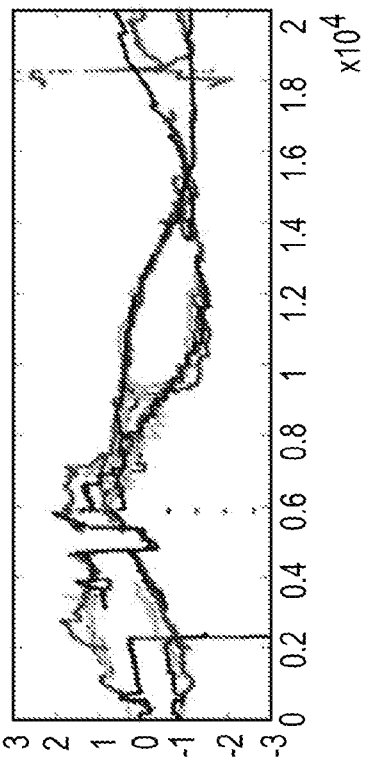
Figure 3D:
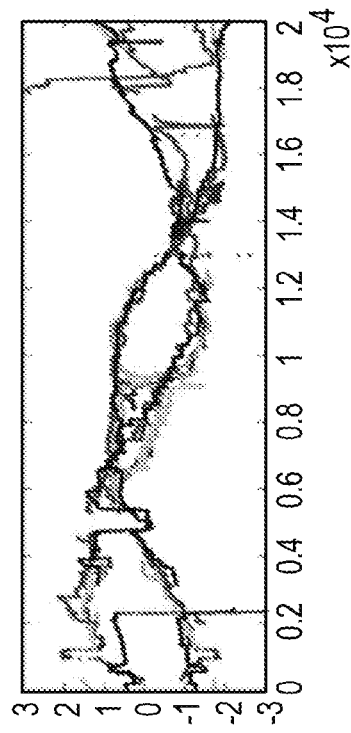
Figure 5A:
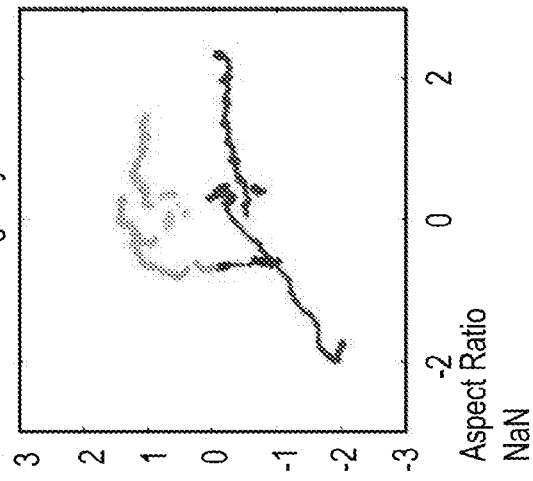
FIGS. 5A-D demonstrate the binocular tracking of a subject with concussion. The subject experienced a witnessed fall with blunt head trauma while attending a clinic in the hospital.
Figure 5B:
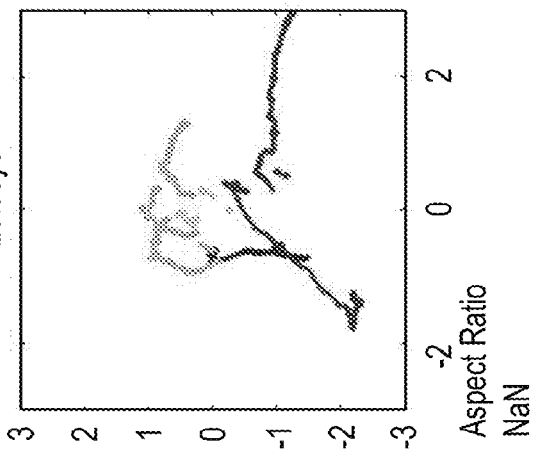
Figure 5C:
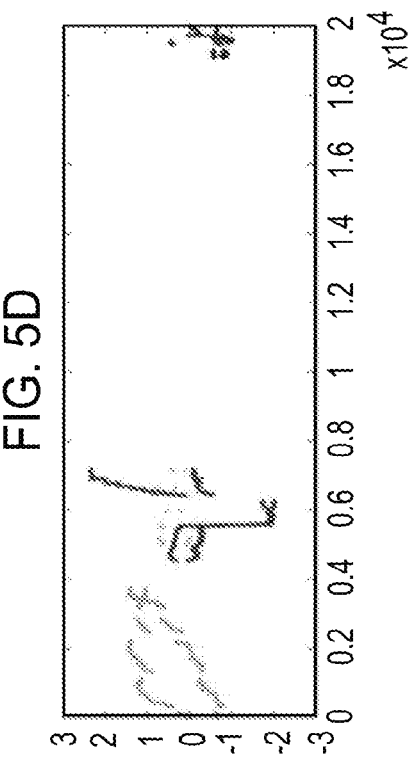
Figure 5D:
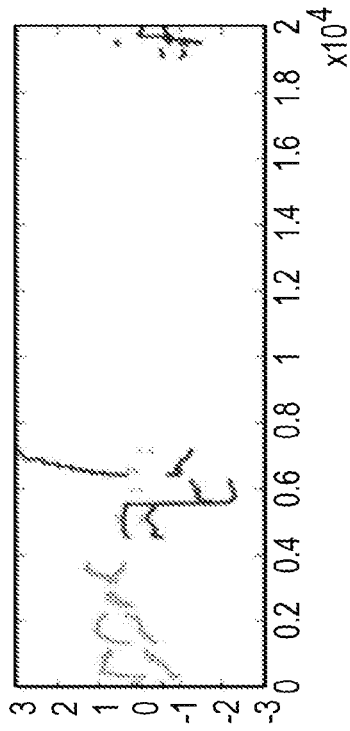
Figure 6A:
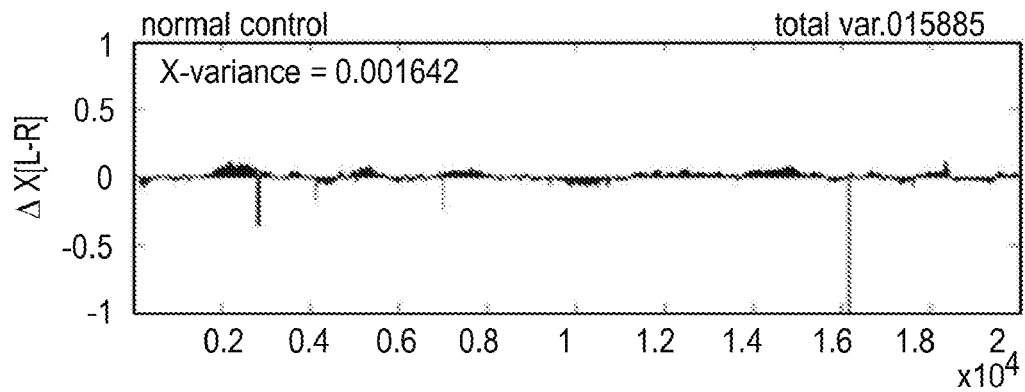
FIGS. 6A-H demonstrate that binocular eye movement tracking may be useful to quantitate the extent of physiologic brain injury. The eye box trajectory from a normal subject shows highly conjugate gaze (FIG. 6A, x-plane.
Figure 6B:
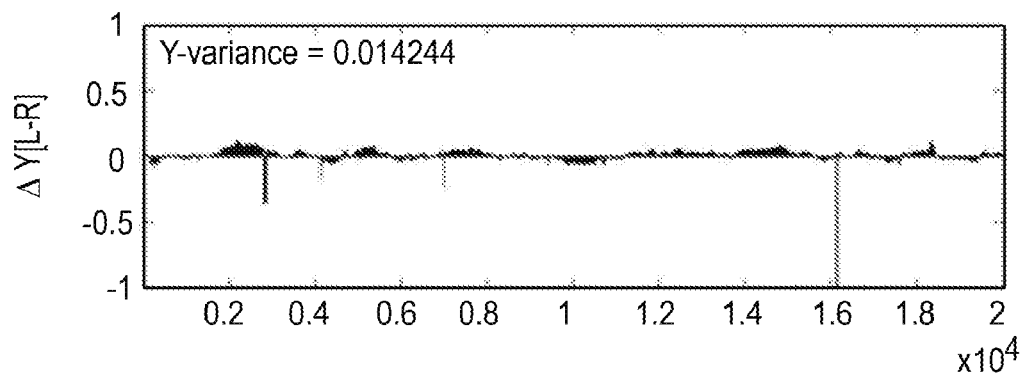
Figure 6C:
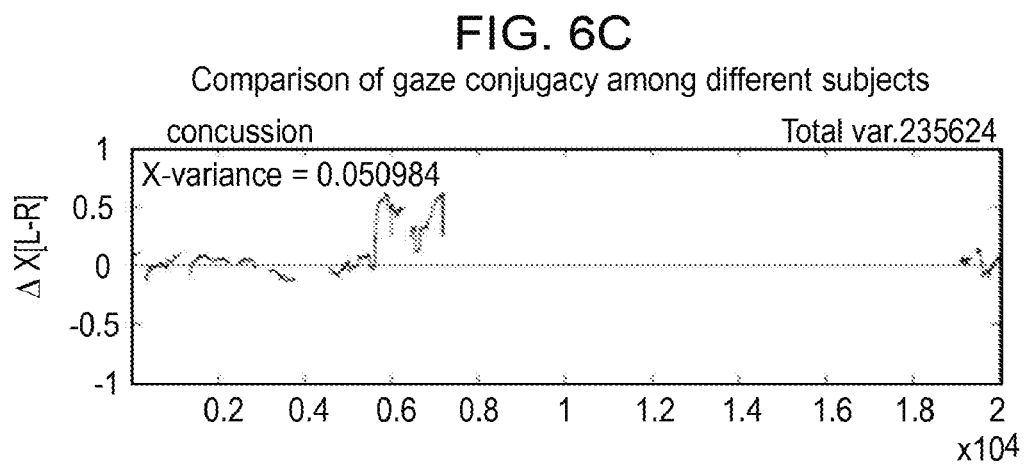
Figure 6D:
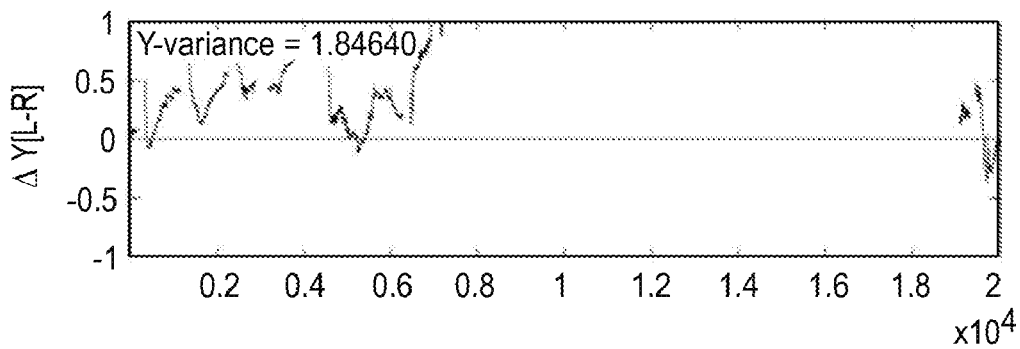
Figure 6E:
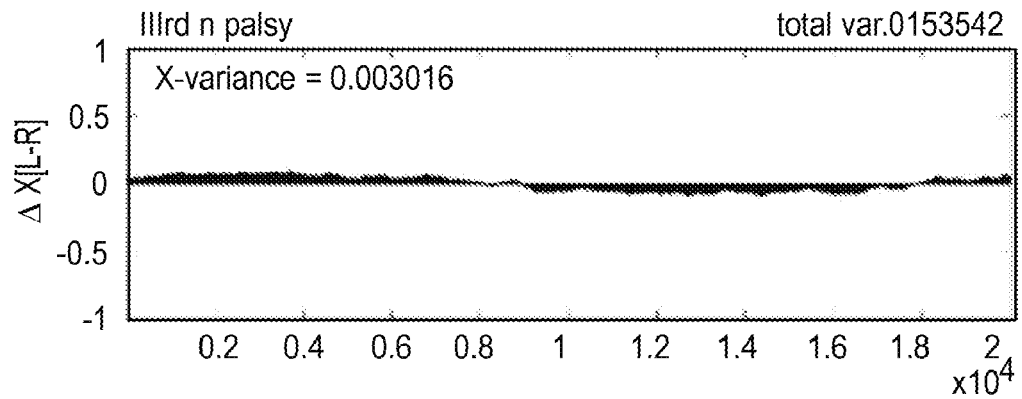
Figure 6F:
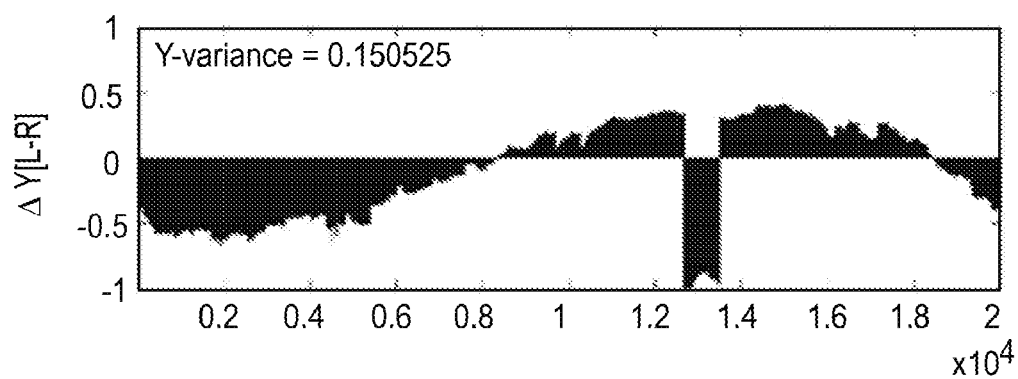
Figure 6G:
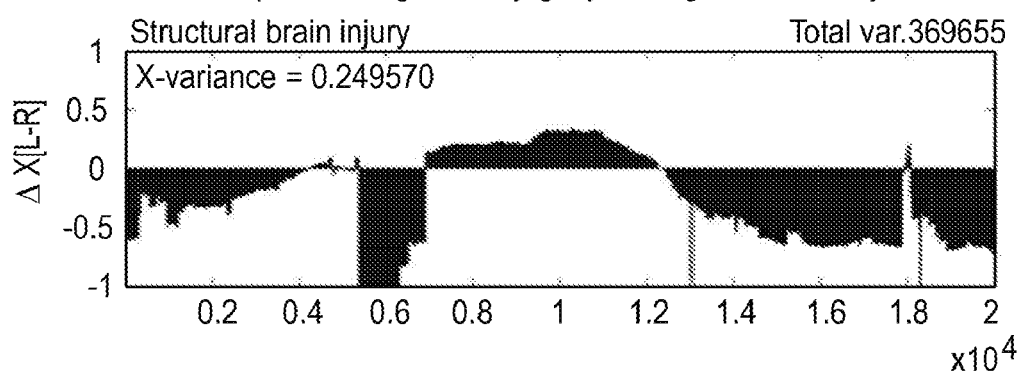
Figure 6H:
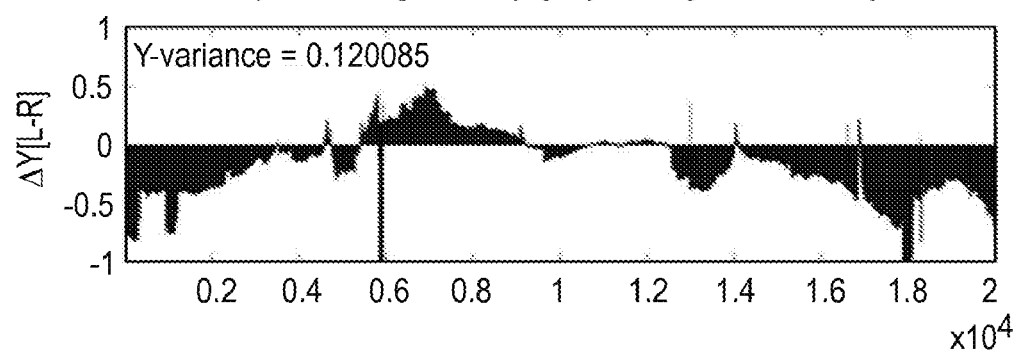

FIG. 1 represents the eye tracking trajectories of subjects with normal compared to known (well-defined) neurophthalmic abnormality.

Example 4

Materials and Methods.

Four groups of subjects were selected as follows:

(1) subjects who have mild to moderate structural traumatic brain injury (TBI) as evidenced by CT scan demonstrating the presence of hemorrhage (subdural, epidural, subarachnoid or intraparenchymal), brain contusion, or skull fracture.

(2) non-structural TBI subjects (mild TBI/concussion), meaning they show no signs of structural injury on imaging; however, they complain of usual brain injury symptoms such as headache, dizziness, cognitive impairment, etc., A subject with mild traumatic brain injury is a person who has had a traumatically induced physiological disruption of brain function, as manifested by at least one of the following:
  a. Any period of loss of consciousness (LOC).
  b. Any loss of memory for events immediately before or after the accident.
  c. Any alteration in mental state at the time of accident (i.e. feeling dazed, disoriented, or confused).
  d. Focal neurological deficit(s) that may or may not be transient, but where the severity of the injury does not exceed the following:
    1.) Loss of consciousness of approximately 30 minutes or less
    2.) After 30 minutes, an initial Glasgow Coma Scale (GCS) of 13-15
    3.) Posttraumatic amnesia (PTA) not greater than 24 hours.

(3) non-brain injured subjects that have suffered some type of injury such as to the extremities or other parts of the body. The subjects have sustained a blunt or penetrating trauma such as, to the corpus or extremities (i.e. car accident, falling, violent act excluding interpersonal violence).

(4) Healthy non injured control subjects were employees, volunteers, visitors and patients with intact ocular motility, and ability to provide a complete ophthalmologic, medical and neurologic history as well as medications/drugs/alcohol consumed within the 24 hours prior to tracking. Exclusion criteria included any minor brain injury regardless of loss of consciousness within the previous month.

Inclusion Criteria. All patients were recruited from the Bellevue Hospital Emergency Services (Emergency Room and Trauma Bay), trauma service and neurosurgery service. They were between the ages of 18 and 60, consentable and able/willing to participate and meet criteria for distribution into one of the three subject populations (structural TBI, non-structural TBI, injured/non-TBI) described above.

Exclusion Criteria. Subjects that received minor trauma insufficiently traumatizing to result in sufficient sequelae were excluded. Subjects suffering burns, anoxic injury or multiple/extensive injuries resulting in any medical, surgical or hemodynamic instability were also excluded. Particularly for the purposes of eye tracking all subjects that were blind (no light perception), missing eyes, and not opening eyes were excluded from the research. It is pertinent that subjects are able to detect light and have both eyes in order for the eye tracking data to be effective and significant. Any physical or mental injury or baseline disability rendering task completion difficult was excluded, also inability to participate in longtitudinal care, or obvious intoxication or blood alcohol level greater than 0.2. Pregnant individuals and prisoners were also excluded from the study. Subjects with a history of: strabismus, diplopia, palsy of cranial nerves III, IV or VI, papilledema, optic neuritis or other known disorder affecting cranial nerve II, macular edema, retinal degeneration, dementia or cognitive impairment, hydrocephalus, sarcoidosis, myasthenia gravis, multiple sclerosis or other demyelinating disease, and active or acute epilepsy, stroke/hemorrhage or prior brain injury sufficiently significant to result in hospitalization were also excluded.

Subjects underwent eye tracking and SCAT3 validated concussion outcome assessment as soon as possible after their injury, and then at regular intervals during recovery (1 week and 1 month).

Eye Tracking

A portable binocular eye movement tracker was constructed by attaching an adjustable arm to a rolling cart. A computer monitor was attached to the proximal portion of the arm, and a chinrest was attached to the distal aspect of the arm such that the chinrest centered the subject's eyes 55 cm away from the monitor.

Visual Stimulus. Subjects' eye movements were recorded with an Eyelink 1000 eye tracker over a time period of 220 seconds. Portable tracker subjects were seated in either a height adjustable or height-fixed chair or bed, with the monitor height adjusted to the subject. The visual stimuli were the music videos Shakira Waka-Waka, K'naan Wavin' Flag, Mission Kashmir Bhumbroo or Michael Jackson Man in the Mirror. The video was played continuously in a square aperture with an area approximately ⅑ the screen area while moving clockwise along the outer edges of the monitor for five complete cycles of 40 seconds each. The first and last 10 seconds of each data set were discarded to yield 200 seconds of data. The afferent stimulus was presented binocularly, and eye tracking was performed binocularly. Subjects were not spatially calibrated to the tracker to enable independent analysis of each pupil position over time.

Data Analysis. The eye tracker sampled pupil position at 500 Hz, yielding 100,000 samples over 200 seconds. Scatterplots of the entire time series were created by plotting the 100,000 (x,y) pairs representing the two orthogonal components of the instantaneous angle of pupil reflection over time to create 'box trajectories' that reflected the temporal nature of the pupillary movement. These figures look like boxes, reflecting the timing of the aperture as it moved around the screen.

Metrics: 51 eye-tracking parameters were measured per subject, looking at movement in each individual eye and conjugate movement between eyes. All data were analyzed using XLSTAT version 2012.6.02 (Addinsoft SARL, Paris, France) and MedCaic version 12.6.1 (MedCalc Software, Ostend, Belgium). A p-value of ≤0.05 was deemed as statistically significant.

Eye-tracking was performed on 46 patients and 31 controls. The patients were assigned to 1 of 4 groups (+CT n=13, −CT n=23, corpus injury n=10, and healthy control).

Eye-tracking parameters were compared among the 4 groups using the Kruskal-Wallis test and multiple pair-wise were performed using the Steel-Dwass-Crichlow-Fligner procedure to compare individual groups against controls.

The sports concussion assessment tool (SCAT) was administered, and standardized assessment of concussion (SAC) scores were obtained on thirty-seven subjects. Stepwise multiple regression analysis was performed to evaluate the impact of each eye-tracking parameter on the SCAT and SAC scores. Parameters with p-values >0.1 were removed from the model.

Results

Group means were collected for each of the 51 measured parameters.

Ten of the 51 measured parameters demonstrated statistically significant differences between negative controls (either normal healthy people, or corporally injured but not brain injured controls) and both positive controls (structurally brain injured) and non-structurally brain injured people. 8 additional parameters showed statistically significant differences between negative controls (healthy normal people and corporally injured trauma patients) and patients with either structural or non-structural brain injury. 10 of the eye tracking measures showed statistically significant correlation between SCAT or SAC scores, suggesting that these eye tracking parameters correlated with a validated clinical outcome measure.

These data demonstrate the usefulness of these mathematical algorithms to detect and quantitate the extent of structural and non-structural brain injury.

Example 5

Background

Assessment of binocular gaze conjugacy in primates for research purposes is performed with the magnetic search coil technique requiring coils implanted into the bulbar conjunctiva (Schultz et al., "Short-term saccadic adaptation in the macaque monkey: a binocular mechanism," 20130116 DCOM-201306262). This technique was first described by Fuchs and Robinson in 1966 and can also be performed in humans fitted with sclera search coils designed specifically for tracking eye movements (Fuchs et al., "A method for measuring horizontal and vertical eye movement chronically in the monkey," 19661128 DCOM-19661128).

Experimentally, spatially calibrated eye movement tracking using the Bouis oculometer, which requires that the head is rigidly fixed, shows that healthy 7-year-old children have increased disconjugacy of eye movement during saccades relative to adults while both perform a reading task (Bouis et al., "An accurate and linear infrared oculometer," 19831220 DCOM-19831220; Bucci et al., "Binocular coordination of saccades in 7 years old children in single word reading and target fixation," 20051219 DCOM-20060629). Research on disconjugacy during reading can be performed using a dichoptic apparatus in which the individual eyes are spatially calibrated independently, and presented with stimuli to assess movements separately for simultaneous comparison to each other (Schotter et al., "Binocular coordination: reading stereoscopic sentences in depth," 20120504 DCOM-20120913).

A novel eye movement tracking algorithm that appears useful for quantitating gaze conjugacy, and thus disconjugacy was developed by comparing the positions of the right and left pupils over time as a video is played. 22 unique subjects aged 23 to 51 (mean 32.82±7.95, median 30.5; 95.45% female) who denied neurologic disease, recent trauma, or known ocular motility dysfunction, were presented with several stimuli. Stimulus 1 consisted of a music video playing continuously inside an aperture that moved around the perimeter of a rectangular monitor. Stimulus 2 consisted of a 580 second stimulus. The first 220 seconds consisted of a music video playing inside an aperture moving in a circle. This was followed by a 45 second English text reading task and then a mixed saccade task (pro-saccades and anti-saccades) for 295 seconds. The subjects were binocularly eye tracked from a camera placed at a fixed distance. Tracking was done using either a portable eye tracking camera mounted on a rolling cart, or a stationary eye tracking camera at a fixed distance. Right and left eye positions were compared to assess conjugacy of eye movement as the music video moved relative to time. The position of each pupil was recorded over time elapsed as the video traveled on its time course. This enabled detection of impaired ability to move the pupils relative to time and therefore relative to each other. We hypothesized that all of the tasks involved, namely saccade, reading, box and circle, would have the same conjugacy.

Materials and Methods

Patient Selection

Healthy subjects were employees, volunteers, visitors and patients at the Bellevue Hospital Center and the Steven and Alexandra Cohen Veterans Center, recruited in accordance with Institutional Review Board policy. Inclusion criteria for subjects from Bellevue Hospital Center were: age 18-60 years, vision correctable to within 20/50 bilaterally, intact ocular motility, and ability to provide a complete ophthalmologic, medical treatment/hospitalization and neurologic history, as well as medications/drugs/alcohol consumed within the 24 hours prior to tracking. Exclusion criteria were: history of strabismus, diplopia, palsy of cranial nerves III, IV or VI, papilledema, optic neuritis or other known disorder affecting cranial nerve II, macular edema, retinal degeneration, dementia or cognitive impairment, hydrocephalus, sarcoidosis, myasthenia gravis, multiple sclerosis or other demyelinating disease, active or acute epilepsy, and stroke/hemorrhage or brain injury sufficiently significant to result in hospitalization. Subjects reporting any minor brain injury regardless of loss of consciousness within the previous week were also excluded. Inclusion criteria for healthy subjects from Cohen Veterans Center were: does not meet criteria for current or lifetime mTBI/CSI, PTSD negative for current and lifetime warzone related PTSD and PTSD negative for sub-syndromal warzone related PTSD based on the DSM-V diagnostic criteria, does not meet DSM-IV diagnostic criteria for current Axis I disorders as indexed by the SCID-IV, and no current use of psychotropic medication for the past 2 months. Exclusion criteria were: diagnosis of current drug use disorder at the moderate or severe level as indicated by DSMV, lifetime history of any psychiatric disorder with psychotic features, bipolar I & II disorder, major depression with psychotic features (including partial remission) or obsessive-compulsive disorder prior to trauma exposure, depression due to GMC involving endocrine diseases, current exposure to recurrent trauma or exposure to a traumatic event within the past 3 months, prominent suicidal or homicidal ideation, active suicide attempt within the past 3 months, neurologic disorder or systemic illness affecting CNS function and major medical illness (i.e. cancer, infectious ds., HIV).

Visual Stimuli

Subjects' eye movements were recorded with an Eyelink 1000 eye tracker at a fixed distance of 55 cm from a computer monitor over a time period of 580 seconds and 220 seconds for two stimuli. For the stationary tracker the subject was seated in an adjustable height chair, using an adjustable height chinrest. Portable tracker subjects were seated in either a height adjustable or height-fixed chair, with the monitor height adjusted to the subject. The portable tracker chinrest was attached to the monitor, while the stationary tracker chinrest was attached to the same table as the computer monitor.

The stimuli were presented in series. The first stimulus involved the box task and the second involved the circle, reading and saccade tasks. The visual stimulus contained Shakira's "Waka Waka" music video. For the box task, the video was played continuously in a square aperture with an area approximately ⅛ the screen size. The aperture remained stationary at the upper left corner of the monitor screen for the first 10 seconds then moved clockwise along the outer edge of a 17-inch diameter monitor for five complete cycles of 40 seconds each, followed by an extra 10 seconds at the end of the last cycle.

The circle task consisted of a circular aperture approximately ⅛ the screen size in which the video played continuously as the aperture moved in a circular trajectory around the center of the monitor at a fixed speed.

The reading task consisted of reading a few lines of instructional text for the saccade task that immediately followed. The reading task was 45 seconds in duration. 2-4 lines of text were presented every 9-10 seconds so that there was sufficient time to completely read the text, even for slow readers.

The next 295 seconds involved a saccade/anti-saccade task where two frames were presented in pseudo-random mirrored locations around a circle. The subject was instructed to execute a pro-saccade to the salient stimulus (frame from music video) if the cue was a green box. If the cue was a red circle, the subject was instructed to inhibit the reflexive pro-saccade and execute an anti-saccade to the non-salient stimulus (pixilated color swatch). This distracter stimulus was the same frame from the music video but randomly pixilated to maintain constant luminance and color. This well-established anti-saccade task challenges cognitive processes involved in working memory, attention and response inhibition.

The first 10 seconds of each data set were discarded in the stimulus to remove any noise that could have been recorded in the initial stage. Each stimulus was presented and eye tracked binocularly. Subjects were not spatially calibrated to the tracker to enable independent analysis of each pupil position over time.

Data Analysis

The eye tracker sampled pupil position at 500 Hz, yielding 100,000 samples over 200 seconds and 290,000 samples over 580 seconds. Comparing the movement of one eye of a subject to the other eye of a subject was performed by comparing the x, y Cartesian coordinates at any time point t. For example, by subtracting the x-coordinate of the left eye from the x-coordinate of the right eye or vice versa. Also, by subtracting the y-coordinate of the left eye from the y-coordinate of the right eye or vice versa. The sum of the differences between all of the x-coordinates over the time tested, gives us information regarding the horizontal movement of the pupil. The sums of the differences in y-coordinates over time gives us information regarding vertical movement of the pupil. The total sum of the differences between both x- and y-coordinates over the time tested can be summed to obtain a measure of total disconjugacy of gaze, or calculated as an average of five trajectory cycles. In cases where a subject's data was missing at any given time point in the five cycles, the denominator of the equation was the number of cycles where the data was present. The difference in the x- and y-position, for the left and right eye, could then be computed. This vector of difference could then be plotted graphically for purposes of assessment and interpretation. To have a single metric expressing the level of pupil disconjugacy, a variance of the data may be computed with respect to an expected mean of zero. This is significant because the code assumes that a healthy subject has zero vertical or horizontal pupil position difference between each eye. The variance for either horizontal (x) or vertical (substitute y for x) movement may be computed as follows:

$$\text{Var}_x = \frac{1}{N} \sum_{i=1}^{N} ((X_{Avg,i1} - X_{Avg,i2}) - 0)^2$$

The total variance in both the horizontal and vertical planes may be computed as follows:

$$\text{Var}_{Tot} = \text{Var}_X + \text{Var}_Y$$

The variance in X, Y, and the total variance may be plotted in order to assess the amount of disconjugacy present in a subject. Statistics were evaluated using MATLAB. A linear regression between X-Variable and Y-Variable was calculated. A Wilcoxon's Signed Rank Sum Test was used to check if two variables' medians under comparison are statistically significantly different.

Results

The results obtained from the subjects is provided below in Table 6.

TABLE 6

| Comparison | p-Value | Result | Conclusion |
| --- | --- | --- | --- |
| Saccade X vs. Y | 0.0392 | Reject | X > Y |
| Box X vs. Y | 0.0003 | Reject | Y > X |
| Reading X vs. Y | 0.0022 | Reject | Y > X |
| Circle X vs. Y | 0.4264 | Accept | X = Y |
| Circle vs. Box | 0.2768 | Accept | Circle = Box |
| Saccade vs. Circle | 0.0014 | Reject | Saccade > Circle |
| Saccade vs. Reading | 0.0001 | Reject | Saccade > Reading |
| Saccade vs. Box | 0.0015 | Reject | Saccade > Box |
| Circle vs. Reading | 0.6849 | Accept | Circle = Reading |
| Box vs. Reading | 0.1396 | Accept | Box = Reading |

In Table 6 the symbol '>' is used to indicate higher disconjugacy/variance. Reject means 'Reject the null hypothesis' and Accept means 'Accept the null hypothesis'. The Null hypothesis is that X and Y in a particular comparison are equal.

Eye movement tracking has been performed for nearly 30 years to evaluate smooth pursuit, saccades, fixation, pupil size and other aspects of gaze (Heitger et al., "Impaired eye movements in post-concussion syndrome indicate suboptimal brain function beyond the influence of depression, malingering or intellectual ability," 20091009 DCOM-20100203; Maruta et al., "Visual tracking synchronization as a metric for concussion screening," 20100708 DCOM-20101013). A novel fully automatable eye tracking technique to assess conjugacy of eye movements, which does not require a trained examiner or sophisticated equipment is provided and used. Instead, the pupils of subjects are tracked via camera while they watch a computer monitor playing a music video in an aperture.

The present data compares the horizontal and vertical eye movement conjugacy of 22 subjects while they watched a variety of visual stimuli on a monitor. The visual stimulus tasks included a saccade/anti-saccade task, reading text, and watching a music video in an aperture moving in both a circle and a rectangular box shape on the monitor screen.

Conjugacy between pairs of tasks and also X and Y conjugacy within each task were compared. In FIGS. 33-39, the darker line represents the null hypothesis and the lighter line represents the best-fit line for the data observed. The results show that the saccade task induced the highest disconjugacy compared with the circle, reading and box tasks. The differences in disconjugacy of the latter three tasks were not statistically significant (at a 5% significance level). For the saccades task Y conjugacy was greater than X conjugacy. For the circle, reading and box tasks, the opposite was true.

Discussion

Horizontal and vertical eye movements result from distinct and separate neural channels. Different muscles, neurons and brain stem areas are involved depending on whether movement is in the X- or Y-plane (Bahill et al., "Oblique saccadic eye movements. Independence of horizontal and vertical channels," 19770812 DCOM-19770812). In humans and non-human-primates, the six extra ocular muscles (three pairs) that surround the eye produce all eye movements and can rotate the eye in all directions. The medial and lateral rectus muscles control the horizontal movement of each eye, while the main function of the superior and inferior recti is to control the vertical movements of the eye. The third pair, the superior and inferior oblique muscles, contributes slightly to horizontal and vertical eye movement (Zigmond et al., *Fundamental Neuroscience*, 1 ed: Elsevier Science & Technology Books, 1998). These three muscle pairs are innervated by cranial nerves III, IV, and VI. Cranial nerve III, the oculomotor nerve, innervates the superior and inferior rectus, the medial rectus and the inferior oblique. Cranial nerve IV, the trochlear nerve, innervates the superior oblique muscle. Cranial nerve VI, the abducens nerve, innervates the lateral rectus. The three pairs of nuclei are distributed through the brain stem and contain all of the oculomotor motor neurons. They are interconnected by a pathway known as the medial longitudinal fasciculus.

Eye movement direction depends on which eye muscles are activated, and this is controlled by the local circuit neurons in two gaze centers in the reticular formation. For horizontal eye movement generation, the horizontal gaze center or paramedian pontine reticular formation (PPRF) is responsible and made up of a collection of local circuit neurons near the midline in the pons. Vertical movements are the result of the vertical gaze center or rostral interstitial nucleus, which is located in the rostral part of the midbrain reticular formation (Purves et al., "Neuroscience," 2nd ed Sunderland (Mass.): Sinauer Associates, 1997).

Vertebrates normally show a response where both eyes are tightly yoked, (optokinetic nystagmus) when responding to movements in a large area of their visual field. Animals such as rabbits, primates and goldfish, show a coupling of both eyes' movements during most oculomotor behaviors. Some fish however have been observed to have independent spontaneous eye movements in each eye (e.g. pipefish Corythoichthyes intestinalis and the sandlance *Limnichthyes fasciatus*), which may be contributed to differences in lifestyle and requirements for the oculomotor system (Fritsches et al., "Independent and conjugate eye movements during optokinesis in teleost fish," 20020411 DCOM-20021004).

Figure 39:
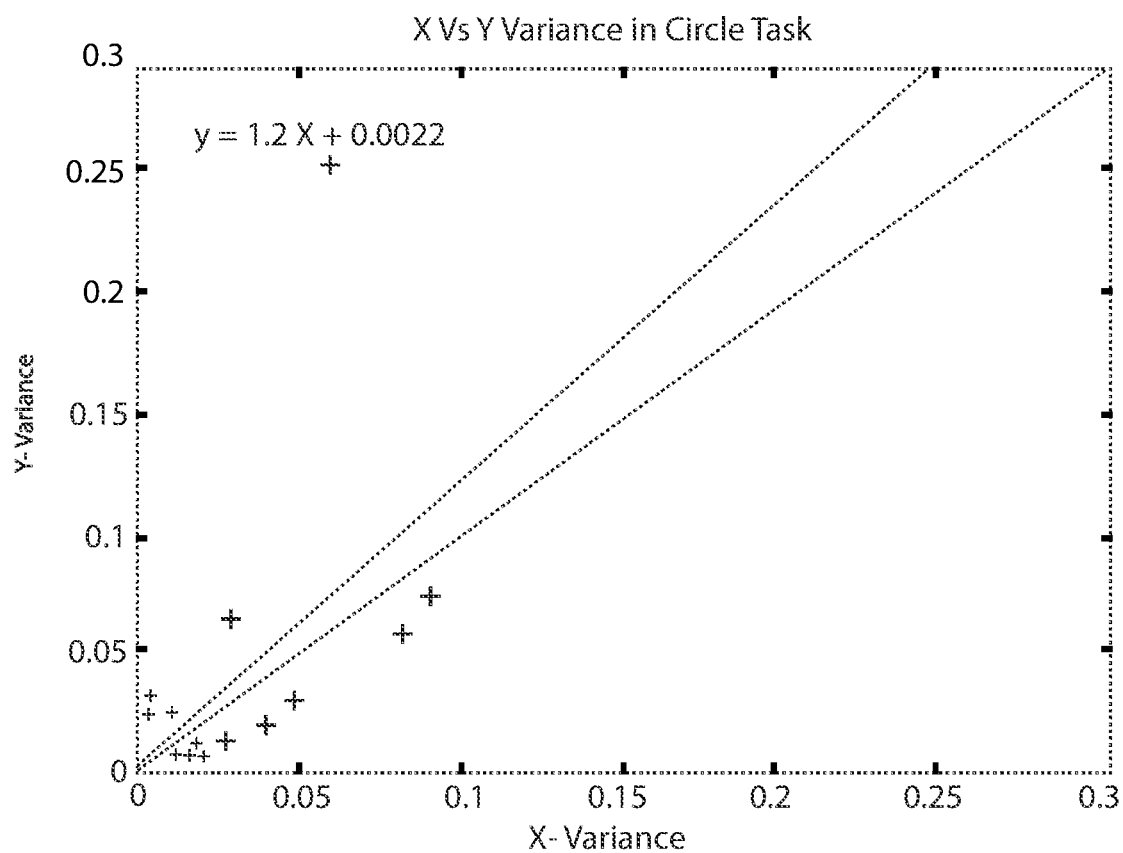
FIG. 39 indicates that subjects show significantly stronger disconjugacy during the saccades task than while performing the box, circle or reading task.

Ke et al. demonstrated that adult human smooth pursuit eye movements have a directional asymmetry for conjugacy. Smooth pursuit was observed to be significantly faster and smoother in response to downward versus upward motion, regardless of upper or lower visual field. Smooth pursuit was also more accurate and smooth in the horizontal versus vertical motion. The findings suggested that the asymmetry may be an adaptive response to visual context requirements, i.e. horizontal and downward motion directions are more critical to our survival (Ke et al., "Directional asymmetries in human smooth pursuit eye movements," 20130701 DCOM-20130912). The present experimental data for the box and circle task involved smooth pursuit. The length of each side of the box was identical. Though our box task combined the conjugacy results of looking upward and downward in the Y direction, our results were consistent with the study by Ke et al. in that overall X conjugacy was greater than Y conjugacy (p-value 0.0003, FIG. 37). Interestingly, for the circle task we found the X and Y conjugacy to be equal (FIG. 39). The result may have been affected by smooth pursuit at a constant angle instead of along a vertical or horizontal plane.

Figure 33:
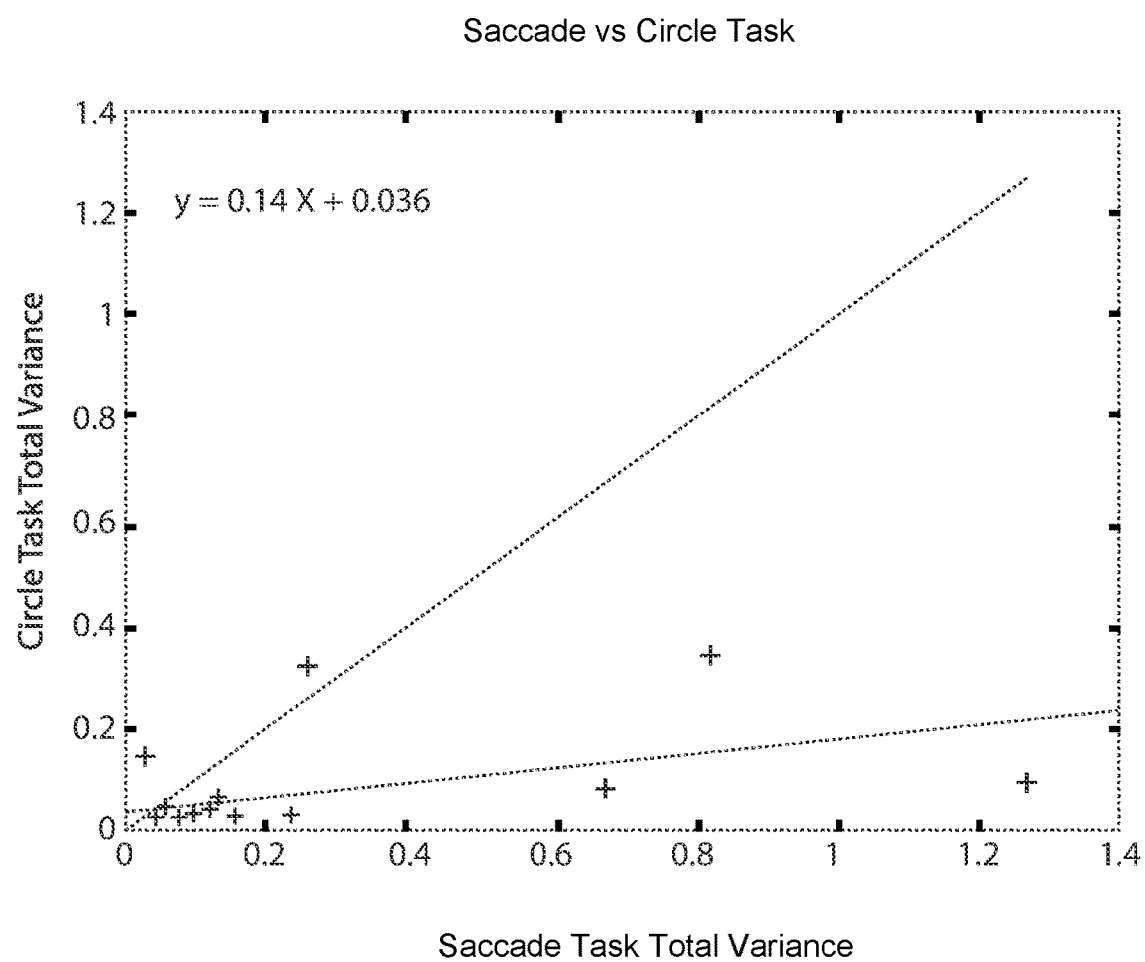
FIG. 33 indicates that subjects show significantly stronger disconjugacy during the saccades task than while performing the box, circle or reading task.
Figure 34:
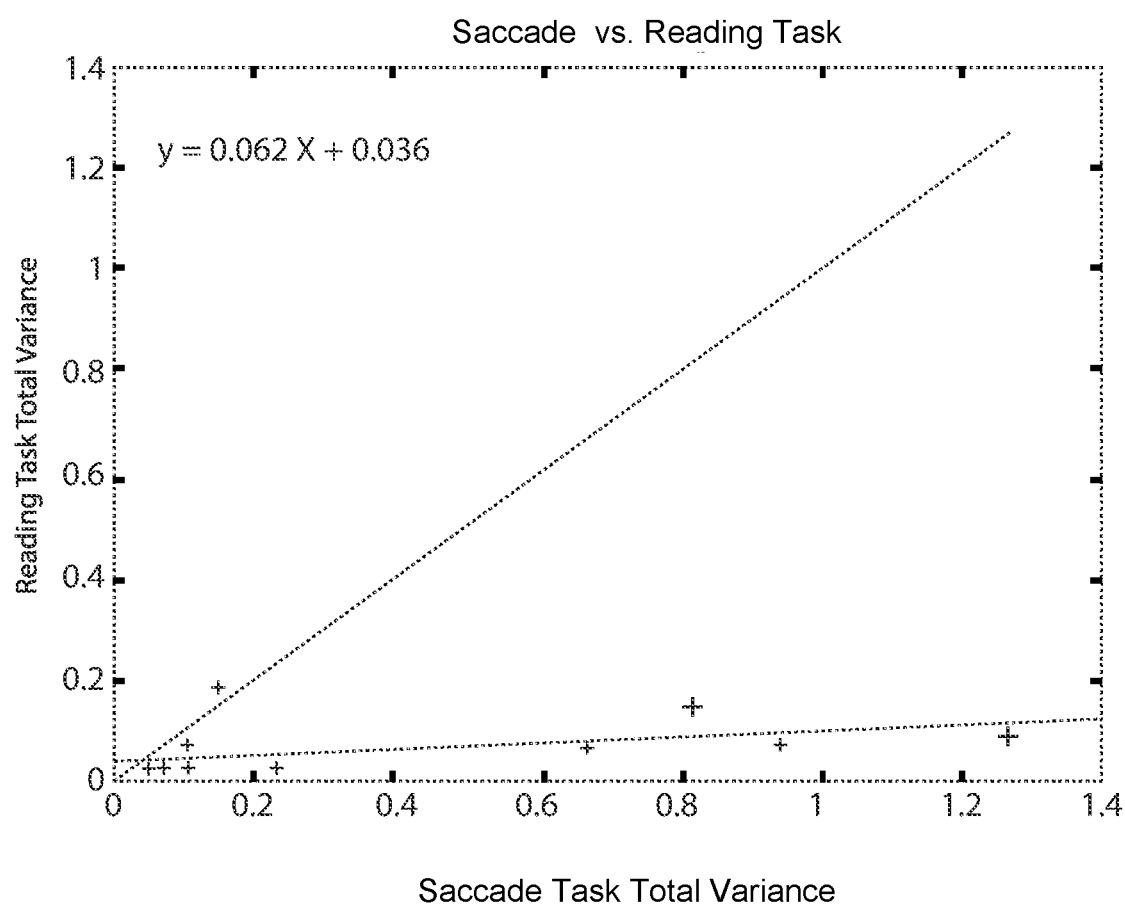
FIG. 34 indicates that subjects show significantly stronger disconjugacy during the saccades task than while performing the box, circle or reading task.
Figure 35:
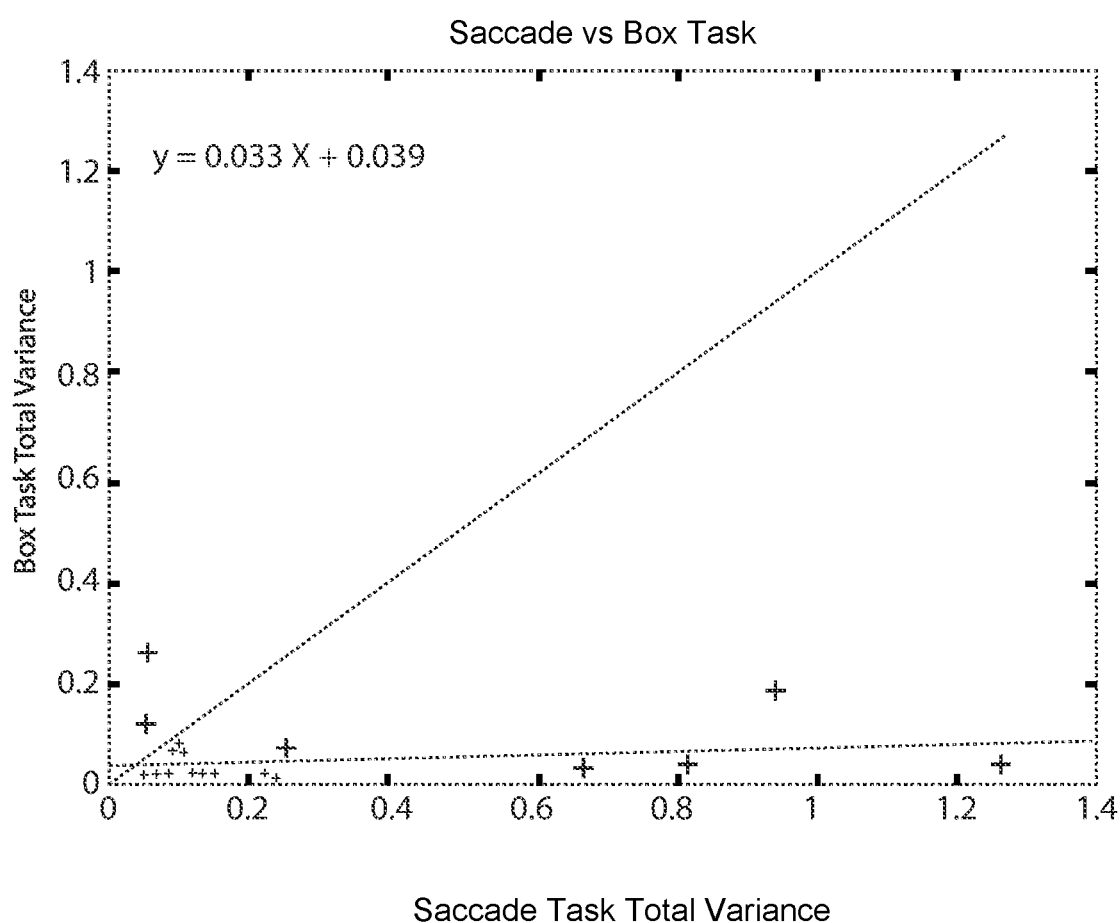
FIG. 35 indicates that subjects show significantly stronger disconjugacy during the saccades task than while performing the box, circle or reading task.
Figure 36:
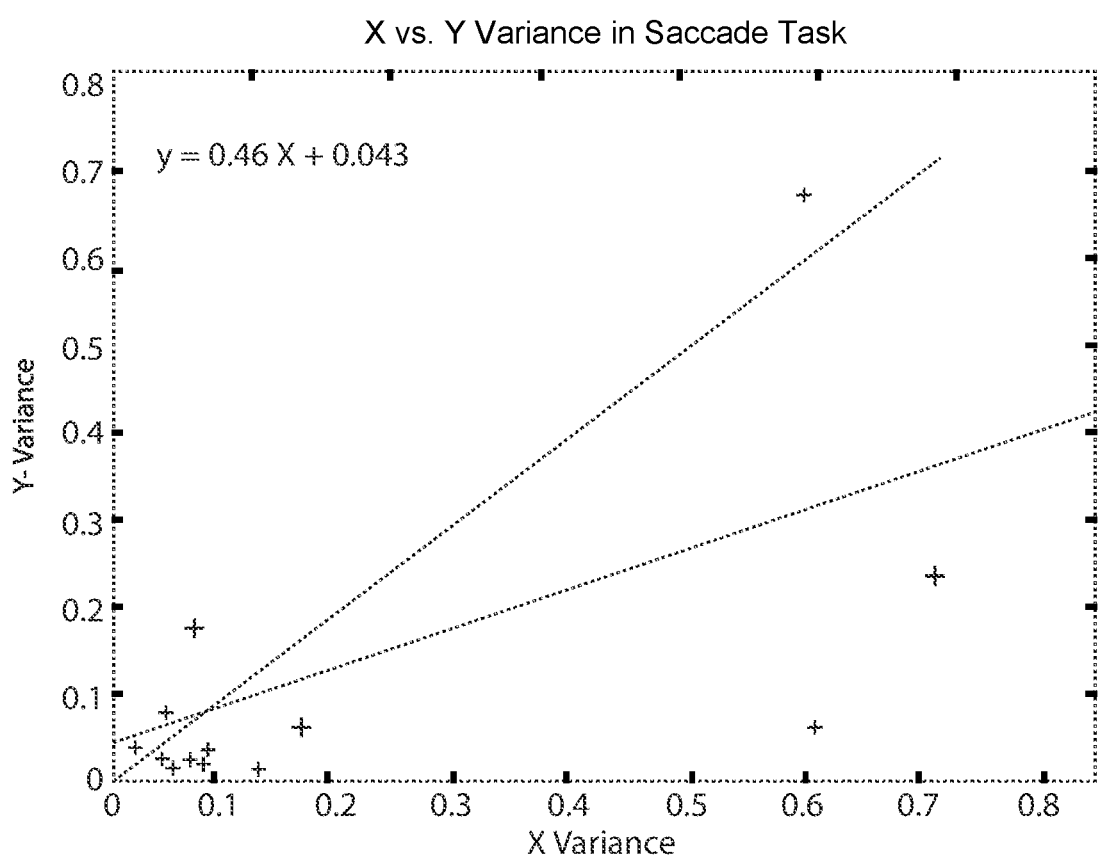
FIG. 36 indicates that subjects show significantly stronger disconjugacy during the saccades task than while performing the box, circle or reading task.
Figure 37:
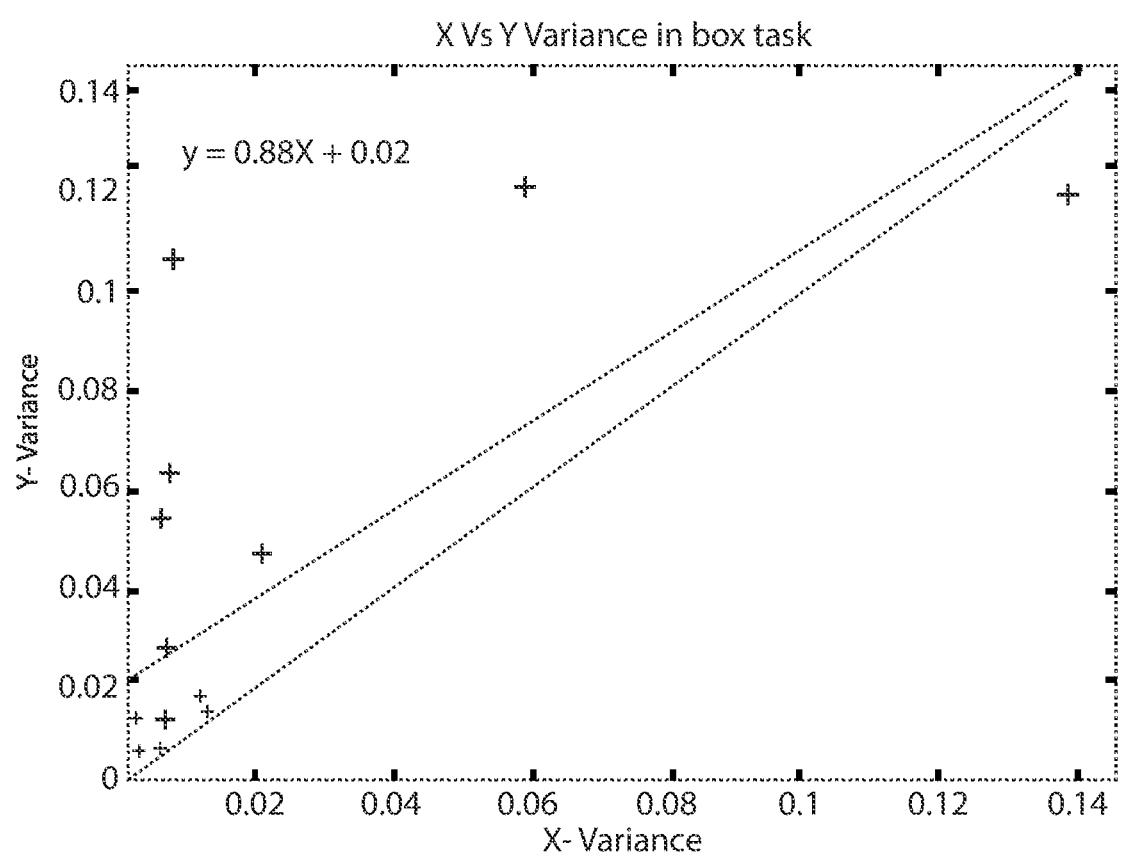
FIG. 37 indicates that subjects show significantly stronger disconjugacy during the saccades task than while performing the box, circle or reading task.
Figure 38:
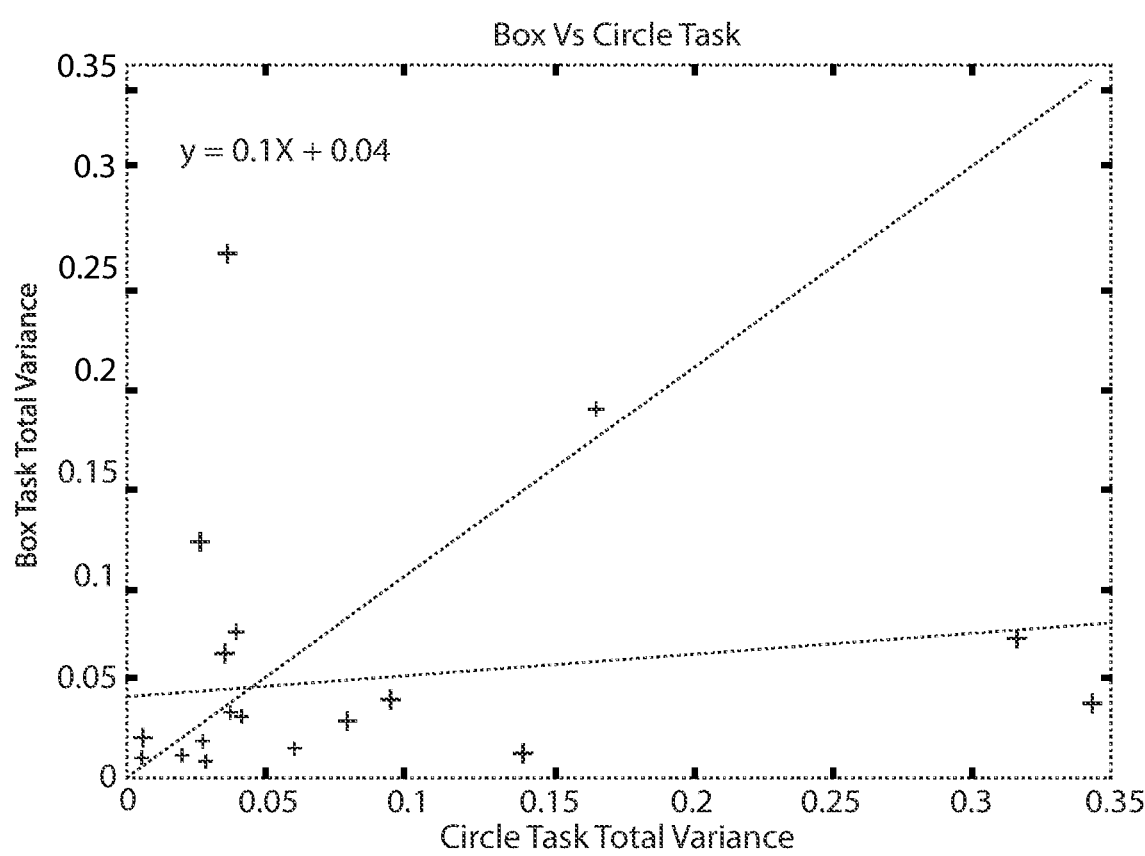
FIG. 38 indicates that subjects show significantly stronger disconjugacy during the saccades task than while performing the box, circle or reading task.

Saccades involve fast eye movements that move a point of fixation into the visual field in a conjugate manner. Horizontal saccades that become disconjugate may be a sign of several disorders affecting sites such as extraocular muscles and the brainstem (Serra et al., "Diagnosing disconjugate eye movements: phase-plane analysis of horizontal saccades," 20081007 DCOM-20081031). These data indicate that subjects show significantly stronger disconjugacy during the saccades task than while performing the box, circle or reading task (FIGS. 33, 34, 35). Within the saccade task, Y conjugacy was also stronger than X conjugacy (FIG. 36). It has been observed that horizontal saccades are faster than vertical saccades. Downward saccades have the smallest velocities and their durations are longer (Terrybahill, *Mathematical Biosciences*, 1975; 27:287-298; Thomas, "The dynamics of small saccadic eye movements," 19690216 DCOM-19690216). These results may suggest that a vertical, thus slower, saccade results in a higher degree of conjugacy. If so, this would explain why Y conjugacy was greater in the saccades task, and also why the saccades task was more disconjugate than tasks requiring slower smooth pursuit velocities (e.g. the box and circle tasks).

Reading involves alternating between fixations and saccadic eye movements (Rayner, "Eye movements in reading and information processing: 20 years of research," 19981230 DCOM-19981230). The present data from the reading task gave us conjugacy results opposite to those of the saccades task (FIG. 34). These data demonstrate that conjugacy was greater in the X direction than the Y direction during reading. Greater X conjugacy may potentially reflect the importance of effective horizontal visual input on human survival from an evolutionary standpoint, since predators and prey were more likely to be in the horizontal than vertical plane. It should also be noted that for the reading task, the distance the eyes had to travel vertically (moving from one line of text to the one below) was significantly shorter than the distance the eyes needed to travel horizontally to read the line of text. This may have contributed to greater X conjugacy if the overall horizontal velocity was slower than the vertical velocity as discussed above.

Experiments such as a box and circle task given over a larger diameter could be used to test peripheral vision. Because some of the studies cited were specific in their direction when measuring smooth pursuit, separating the up, down, left and right components of our tasks for analysis might yield interesting results.

The invention claimed is:

1. A method for assessing neurological function in a subject, comprising:
   a) prompting the subject to follow a moving saccade-evoking stimulus on a display;
   b) tracking eye movement of the subject while the subject follows the moving saccade-evoking stimulus;
   c) collecting a first eye conjugacy data of the subject relating to the moving saccade-evoking stimulus;
   d) prompting the subject to observe an anti-saccade stimulus on the display;
   e) tracking eye movement of the subject while the subject observes the anti-saccade stimulus;
   f) collecting a second eye conjugacy data of the subject relating to the anti-saccade stimulus; and
   g) comparing the first eye conjugacy data with the second eye conjugacy data.

2. The method of claim 1, wherein the moving saccade-evoking stimulus comprises a video that moves on the display.

3. The method of claim 1, wherein the moving saccade-evoking stimulus comprises a video that moves around a perimeter.

4. The method of claim 1, wherein the anti-saccade stimulus includes reading text on the display.

5. The method of claim 1, wherein collecting the first eye conjugacy data of the subject relating to the moving saccade-evoking stimulus comprises collecting vertical conjugacy data and horizontal conjugacy data.

6. The method of claim 1, further comprising the step of comparing vertical conjugacy data and horizontal conjugacy data.

7. The method of claim 1, further comprising the step of analyzing whether the moving saccade-evoking stimulus results in greater disconjugacy than the anti-saccade stimulus.

8. The method of claim 1, further comprising the step of producing a graphical representation of conjugacy during moving saccade-evoking stimulus and the anti-saccade stimulus.

* * * * *